(12) United States Patent
Burke et al.

(10) Patent No.: US 7,494,816 B2
(45) Date of Patent: Feb. 24, 2009

(54) SYSTEM AND METHOD FOR DETERMINING A TEMPERATURE DURING ANALYTE MEASUREMENT

(75) Inventors: David W. Burke, Carmel, IN (US); Lance S. Kuhn, Fishers, IN (US); Terry A. Beaty, Indianapolis, IN (US); Vladimir Svetnik, Morristown, NJ (US)

(73) Assignees: Roche Diagnostic Operations, Inc., Indianapolis, IN (US); Roche Operations Ltd., Hamilton (BM)

( * ) Notice: Subject to any disclaimer, the term of this patent is extended or adjusted under 35 U.S.C. 154(b) by 737 days.

(21) Appl. No.: 10/687,668

(22) Filed: Oct. 17, 2003

(65) Prior Publication Data

US 2004/0157338 A1 Aug. 12, 2004

Related U.S. Application Data

(60) Continuation-in-part of application No. 10/264,890, filed on Oct. 4, 2002, now abandoned, which is a division of application No. 09/530,171, filed as application No. PCT/US98/27203 on Dec. 21, 1998, now Pat. No. 6,645,368, which is a continuation-in-part of application No. 08/996,280, filed on Dec. 22, 1997, now abandoned.

(60) Provisional application No. 60/480,298, filed on Jun. 20, 2003.

(51) Int. Cl.
*G01N 33/50* (2006.01)
*G01N 27/06* (2006.01)
*G01N 27/27* (2006.01)

(52) U.S. Cl. .................. 436/94; 422/82.01; 422/82.02; 436/43; 436/46; 436/68; 436/93; 436/95; 436/131; 436/149; 436/150; 436/151

(58) Field of Classification Search ............. 422/55–58, 422/82.01–82.04; 436/43, 46, 68, 93–95, 436/131, 149–151, 183
See application file for complete search history.

(56) References Cited

U.S. PATENT DOCUMENTS 3,526,480 A 9/1970 Findl et al.

(Continued)

FOREIGN PATENT DOCUMENTS

AU 737 787 8/2001

(Continued)

OTHER PUBLICATIONS

Yamakoshi, K. I. et al, IEEE transactions on bio-medical engineering, 1980, 27, 156-161.*

(Continued)

*Primary Examiner*—Arlen Soderquist
(74) *Attorney, Agent, or Firm*—Woodard, Emhardt, Moriarty, McNett & Henry LLP

(57) ABSTRACT

A method of measuring an analyte in a biological fluid comprises applying an excitation signal having a DC component and an AC component. The AC and DC responses are measured; a corrected DC response is determined using the AC response; and a concentration of the analyte is determined based upon the corrected DC response. Other methods and devices are disclosed.

24 Claims, 36 Drawing Sheets

U.S. PATENT DOCUMENTS

| | | |
|---|---|---|
| 3,551,295 A | 12/1970 | Dyer |
| 3,621,381 A | 11/1971 | Eckfeldt |
| 3,715,192 A | 2/1973 | Wenz et al. |
| 3,720,093 A | 3/1973 | Gill |
| 3,763,422 A | 10/1973 | MacPhee et al. |
| 3,770,607 A | 11/1973 | Williams |
| 3,776,832 A | 12/1973 | Oswin et al. |
| 3,838,033 A | 9/1974 | Mindt et al. |
| 3,902,970 A | 9/1975 | Levin |
| 3,919,627 A | 11/1975 | Allen |
| 3,925,183 A | 12/1975 | Oswin et al. |
| 3,937,615 A | 2/1976 | Clack et al. |
| 3,980,437 A | 9/1976 | Kishimoto et al. |
| 4,005,002 A | 1/1977 | Racine et al. |
| 4,008,448 A | 2/1977 | Muggli |
| 4,040,908 A | 8/1977 | Clark, Jr. |
| 4,053,381 A | 10/1977 | Hamblen et al. |
| 4,065,263 A | 12/1977 | Woodbridge, III |
| 4,086,631 A | 4/1978 | Vick |
| 4,123,701 A | 10/1978 | Josefsen et al. |
| 4,127,448 A | 11/1978 | Schick et al. |
| 4,184,936 A | 1/1980 | Paul et al. |
| 4,214,968 A | 7/1980 | Battaglia et al. |
| 4,217,196 A | 8/1980 | Huch |
| 4,224,125 A | 9/1980 | Nakamura et al. |
| 4,225,410 A | 9/1980 | Pace |
| 4,230,537 A | 10/1980 | Delente et al. |
| 4,233,029 A | 11/1980 | Columbus |
| 4,260,680 A | 4/1981 | Muramatsu et al. |
| 4,263,343 A | 4/1981 | Kim |
| 4,265,250 A | 5/1981 | Parker |
| 4,273,134 A | 6/1981 | Ricciardelli |
| 4,273,639 A | 6/1981 | Gottermeier |
| 4,297,569 A | 10/1981 | Flies |
| 4,301,412 A | 11/1981 | Hill et al. |
| 4,303,887 A | 12/1981 | Hill et al. |
| 4,323,536 A | 4/1982 | Columbus |
| 4,329,642 A | 5/1982 | Luthi et al. |
| 4,366,033 A | 12/1982 | Richter et al. |
| 4,407,290 A | 10/1983 | Wilber |
| 4,407,959 A | 10/1983 | Tsuji et al. |
| 4,413,407 A | 11/1983 | Columbus |
| 4,413,628 A | 11/1983 | Tamulis |
| 4,420,564 A | 12/1983 | Tsuji et al. |
| 4,431,004 A | 2/1984 | Bessman et al. |
| 4,436,094 A | 3/1984 | Cerami |
| 4,440,175 A | 4/1984 | Wilkins |
| 4,476,149 A | 10/1984 | Poppe et al. |
| 4,477,314 A | 10/1984 | Richter et al. |
| 4,477,575 A | 10/1984 | Vogel et al. |
| 4,499,423 A | 2/1985 | Matthiessen |
| 4,510,383 A | 4/1985 | Ruppender |
| 4,517,291 A | 5/1985 | Seago |
| 4,545,382 A | 10/1985 | Higgins et al. |
| 4,547,735 A | 10/1985 | Kiesewetter et al. |
| 4,552,458 A | 11/1985 | Lowne |
| 4,571,292 A | 2/1986 | Liu et al. |
| 4,578,716 A | 3/1986 | van Rijckevorsel et al. |
| 4,592,893 A | 6/1986 | Poppe et al. |
| 4,628,193 A | 12/1986 | Blum |
| 4,642,295 A | 2/1987 | Baker |
| 4,648,665 A | 3/1987 | Davis et al. |
| 4,652,830 A | 3/1987 | Brown |
| 4,654,197 A | 3/1987 | Lilja et al. |
| 4,671,288 A | 6/1987 | Gough |
| 4,676,653 A | 6/1987 | Strohmeier et al. |
| 4,679,562 A | 7/1987 | Luksha |
| 4,682,602 A | 7/1987 | Prohaska |
| 4,686,479 A | 8/1987 | Young et al. |
| 4,703,017 A | 10/1987 | Campbell et al. |
| 4,703,756 A | 11/1987 | Gough et al. |
| 4,711,245 A | 12/1987 | Higgins et al. |
| 4,713,347 A | 12/1987 | Mitchell et al. |
| 4,714,874 A | 12/1987 | Morris et al. |
| 4,731,726 A | 3/1988 | Allen, III |
| 4,734,184 A | 3/1988 | Burleigh et al. |
| 4,750,496 A | 6/1988 | Reinhart et al. |
| 4,759,828 A | 7/1988 | Young et al. |
| 4,789,804 A | 12/1988 | Karube et al. |
| 4,795,542 A | 1/1989 | Ross et al. |
| 4,797,256 A | 1/1989 | Watlington, IV |
| 4,805,624 A | 2/1989 | Yao et al. |
| 4,806,311 A | 2/1989 | Greenquist |
| 4,806,312 A | 2/1989 | Greenquist |
| 4,810,203 A | 3/1989 | Komatsu |
| 4,816,224 A | 3/1989 | Vogel et al. |
| 4,820,399 A | 4/1989 | Senda et al. |
| 4,820,636 A | 4/1989 | Hill et al. |
| 4,832,814 A | 5/1989 | Root |
| 4,834,234 A | 5/1989 | Sacherer et al. |
| 4,849,330 A | 7/1989 | Humphries et al. |
| 4,865,873 A | 9/1989 | Cole, Jr. et al. |
| 4,877,580 A | 10/1989 | Aronowitz et al. |
| 4,897,162 A | 1/1990 | Lewandowski et al. |
| 4,897,173 A | 1/1990 | Nankai et al. |
| 4,919,770 A | 4/1990 | Preidel et al. |
| 4,927,516 A | 5/1990 | Yamaguchi et al. |
| 4,929,426 A * | 5/1990 | Bodai et al. .................. 422/63 |
| 4,935,105 A | 6/1990 | Churchouse |
| 4,935,106 A | 6/1990 | Liston et al. |
| 4,935,346 A | 6/1990 | Phillips et al. |
| 4,938,860 A | 7/1990 | Wogoman |
| 4,940,945 A | 7/1990 | Littlejohn et al. |
| 4,954,087 A | 9/1990 | Lauks et al. |
| 4,956,275 A | 9/1990 | Zuk et al. |
| 4,963,814 A | 10/1990 | Parks |
| 4,970,145 A | 11/1990 | Bennetto et al. |
| 4,975,647 A | 12/1990 | Downer et al. |
| 4,976,724 A | 12/1990 | Nieto et al. |
| 4,999,582 A | 3/1991 | Parks et al. |
| 4,999,632 A | 3/1991 | Parks |
| 5,018,164 A | 5/1991 | Brewer et al. |
| 5,019,974 A | 5/1991 | Beckers |
| 5,035,862 A | 7/1991 | Dietze et al. |
| 5,039,618 A | 8/1991 | Stone |
| 5,049,487 A | 9/1991 | Phillips et al. |
| 5,053,199 A | 10/1991 | Keiser et al. |
| 5,059,394 A | 10/1991 | Phillips et al. |
| 5,066,372 A | 11/1991 | Weetall |
| 5,075,077 A | 12/1991 | Durley, III et al. |
| 5,096,669 A | 3/1992 | Lauks et al. |
| 5,108,564 A | 4/1992 | Szuminsky et al. |
| 5,112,455 A | 5/1992 | Cozzette et al. |
| 5,112,758 A | 5/1992 | Fellman et al. |
| 5,118,183 A | 6/1992 | Cargill et al. |
| 5,120,420 A | 6/1992 | Nankai et al. |
| 5,122,244 A | 6/1992 | Hoenes et al. |
| 5,126,952 A | 6/1992 | Kildal-Brandt et al. |
| 5,128,015 A | 7/1992 | Szuminsky et al. |
| 5,141,850 A | 8/1992 | Cole et al. |
| 5,141,868 A | 8/1992 | Shanks et al. |
| 5,143,694 A | 9/1992 | Schafer et al. |
| 5,179,005 A | 1/1993 | Phillips et al. |
| 5,179,288 A | 1/1993 | Miffitt et al. |
| 5,182,707 A | 1/1993 | Cooper et al. |
| 5,187,100 A | 2/1993 | Matzinger et al. |
| 5,192,415 A | 3/1993 | Yoshioka et al. |
| 5,220,920 A | 6/1993 | Gharib |
| 5,232,516 A | 8/1993 | Hed |
| 5,232,667 A * | 8/1993 | Hieb et al. ............... 422/82.04 |
| 5,232,668 A | 8/1993 | Grant et al. |
| 5,234,813 A | 8/1993 | McGeehan et al. |
| 5,243,516 A | 9/1993 | White |
| 5,246,858 A | 9/1993 | Arbuckle et al. |

| | | | | | |
|---|---|---|---|---|---|
| 5,250,439 A | 10/1993 | Musho et al. | 5,604,110 A | 2/1997 | Baker et al. |
| 5,261,411 A * | 11/1993 | Hughes ...................... 600/481 | 5,605,662 A | 2/1997 | Heller et al. |
| 5,264,103 A | 11/1993 | Yoshioka et al. | 5,605,837 A | 2/1997 | Karimi et al. |
| 5,266,179 A | 11/1993 | Nankai et al. | 5,611,900 A | 3/1997 | Worden et al. |
| 5,269,891 A | 12/1993 | Colin | 5,620,579 A | 4/1997 | Genshaw et al. |
| 5,279,294 A | 1/1994 | Anderson et al. | 5,620,863 A | 4/1997 | Tomasco et al. |
| 5,281,395 A | 1/1994 | Markart et al. | 5,628,890 A | 5/1997 | Carter et al. |
| 5,284,770 A | 2/1994 | Adrian et al. | 5,630,986 A | 5/1997 | Charlton et al. |
| 5,286,362 A | 2/1994 | Hoenes et al. | 5,635,362 A | 6/1997 | Levine et al. |
| 5,288,636 A | 2/1994 | Pollmann et al. | 5,635,364 A | 6/1997 | Clark et al. |
| 5,296,192 A | 3/1994 | Carroll et al. | 5,639,671 A | 6/1997 | Bogart et al. |
| 5,304,468 A | 4/1994 | Phillips et al. | 5,642,734 A | 7/1997 | Ruben et al. |
| 5,306,623 A | 4/1994 | Kiser | 5,645,798 A | 7/1997 | Schreiber et al. |
| 5,311,426 A | 5/1994 | Donohue et al. | 5,650,061 A | 7/1997 | Kuhr et al. |
| 5,312,762 A | 5/1994 | Guiseppi-Elie | 5,650,062 A | 7/1997 | Ikeda et al. |
| 5,344,754 A | 9/1994 | Zweig | 5,653,863 A | 8/1997 | Genshaw et al. |
| 5,352,351 A | 10/1994 | White et al. | 5,654,178 A | 8/1997 | Fitzpatrick et al. |
| 5,353,351 A | 10/1994 | Bartoli et al. | 5,656,502 A | 8/1997 | MacKay et al. |
| 5,366,609 A | 11/1994 | White et al. | 5,658,443 A | 8/1997 | Yamamoto et al. |
| 5,371,687 A | 12/1994 | Holmes, II et al. | 5,658,802 A | 8/1997 | Hayes et al. |
| 5,376,254 A | 12/1994 | Fisher | 5,665,215 A | 9/1997 | Bussmann et al. |
| 5,379,214 A | 1/1995 | Arbuckle et al. | 5,670,031 A | 9/1997 | Hintsche et al. |
| 5,385,846 A | 1/1995 | Kuhn et al. | 5,682,884 A | 11/1997 | Hill et al. |
| 5,389,215 A | 2/1995 | Horiuchi et al. | 5,686,659 A | 11/1997 | Neel et al. |
| 5,395,504 A | 3/1995 | Saurer et al. | 5,691,486 A | 11/1997 | Behringer et al. |
| 5,405,511 A | 4/1995 | Brown et al. | 5,691,633 A | 11/1997 | Liu et al. |
| 5,411,647 A | 5/1995 | Johnson et al. | 5,695,623 A | 12/1997 | Michel et al. |
| 5,413,690 A | 5/1995 | Kost et al. | 5,698,083 A | 12/1997 | Glass |
| 5,413,764 A | 5/1995 | Haar | 5,700,695 A | 12/1997 | Yassinzadeh et al. |
| 5,418,142 A | 5/1995 | Kiser et al. | 5,708,247 A | 1/1998 | McAleer et al. |
| 5,421,189 A | 6/1995 | Dussault | 5,710,622 A | 1/1998 | Neel et al. |
| 5,424,035 A | 6/1995 | Hones et al. | 5,719,667 A | 2/1998 | Miers |
| 5,426,032 A | 6/1995 | Phillips et al. | 5,720,862 A | 2/1998 | Hamamoto et al. |
| 5,437,772 A | 8/1995 | De Castro et al. | 5,723,284 A | 3/1998 | Ye |
| 5,437,999 A | 8/1995 | Diebold et al. | 5,727,548 A | 3/1998 | Hill et al. |
| 5,438,271 A | 8/1995 | White et al. | 5,728,074 A | 3/1998 | Castellano et al. |
| 5,439,826 A | 8/1995 | Kontorovich | 5,745,308 A | 4/1998 | Spangenberg |
| 5,445,967 A | 8/1995 | Deuter | 5,748,002 A * | 5/1998 | Scott et al. .................. 324/633 |
| 5,447,837 A | 9/1995 | Urnovitz | 5,757,666 A | 5/1998 | Schreiber et al. |
| 5,453,360 A | 9/1995 | Yu | 5,759,794 A | 6/1998 | Levine et al. |
| 5,469,846 A | 11/1995 | Khan | 5,762,770 A | 6/1998 | Pritchard et al. |
| 5,470,533 A | 11/1995 | Shindo et al. | 5,776,710 A | 7/1998 | Levine et al. |
| 5,477,326 A | 12/1995 | Dosmann | 5,780,304 A | 7/1998 | Matzinger et al. |
| 5,489,414 A | 2/1996 | Schreiber et al. | 5,786,584 A | 7/1998 | Button et al. |
| 5,494,638 A | 2/1996 | Gullick | 5,788,833 A | 8/1998 | Lewis et al. |
| 5,500,350 A | 3/1996 | Baker et al. | 5,789,255 A | 8/1998 | Yu |
| 5,504,011 A | 4/1996 | Gavin et al. | 5,792,668 A | 8/1998 | Deamer et al. |
| 5,508,171 A | 4/1996 | Walling et al. | 5,798,031 A | 8/1998 | Charlton et al. |
| 5,508,200 A | 4/1996 | Tiffany et al. | 5,801,057 A | 9/1998 | Smart et al. |
| 5,508,203 A | 4/1996 | Fuller et al. | 5,820,551 A | 10/1998 | Hill et al. |
| 5,509,410 A | 4/1996 | Hill et al. | 5,820,622 A | 10/1998 | Gross et al. |
| 5,515,170 A | 5/1996 | Matzinger | 5,832,921 A | 11/1998 | Lennert et al. |
| 5,515,847 A | 5/1996 | Braig et al. | 5,834,217 A | 11/1998 | Levine et al. |
| 5,526,111 A | 6/1996 | Collins et al. | 5,837,546 A | 11/1998 | Allen et al. |
| 5,526,120 A | 6/1996 | Jina et al. | 5,843,691 A | 12/1998 | Douglas et al. |
| 5,526,808 A | 6/1996 | Kaminsky | 5,843,692 A | 12/1998 | Phillips et al. |
| 5,532,128 A | 7/1996 | Eggers et al. | 5,846,744 A | 12/1998 | Athey et al. |
| 5,552,116 A | 9/1996 | Yokota et al. | 5,849,174 A | 12/1998 | Sanghera et al. |
| 5,554,531 A | 9/1996 | Zweig | 5,856,195 A | 1/1999 | Charlton et al. |
| 5,556,789 A | 9/1996 | Goerlach-Graw et al. | 5,873,990 A | 2/1999 | Wojciechowski et al. |
| 5,563,031 A | 10/1996 | Yu | 5,883,378 A | 3/1999 | Irish et al. |
| 5,563,042 A | 10/1996 | Phillips et al. | 5,885,839 A | 3/1999 | Lingane et al. |
| 5,569,591 A | 10/1996 | Kell et al. | 5,890,489 A | 4/1999 | Elden |
| 5,569,608 A | 10/1996 | Sommer | 5,904,898 A | 5/1999 | Markart |
| 5,572,159 A | 11/1996 | McFarland | 5,911,872 A | 6/1999 | Lewis et al. |
| 5,575,895 A | 11/1996 | Ikeda et al. | 5,916,156 A | 6/1999 | Hildenbrand et al. |
| 5,576,073 A | 11/1996 | Kickelhain | 5,921,925 A | 7/1999 | Cartmell et al. |
| 5,580,794 A | 12/1996 | Allen | 5,922,530 A | 7/1999 | Yu |
| 5,582,697 A | 12/1996 | Ikeda et al. | 5,922,591 A | 7/1999 | Anderson et al. |
| 5,593,390 A | 1/1997 | Castellano et al. | 5,925,021 A | 7/1999 | Castellano et al. |
| 5,593,739 A | 1/1997 | Kickelhain | 5,945,341 A | 8/1999 | Howard, III |
| 5,594,906 A | 1/1997 | Holmes, II et al. | 5,948,289 A | 9/1999 | Noda et al. |
| 5,597,532 A | 1/1997 | Connolly | 5,951,836 A | 9/1999 | McAleer et al. |

| | | | | | | |
|---|---|---|---|---|---|---|
| 5,965,380 | A | 10/1999 | Heller | 6,287,451 B1 | 9/2001 | Winarta et al. |
| 5,968,760 | A | 10/1999 | Phillips et al. | 6,287,595 B1 | 9/2001 | Loewy et al. |
| 5,971,923 | A | 10/1999 | Finger | 6,287,875 B1 | 9/2001 | Geisberg |
| 5,989,917 | A | 11/1999 | McAleer et al. | 6,294,281 B1 | 9/2001 | Heller |
| 5,997,817 | A | 12/1999 | Crismore et al. | 6,295,506 B1 | 9/2001 | Heinonen et al. |
| 6,004,441 | A | 12/1999 | Fujiwara et al. | 6,299,757 B1 | 10/2001 | Feldman et al. |
| 6,004,442 | A * | 12/1999 | Choulga et al. ............. 204/416 | 6,300,123 B1 | 10/2001 | Vadgama et al. |
| 6,013,170 | A | 1/2000 | Meade | 6,300,142 B1 | 10/2001 | Andrews et al. |
| 6,042,714 | A | 3/2000 | Lin et al. | 6,300,961 B1 | 10/2001 | Finger et al. |
| 6,044,285 | A | 3/2000 | Chaiken et al. | 6,309,526 B1 | 10/2001 | Fujiwara et al. |
| 6,045,567 | A | 4/2000 | Taylor et al. | 6,315,951 B1 | 11/2001 | Markart |
| 6,061,128 | A | 5/2000 | Zweig et al. | 6,316,264 B1 | 11/2001 | Corey et al. |
| 6,071,391 | A | 6/2000 | Gotoh et al. | 6,325,917 B1 | 12/2001 | Maxwell et al. |
| 6,087,182 | A | 7/2000 | Jeng et al. | 6,326,160 B1 | 12/2001 | Dunn et al. |
| 6,091,975 | A | 7/2000 | Daddona et al. | 6,329,161 B1 | 12/2001 | Heller et al. |
| 6,102,872 | A | 8/2000 | Doneen et al. | 6,330,464 B1 | 12/2001 | Colvin, Jr. et al. |
| 6,103,033 | A | 8/2000 | Say et al. | 6,335,203 B1 | 1/2002 | Patel et al. |
| 6,120,676 | A | 9/2000 | Heller et al. | 6,338,790 B1 | 1/2002 | Feldman et al. |
| 6,121,009 | A | 9/2000 | Heller et al. | 6,340,428 B1 | 1/2002 | Ikeda et al. |
| 6,121,050 | A | 9/2000 | Han | 6,342,364 B1 | 1/2002 | Watanabe et al. |
| 6,126,609 | A | 10/2000 | Keith et al. | 6,349,230 B1 | 2/2002 | Kawanaka |
| 6,128,519 | A | 10/2000 | Say | 6,358,752 B1 | 3/2002 | Durst et al. |
| 6,129,823 | A | 10/2000 | Hughes et al. | 6,377,894 B1 | 4/2002 | Deweese et al. |
| 6,134,461 | A | 10/2000 | Say et al. | 6,377,896 B1 | 4/2002 | Sato et al. |
| 6,136,549 | A | 10/2000 | Feistel | 6,379,513 B1 | 4/2002 | Huang et al. |
| 6,136,610 | A | 10/2000 | Polito et al. | 6,389,891 B1 | 5/2002 | D'Angelico et al. |
| 6,143,164 | A | 11/2000 | Heller et al. | 6,391,558 B1 | 5/2002 | Henkens et al. |
| 6,143,247 | A | 11/2000 | Sheppard, Jr. et al. | 6,391,645 B1 | 5/2002 | Huang et al. |
| 6,144,869 | A | 11/2000 | Berner et al. | 6,394,952 B1 | 5/2002 | Anderson et al. |
| 6,150,124 | A | 11/2000 | Riedel | 6,395,227 B1 | 5/2002 | Kiser et al. |
| 6,153,069 | A | 11/2000 | Pottgen et al. | 6,399,258 B2 | 6/2002 | O'Brien et al. |
| RE36,991 | E | 12/2000 | Yamamoto et al. | 6,401,532 B2 | 6/2002 | Lubbers |
| 6,156,051 | A | 12/2000 | Schraga | 6,413,213 B1 | 7/2002 | Essenpreis et al. |
| 6,156,173 | A | 12/2000 | Gotoh et al. | 6,413,395 B1 | 7/2002 | Bhullar et al. |
| 6,159,745 | A | 12/2000 | Roberts et al. | 6,413,410 B1 | 7/2002 | Hodges et al. |
| 6,162,611 | A | 12/2000 | Heller et al. | 6,420,128 B1 | 7/2002 | Ouyang et al. |
| 6,162,639 | A | 12/2000 | Douglas | 6,444,115 B1 | 9/2002 | Hodges et al. |
| 6,168,563 | B1 | 1/2001 | Brown | 6,447,657 B1 | 9/2002 | Bhullar et al. |
| 6,168,957 | B1 | 1/2001 | Matzinger et al. | 6,454,921 B1 | 9/2002 | Hodges et al. |
| 6,170,318 | B1 | 1/2001 | Lewis | 6,461,496 B1 | 10/2002 | Feldman et al. |
| 6,174,420 | B1 | 1/2001 | Hodges et al. | 6,475,360 B1 | 11/2002 | Hodges et al. |
| 6,175,752 | B1 | 1/2001 | Say et al. | 6,475,372 B1 | 11/2002 | Ohara et al. |
| 6,176,988 | B1 | 1/2001 | Kessler | 6,484,046 B1 | 11/2002 | Say et al. |
| 6,179,979 | B1 | 1/2001 | Hodges et al. | 6,485,923 B1 | 11/2002 | Yani et al. |
| 6,180,062 | B1 | 1/2001 | Naka et al. | 6,488,827 B1 | 12/2002 | Shartle |
| 6,180,416 | B1 | 1/2001 | Kurnik et al. | 6,489,133 B2 | 12/2002 | Phillips et al. |
| 6,193,873 | B1 | 2/2001 | Ohara et al. | 6,491,803 B1 | 12/2002 | Shen et al. |
| 6,197,040 | B1 | 3/2001 | LeVaughn et al. | 6,491,870 B2 | 12/2002 | Patel et al. |
| 6,200,773 | B1 | 3/2001 | Ouyang et al. | 6,501,976 B1 | 12/2002 | Sohrab |
| 6,201,607 | B1 | 3/2001 | Roth et al. | 6,503,381 B1 | 1/2003 | Gotoh et al. |
| 6,203,952 | B1 | 3/2001 | O'Brien et al. | 6,512,986 B1 | 1/2003 | Harmon |
| 6,206,282 | B1 | 3/2001 | Hayes, Sr. et al. | 6,514,718 B2 | 2/2003 | Heller et al. |
| 6,206,292 | B1 | 3/2001 | Robertz et al. | 6,514,769 B2 | 2/2003 | Lee |
| 6,218,571 | B1 | 4/2001 | Zheng et al. | 6,521,110 B1 | 2/2003 | Hodges et al. |
| 6,225,078 | B1 | 5/2001 | Ikeda et al. | 6,521,182 B1 | 2/2003 | Shartle et al. |
| 6,226,081 | B1 | 5/2001 | Fantone et al. | 6,525,330 B2 | 2/2003 | Paolini et al. |
| 6,241,862 | B1 | 6/2001 | McAleer et al. | 6,525,549 B1 | 2/2003 | Pollmann |
| 6,246,330 | B1 | 6/2001 | Nielsen | 6,526,298 B1 | 2/2003 | Khalil et al. |
| 6,246,966 | B1 | 6/2001 | Perry | 6,531,239 B2 | 3/2003 | Heller |
| 6,251,260 | B1 | 6/2001 | Heller et al. | 6,531,322 B1 | 3/2003 | Jurik et al. |
| 6,258,229 | B1 | 7/2001 | Winarta et al. | 6,538,735 B1 | 3/2003 | Duebendorfer et al. |
| 6,258,254 | B1 | 7/2001 | Miyamoto et al. | 6,540,890 B1 | 4/2003 | Bhullar et al. |
| 6,259,937 | B1 | 7/2001 | Schulman et al. | 6,540,891 B1 | 4/2003 | Stewart et al. |
| 6,261,519 | B1 | 7/2001 | Harding et al. | 6,541,266 B2 | 4/2003 | Modzelewski et al. |
| 6,262,749 | B1 | 7/2001 | Finger et al. | 6,544,474 B2 | 4/2003 | Douglas |
| 6,268,162 | B1 | 7/2001 | Phillips et al. | 6,549,796 B2 | 4/2003 | Sohrab |
| 6,270,637 | B1 | 8/2001 | Crismore et al. | 6,551,494 B1 | 4/2003 | Heller et al. |
| 6,271,044 | B1 | 8/2001 | Ballerstadt et al. | 6,555,061 B1 | 4/2003 | Leong et al. |
| 6,272,364 | B1 | 8/2001 | Kurnik | 6,558,528 B1 | 5/2003 | Matzinger |
| 6,277,641 | B1 | 8/2001 | Yager | 6,560,471 B1 | 5/2003 | Heller et al. |
| 6,281,006 | B1 | 8/2001 | Heller et al. | 6,562,625 B2 | 5/2003 | Modzelewski et al. |
| 6,284,125 | B1 | 9/2001 | Hodges et al. | 6,565,509 B1 | 5/2003 | Say et al. |
| 6,284,550 | B1 | 9/2001 | Carroll et al. | 6,565,738 B1 | 5/2003 | Henning et al. |

| | | | |
|---|---|---|---|
| 6,570,390 B2 | 5/2003 | Hirayama et al. | |
| 6,571,651 B1 | 6/2003 | Hodges | |
| 6,572,822 B2 | 6/2003 | Jurik et al. | |
| 6,574,425 B1 | 6/2003 | Weiss et al. | |
| 6,576,101 B1 | 6/2003 | Heller et al. | |
| 6,576,117 B1 | 6/2003 | Iketaki et al. | |
| 6,576,416 B2 | 6/2003 | Haviland et al. | |
| 6,576,461 B2 | 6/2003 | Heller et al. | |
| 6,591,125 B1 | 7/2003 | Buse et al. | |
| 6,592,744 B1 | 7/2003 | Hodges et al. | |
| 6,592,745 B1 | 7/2003 | Feldman et al. | |
| 6,594,514 B2 | 7/2003 | Berner et al. | |
| 6,599,406 B1 | 7/2003 | Kawanaka et al. | |
| 6,600,997 B2 | 7/2003 | Deweese et al. | |
| 6,605,200 B1 | 8/2003 | Mao et al. | |
| 6,605,201 B1 | 8/2003 | Mao et al. | |
| 6,607,658 B1 | 8/2003 | Heller et al. | |
| 6,616,819 B1 | 9/2003 | Liamos et al. | |
| 6,618,934 B1 | 9/2003 | Feldman et al. | |
| 6,623,501 B2 | 9/2003 | Heller et al. | |
| 6,627,057 B1 | 9/2003 | Bhullar et al. | |
| 6,632,349 B1 | 10/2003 | Hodges et al. | |
| 6,638,415 B1 | 10/2003 | Hodges et al. | |
| 6,638,716 B2 | 10/2003 | Heller et al. | |
| 6,645,359 B1 | 11/2003 | Bhullar et al. | |
| 6,645,368 B1 | 11/2003 | Beaty et al. | |
| 6,654,625 B1 | 11/2003 | Say et al. | |
| 6,656,702 B1 | 12/2003 | Yugawa et al. | |
| 6,660,141 B1 | 12/2003 | Minter et al. | |
| 6,676,995 B2 | 1/2004 | Dick et al. | |
| 6,689,411 B2 | 2/2004 | Dick et al. | |
| 6,743,635 B2 | 6/2004 | Neel et al. | |
| 7,018,843 B2 * | 3/2006 | Heller | 436/95 |
| 2001/0053535 A1 | 12/2001 | Ladisch et al. | |
| 2003/0109798 A1 | 6/2003 | Kermani | |

FOREIGN PATENT DOCUMENTS

| | | |
|---|---|---|
| EP | 0 010 456 | 4/1980 |
| EP | 0 034 049 | 8/1981 |
| EP | 0 057 110 | 8/1982 |
| EP | 0 073 056 A2 | 3/1983 |
| EP | 0 084 874 A1 | 8/1983 |
| EP | 0 101 880 | 3/1984 |
| EP | 0 132 790 A2 | 2/1985 |
| EP | 0 164 180 | 12/1985 |
| EP | 0 171 148 | 2/1986 |
| EP | 0 171 239 | 2/1986 |
| EP | 0 186 286 | 7/1986 |
| EP | 0 241 309 A2 | 10/1987 |
| EP | 0 287 883 | 10/1988 |
| EP | 0 359 831 | 3/1990 |
| EP | 0 206 218 B1 | 6/1991 |
| EP | 0 471 986 A2 | 2/1992 |
| EP | 0 255 291 B1 | 6/1992 |
| EP | 0 546 536 | 6/1993 |
| EP | 0 244 326 B1 | 8/1993 |
| EP | 0 537 761 A3 | 2/1994 |
| EP | 0 417 796 B1 | 11/1994 |
| EP | 0 213 343 B2 | 2/1995 |
| EP | 0 636 880 A2 | 2/1995 |
| EP | 0 640 832 | 3/1995 |
| EP | 0 651 250 A2 | 5/1995 |
| EP | 0 127 958 B2 | 4/1996 |
| EP | 0 732 406 A1 | 9/1996 |
| EP | 0 732 590 A2 | 9/1996 |
| EP | 0 383 322 B1 | 2/1997 |
| EP | 0 537 761 B1 | 8/1997 |
| EP | 0 840 122 A2 | 5/1998 |
| EP | 0 851 224 | 7/1998 |
| EP | 0 859 230 | 8/1998 |
| EP | 0 878 713 | 11/1998 |
| EP | 0 837 320 A3 | 12/1998 |
| EP | 0 887 421 A1 | 12/1998 |
| EP | 0 894 509 A2 | 2/1999 |
| EP | 0 470 649 B1 | 6/1999 |
| EP | 0 942 278 A2 | 9/1999 |
| EP | 0 964 059 | 12/1999 |
| EP | 0 230 472 B2 | 12/2000 |
| EP | 0 741 186 B1 | 10/2001 |
| EP | 0 958 495 | 11/2002 |
| EP | 0 876 506 | 7/2003 |
| GB | 2 295 676 | 6/1996 |
| JP | 01-291153 | 11/1989 |
| JP | 03-099254 | 4/1991 |
| JP | 04-121652 | 4/1992 |
| JP | 09-043242 | 2/1997 |
| JP | 10 332626 | 12/1998 |
| WO | WO 81/01794 | 7/1981 |
| WO | WO 83/00926 | 3/1983 |
| WO | WO 86/07632 | 12/1986 |
| WO | WO 89/09397 | 10/1989 |
| WO | WO 90/05293 | 5/1990 |
| WO | WO 92/01928 | 2/1992 |
| WO | WO 92/07655 | 5/1992 |
| WO | WO 92/15859 | 9/1992 |
| WO | WO 92/15861 | 9/1992 |
| WO | WO 92/15950 | 9/1992 |
| WO | WO 92/22669 | 12/1992 |
| WO | WO 93/09433 | 5/1993 |
| WO | WO 94/12950 | 6/1994 |
| WO | WO 94/16095 | 7/1994 |
| WO | WO 94/23295 | 10/1994 |
| WO | WO 94/28414 | 12/1994 |
| WO | WO 94/29705 | 12/1994 |
| WO | WO 95/03542 | 2/1995 |
| WO | WO 95/06919 | 3/1995 |
| WO | WO 95/07050 | 3/1995 |
| WO | WO 95/22597 | 8/1995 |
| WO | WO 96/04398 | 2/1996 |
| WO | WO 96/07908 | 3/1996 |
| WO | WO 96/13707 | 5/1996 |
| WO | WO 96/15454 | 5/1996 |
| WO | WO 96/33403 | 10/1996 |
| WO | WO 97/00441 | 1/1997 |
| WO | WO 97/02487 | 1/1997 |
| WO | WO 97/08544 | 3/1997 |
| WO | WO 97/16726 | 5/1997 |
| WO | WO 97/18465 | 5/1997 |
| WO | WO 97/29366 | 8/1997 |
| WO | WO 97/29847 | 8/1997 |
| WO | WO 97/30344 | 8/1997 |
| WO | WO 97/39341 | 10/1997 |
| WO | WO 97/39343 | 10/1997 |
| WO | WO 97/42882 | 11/1997 |
| WO | WO 97/42888 | 11/1997 |
| WO | WO 97/45719 | 12/1997 |
| WO | WO 98/05424 | 2/1998 |
| WO | WO 98/19153 | 5/1998 |
| WO | WO 98/19159 | 5/1998 |
| WO | WO 98/29740 | 7/1998 |
| WO | WO 98/35225 | 8/1998 |
| WO | WO 98/55853 | 12/1998 |
| WO | WO 98/57159 | 12/1998 |

OTHER PUBLICATIONS

Doss, J. D. et al, Medical Physics 1986, 13, 876-881.*
De Vries, P. M. J. M. et al, Medical and Biological Engineering and Computing, 1993, 31, 445-448.*
Yamakoshi, K.-I. et al, Medical and Biological Engineering and Computing, 1994, 32, Suppl., S99-S107.*
Singhal, P. et al, Analytical Chemistry 1997, 69, 1662-1668.*
Fare, T. L. et al, Biosensors & Bioelectronics 1998, 13, 459-470.*
Tjin, S. C. et al, Medical and Biological Engineering and Computing, 1998, 36, 467-470.*

U.S. 6,517,703, 02/2003, Beaty et al. (withdrawn).

Aoki et al., "Quantitative Analysis Of Reversible Diffusion Controlled Currents of Redox Soluble Species At Interdigitated Array Electrodes Under Steady-State Conditions", J. Electroanal. Chem. 256 (1988) 269-282.

Aoki et al., "Time-Dependence Of Diffusion-Controlled Currents Of A Soluble Redox Couple At Interdigitated Microarray Electrodes". J. Electronanal. Chem. 266 (1989) 11-20.

Bartlett, P.N. and Whitaker, R.G., "Electrochemical Immobilisation of Enzymes: Part. I. Theory", J. Electroanal Chem., 224 (1987) 27-35.

Bartlett, P.N. and Whitaker, R.G., "Electrochemical Immobilisation of Enzymes: Part II. Glucose Oxidase Immobilised In Poly-N-Methylpyrrole", J. Electroanal. Chem., 224 (1987) 37-48.

Beyer et al., "Development and Application of a New Enzyme Sensor Type Based on the EIS-Capacitance Structure for Bioprocess Control," Biosensors & Bioelectronics, vol. 9, pp. 17-21 (1994).

Bradley et al., "Kinetic Analysis of Enzyme Electrode Response," Anal. Chem., vol. 56, pp. 664-667 (1984).

Burke, et al., Improved-Accuracy Biosensor Strip For AccuChek™ Advantage®, Presented Orally At ACS Boston Meeting (~1993-1994).

Cardosi et al., "The Realization of Electron Transfer From Biological Molecules to Electrodes," Biosensors Fundamentals and Applications, chapt. 15 (Turner et al. eds., Oxford University Press. 1987).

Cass et al., "Ferrocene-Mediated Enzyme Electrode for Amperometric Determination of Glucose," Anal. Chem, vol. 56, pp. 667-671 (1984).

Chiba, K.; Ohsaka, T.; Ohnuki, Y.; and Oyama, N., "Electrochemical Preparation of A Ladder Polymer Containing Phenazine Rings." J. Eleectroanal Chemo., 219 (1987) 117-124.

Gebhardt, et al., "Electrocatalytic Glucose Sensor," Siemens Forsch-u, Entwickl-Ber. Bd., vol. 12, pp. 91-95 (1983).

Gregg, et al., "Cross-Lined Redox Gels Containing Glucose Oxidase For Amperometric Biosensor Applications", Anal. Chem. 1990, 62, 258-263.

Hintsche, R. et al., "Chip Biosensors On Thin-Film Metal Electrodes", Sensors and Actuators B. 4 (1991) 287-291.

Jin et al., "Application Of The Finite Analytic Numerical Method. Part 1. Diffusion Problems On Coplanar an dElevated Interdigitated Microarray Band Electrodes" J. Electroanal. Chem. 441 (1996) 29-36.

Kasapbasioglu et al., "An Impedance Based Ultra-Thin Platinum Island Film Glucose Sensor," Sensor and Actuators B. vol. 13-14, pp. 749-451 (1993).

Lambda Physik Brochure For LPX® Series.

Lee, et al., "A New Glucose Sensor Using Microporous Enzyme Membrane", Sensors and Actuators B, 3 (1991) 215-219.

Lifescan Guide Entitled "Quick Start" For The Onetouch® Ultra™ Blood Glucose Monitoring System.

Lifescan Owners's Booklet Entitled "The Comfort of Control".

Lifescan Product Brochure For Onetouch® Ultra™ Blood Glucose Monitoring System.

Lifescan Product Brochure For Onetouch® Ultra™ Test Strip.

Malitesta, et al., "Glucose Fast-Response Amperometric Sensor Based On Glucose Oxidase Immobilized In An Electpolymerized Poly (O-Phenylenediamine) Film", Anal. Chem. 1990, 62, 2735-2740.

Meier, et al., "Sensor and Sensor Elements Manufacturing: Laser Direct Patterning (LDP) for Reel to Reel Processing to generate High Throughput", LPKF Laser & Electronics AG, pp. 1-6.

Mell, et al., "A Model for the Amperometric Enzyme Electrode Obtained Through Digital Simulation and Applied to the immobilized Glucose Oxidase System," Analytical Chemistry, vol. 47, pp. 299-307 (Feb. 1975).

Mell et al., "Amperometric Response Enhancement of the Immobilized Glucose Oxidase Enzyme Electrode", Analytical Chemistry, vol. 48, pp. 1597-1601 (Sep. 1976).

Mohri, et al., "Characteristic Response of Electrochemical Nonlinearity to Taste Compounds with a Gold Electrode Modified with 4-Aminobenzenethiol," Bull, Chem. Soc. Jon., vol. 66, pp. 1328-1332 (1993).

Morris, et al., "An Electrochemical Capillary Fill Device for the Analysis of Glucose Incorporating Glucose Oxidase and Ruthenium (III) Hexamine as Mediator," Electroanalysis, vol. 4, pp. 1-9 (1992).

Muller et al., "Influence of Hematocrit and Platelet Count on Impedance and Reactivity of Whole Blood for Electrical Aggregometry," Journal of Pharmacological and Toxicological Methods, vol. 34, pp. 17-22 (1995).

Myland et al., "Membrane-Covered Oxygen Sensors: An Exact Treatment of the Switch-on Transient," Journal of the Electrochemical Society, vol. 131, pp. 1815-1823 (Aug. 1984).

Nishihara et al., "Interdigitated Array Electrode Diffusion Measurements in Donor/Acceptor Solutions in Polyether Electrolyte Solvents", Anal. Chem. 1991, 63, 2955-2960.

Niwa et al., "Electrochemical Behavior Of Reversible Redox Species At Interdigitated Array Electrodes With Different Geometries: Consideration Of Redox Cycling and Collection Efficiency" Anal. Chem. 62 (1990) 447-452.

Paeschke et al., "Properties of Interdigital Electrode Arrays With Different Geometries", Analytica Chimica Acta 305 (1995) 126-136.

Preidel et al. "Glucose Measurements by Electrocatalytic Sensor in the Extracorporeal Blood Circulation of a Sheep," Sensors and Actuators B, vol. 2, pp. 257-263 (1990).

Preidel et al., "In Vitro Measurements with Electrocatalytic Glucose Sensor in Blood," Biomed. Biochim. Acta, vol. 48, pp. 897-903 (1989).

Saeger et al., "Influence of Urea on the Glucose Measurement by Electrocatalytic Sensor in the Extracorporeal Blood Circulation of a Sheep," Biomed. Biochim. Acta, vol. 50, pp. 885-891 (1991).

Skladal, "Compensation of Temperature Variations Disturbing Performance of an Amperometric Biosensor for Continuous Monitoring," Sensors and Actuators B, Elsevier Sequoia S.A., Lausanne, CH, vol. 28, No. 1, Jul. 1, 1995, pp 59-62, XP004004390, ISSN: 0925-4005.

Talbott, et al., "A New Microchemical Approach to Amperometric Analysis," Microchemical Journal, vol. 37, pp. 5-12 (1988).

Tender et al., "Electrochemical Patterning of Self-Assembled Monolayers onto Microscopic Arrays of Gold Electrodes Fabricated by Laser Ablation," American Chemical Society, Langmuir, vol. 12, No. 23, pp. 5515-5518, (1996).

Williams et al., "Electrochemical-Enzymatic Analysis of Blood Glucose and Lactate." Analytical Chemistry, vol. 42, No. 1, pp. 118-121 (Jan. 1970).

Wollenberger et al., "Interdigitated Array Microelectrodes For The Determination Of Enzyme Activities", Analyst, Jun. 1994, 1245-1249.

Zhao, "Contributions of Suspending Medium to Electrical Impedance of Blood," Biochimica et Biophysica Acta, vol. 1201, pp. 179-185 (1994).

Zhao, "Electrical Impedance and Haematocrit of Human Blood with Various Anticoagulants," Physiol. Meas., vol. 14, pp. 299-307 (1993).

Bedell ("Admittance and Impedance Loci," Proc. Phys. Soc. London 14 327-336) 1895.

Pages 320-322 of Microsystem Design by Stephen Senturia, Kluwer Academic Publishers (2002).

* cited by examiner

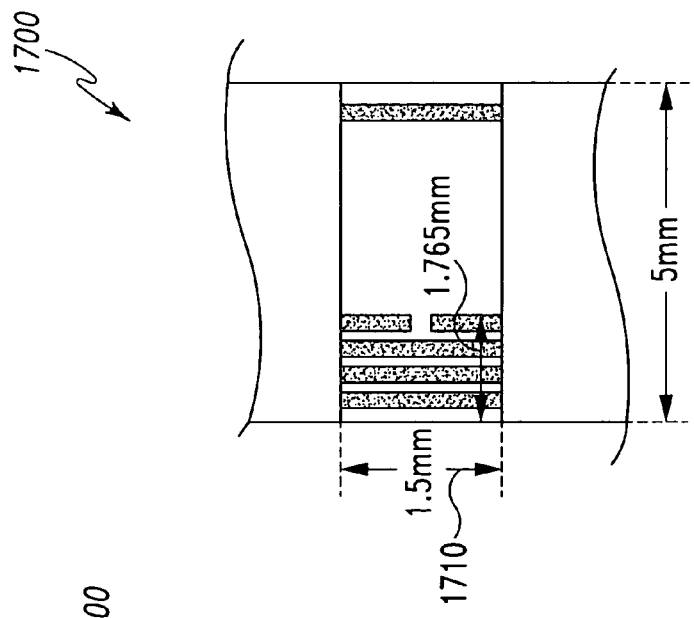
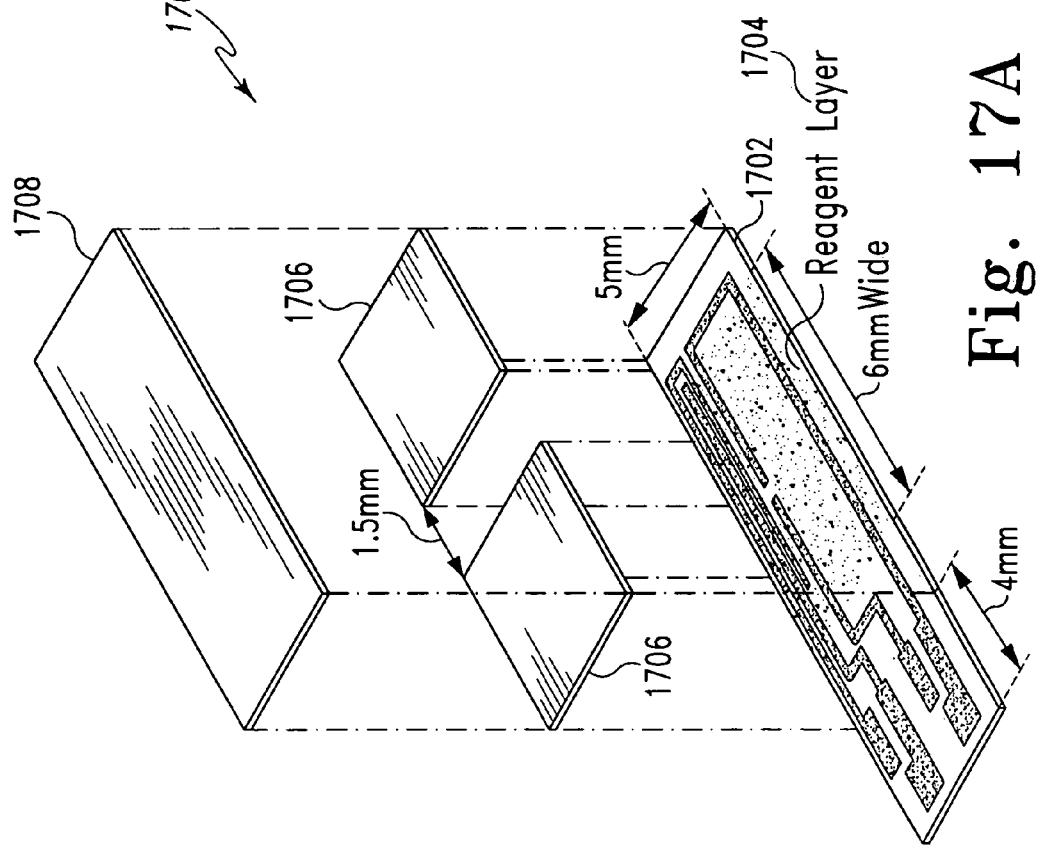
Fig. 17B
Fig. 17A

SYSTEM AND METHOD FOR DETERMINING A TEMPERATURE DURING ANALYTE MEASUREMENT

CROSS-REFERENCE TO RELATED APPLICATIONS

This application is a continuation-in-part of U.S. patent application Ser. No. 10/264,890, filed Oct. 4, 2002 now abandoned, which is a divisional application of U.S. patent application Ser. No. 09/530,171, filed Apr. 24, 2000 now U.S. Pat. No. 6,645,368, which is the U.S. national stage of International Patent Application Serial No. PCT/US98/27203, filed Dec. 21, 1998, which is a continuation-in-part of U.S. patent application Ser. No. 08/996,280, filed Dec. 22, 1997 (now abandoned), and claims priority benefit from each of these applications. This application also claims the benefit of U.S. Provisional Application No. 60/480,298, filed Jun. 20, 2003. The contents of each of these applications are hereby incorporated by reference herein.

TECHNICAL FIELD OF THE INVENTION

The present invention relates to a measurement method and apparatus for use in measuring concentrations of an analyte in a fluid. The invention relates more particularly, but not exclusively, to a method and apparatus which may be used for measuring the concentration of glucose in blood.

BACKGROUND OF THE INVENTION

Measuring the concentration of substances, particularly in the presence of other, confounding substances, is important in many fields, and especially in medical diagnosis. For example, the measurement of glucose in body fluids, such as blood, is crucial to the effective treatment of diabetes.

Diabetic therapy typically involves two types of insulin treatment: basal, and meal-time. Basal insulin refers to continuous, e.g. time-released insulin, often taken before bed. Meal-time insulin treatment provides additional doses of faster acting insulin to regulate fluctuations in blood glucose caused by a variety of factors, including the metabolization of sugars and carbohydrates. Proper regulation of blood glucose fluctuations requires accurate measurement of the concentration of glucose in the blood. Failure to do so can produce extreme complications, including blindness and loss of circulation in the extremities, which can ultimately deprive the diabetic of use of his or her fingers, hands, feet, etc.

Multiple methods are known for measuring the concentration of analytes in a blood sample, such as, for example, glucose. Such methods typically fall into one of two categories: optical methods and electrochemical methods. Optical methods generally involve reflectance or absorbance spectroscopy to observe the spectrum shift in a reagent. Such shifts are caused by a chemical reaction that produces a color change indicative of the concentration of the analyte. Electrochemical methods generally involve, alternatively, amperometric or coulometric responses indicative of the concentration of the analyte. See, for example, U.S. Pat. No. 4,233,029 to Columbus, U.S. Pat. No. 4,225,410 to Pace, U.S. Pat. No. 4,323,536 to Columbus, U.S. Pat. No. 4,008,448 to Muggli, U.S. Pat. No. 4,654,197 to Lilja et al., U.S. Pat. No. 5,108,564 to Szuminsky et al., U.S. Pat. No. 5,120,420 to Nankai et al., U.S. Pat. No. 5,128,015 to Szuminsky et al., U.S. Pat. No. 5,243,516 to White, U.S. Pat. No. 5,437,999 to Diebold et al., U.S. Pat. No. 5,288,636 to Pollmann et al., U.S. Pat. No. 5,628,890 to Carter et al., U.S. Pat. No. 5,682,884 to Hill et al., U.S. Pat. No. 5,727,548 to Hill et al., U.S. Pat. No. 5,997,817 to Crismore et al., U.S. Pat. No. 6,004,441 to Fujiwara et al., U.S. Pat. No. 4,919,770 to Priedel, et al., and U.S. Pat. No. 6,054,039 to Shieh, which are hereby incorporated in their entireties.

An important limitation of electrochemical methods of measuring the concentration of a chemical in blood is the effect of confounding variables on the diffusion of analyte and the various active ingredients of the reagent. For example, the geometry and state of the blood sample must correspond closely to that upon which the signal-to-concentration mapping function is based.

The geometry of the blood sample is typically controlled by a sample-receiving portion of the testing apparatus. In the case of blood glucose meters, for example, the blood sample is typically placed onto a disposable test strip that plugs into the meter. The test strip may have a sample chamber (capillary fill space) to define the geometry of the sample. Alternatively, the effects of sample geometry may be limited by assuring an effectively infinite sample size. For example, the electrodes used for measuring the analyte may be spaced closely enough so that a drop of blood on the test strip extends substantially beyond the electrodes in all directions. Ensuring adequate coverage of the measurement electrodes by the sample, however, is an important factor in achieving accurate test results. This has proven to be problematic in the past, particularly with the use of capillary fill spaces.

Other examples of limitations to the accuracy of blood glucose measurements include variations in blood composition or state (other than the aspect being measured). For example, variations in hematocrit (concentration of red blood cells), or in the concentration of other chemicals in the blood, can effect the signal generation of a blood sample. Variations in the temperature of blood samples is yet another example of a confounding variable in measuring blood chemistry.

Thus, a system and method are needed that accurately measure blood glucose, even in the presence of confounding variables, including variations in temperature, hematocrit, and the concentrations of other chemicals in the blood. A system and method are also needed to ensure adequate coverage of the measurement electrodes by the sample, particularly in capillary fill devices. A system and method are likewise needed that accurately measure an analyte in a fluid. It is an object of the present invention to provide such a system and method.

SUMMARY OF THE INVENTION

In one embodiment of the present invention, a method for measuring a temperature during a test for determining a concentration of a medically significant component of a biological fluid is disclosed, comprising the steps of a) providing a sensor having a reaction zone in which the biological fluid reacts with a reagent; and measuring a temperature in the reaction zone.

In another embodiment of the present invention, a method for measuring a temperature during a test for determining a concentration of a medically significant component of a biological fluid is disclosed, comprising the steps of a) applying a first signal having an AC component to the biological fluid; b) measuring a first AC response to the first signal; and using the first AC response to produce an indication of a temperature of the biological fluid.

In yet another embodiment of the present invention, a method of accounting for the effect of a temperature variation on a test for a glucose concentration of a biological fluid is disclosed comprising: a) applying at least a first test signal having an AC component to the biological fluid, the first test signal having a first frequency; b) measuring at least a first AC response to the first test signal; c) determining a temperature value of the biological fluid using the first AC response; and d) determining a temperature-corrected glucose concentration of the biological fluid based at least in part upon the temperature value.

In another embodiment of the present invention, a method of accounting for the effect of a temperature variation on a test for a glucose concentration of a biological fluid is disclosed comprising a) applying at least a first test signal having an AC component to the biological fluid, the first test signal having a first frequency; b) measuring at least a first AC response to the first test signal; c) determining a temperature value of the biological fluid using the first AC response; and d) determining a temperature-corrected glucose concentration of the biological fluid based at least in part upon the temperature value.

BRIEF DESCRIPTION OF THE DRAWINGS

The invention will be further described, by way of example only, with reference to the accompanying drawings, in which:

FIGS. 17A-B illustrate a second embodiment test strip of the present invention.

DETAILED DESCRIPTION OF THE PREFERRED EMBODIMENT

Figure 1:
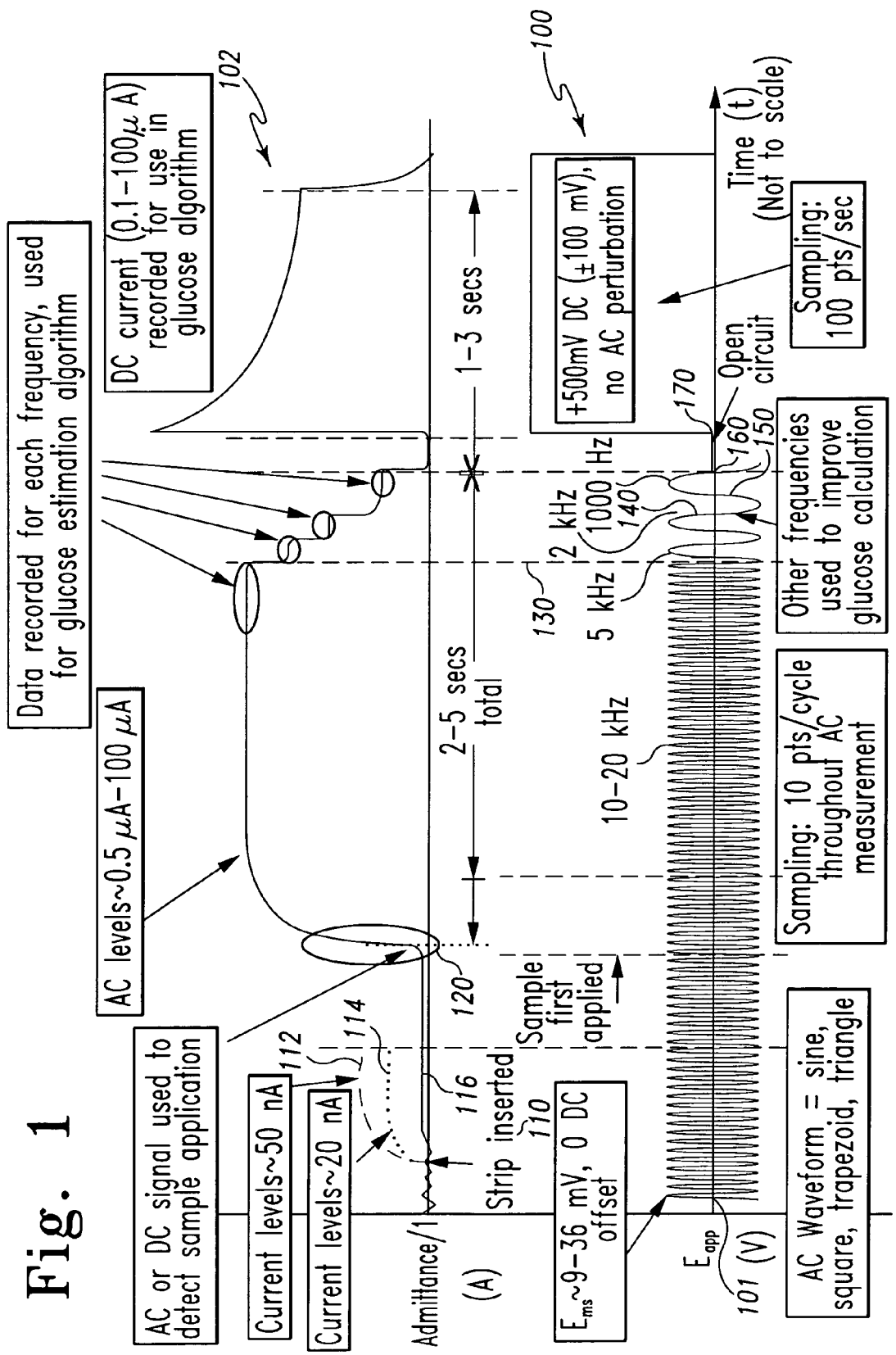
FIG. 1 is a diagram of a first embodiment excitation signal suitable for use in a system and method according to the present invention, having a serially-applied AC component and DC component.

For the purposes of promoting an understanding of the principles of the invention, reference will now be made to the embodiment illustrated in the drawings, and specific language will be used to describe that embodiment. It will nevertheless be understood that no limitation of the scope of the invention is intended. Alterations and modifications in the illustrated device, and further applications of the principles of the invention as illustrated therein, as would normally occur to one skilled in the art to which the invention relates are contemplated, are desired to be protected. In particular, although the invention is discussed in terms of a blood glucose meter, it is contemplated that the invention can be used with devices for measuring other analytes and other sample types. Such alternative embodiments require certain adaptations to the embodiments discussed herein that would be obvious to those skilled in the art.

The entire disclosure of U.S. provisional applications titled DEVICES AND METHODS RELATING TO ELECTROCHEMICAL BIOSENSORS (Ser. No. 60/480,243, filed Jun. 20, 2003) and DEVICES AND METHODS RELATING TO ANALYTE SENSOR (Ser. No. 60/480,397, Filed Jun. 20, 2003) are hereby incorporated by reference in their entireties.

A system and method according to the present invention permit the accurate measurement of an analyte in a fluid. In particular, the measurement of the analyte remains accurate despite the presence of interferants, which would otherwise cause error. For example, a blood glucose meter according to the present invention measures the concentration of blood glucose without error that is typically caused by variations in the temperature and the hematocrit level of the sample. The accurate measurement of blood glucose is invaluable to the prevention of blindness, loss of circulation, and other complications of inadequate regulation of blood glucose in diabetics. An additional advantage of a system and method according to the present invention is that measurements can be made much more rapidly and with much smaller sample volumes, making it more convenient for the diabetic person to measure their blood glucose. Likewise, accurate and rapid measurement of other analytes in blood, urine, or other biological fluids provides for improved diagnosis and treatment of a wide range of medical conditions.

It will be appreciated that electrochemical blood glucose meters typically (but not always) measure the electrochemical response of a blood sample in the presence of a reagent. The reagent reacts with the glucose to produce charge carriers that are not otherwise present in blood. Consequently, the electrochemical response of the blood in the presence of a given signal is intended to be primarily dependent upon the concentration of blood glucose. Secondarily, however, the electrochemical response of the blood to a given signal is dependent upon other factors, including hematocrit and temperature. See, for example, U.S. Pat. Nos. 5,243,516; 5,288, 636; 5,352,351; 5,385,846; and 5,508,171, which discuss the confounding effects of hematocrit on the measurement of blood glucose, and which are hereby incorporated by reference in their entireties. In addition, certain other chemicals can influence the transfer of charge carriers through a blood sample, including, for example, uric acid, bilirubin, and oxygen, thereby causing error in the measurement of glucose.

A preferred embodiment system and method for measuring blood glucose according to the present invention operates generally by using the signal-dependence of the contribution of various factors to the impedance (from which admittance and phase angle may be derived) of a blood sample. Because the contribution of various factors to the impedance of a blood sample is a function of the applied signal, the effects of confounding factors (that is, those other than the factors sought to be measured) can be substantially reduced by measuring the impedance of the blood sample to multiple signals. In particular, the effects of confounding factors, (primarily temperature and hematocrit, but also including chemical interferants such as oxygen), contribute primarily to the resistivity of the sample, while the glucose-dependent reaction contributes primarily to the capacitance. Thus, the effects of the confounding factors can be eliminated by measuring the impedance of the blood sample to an AC excitation, either alone or in combination with a DC excitation. The impedance (or the impedance derived admittance and phase information) of the AC signal is then used to correct the DC signal or AC derived capacitance for the effects of interferants.

It will be appreciated that measurements at sufficiently high AC frequencies are relatively insensitive to the capacitive component of the sample's impedance, while low frequency (including DC) measurements are increasingly (with decreasing frequency) sensitive to both the resistive and the capacitive components of the sample's impedance. The resistive and capacitive components of the impedance can be better isolated by measuring the impedance at a larger number of frequencies. However, the cost and complexity of the meter increases as the number of measurements increases and the number of frequencies that need to be generated increases. Thus, in the presently preferred embodiment, the impedance may be measured at greater than ten frequencies, but preferably at between two and ten frequencies, and most preferably at between two and five frequencies.

As used herein, the phrase "a signal having an AC component" refers to a signal which has some alternating potential (voltage) portions. For example, the signal may be an "AC signal" having 100% alternating potential (voltage) and no DC portions; the signal may have AC and DC portions separated in time; or the signal may be AC with a DC offset (AC and DC signals superimposed).

Sample Measurement with Successive AC and DC Signals

FIG. 1 illustrates a preferred embodiment excitation signal suitable for use in a system and method according to the present invention, indicated generally at 100, in which DC excitation and four frequencies of AC excitation are used. FIG. 1 also illustrates a typical response to the excitation when the excitation is applied to a sample of whole blood mixed with an appropriate reagent, the response indicated generally at 102. A relatively high frequency signal is applied, starting at time 101. In the preferred embodiment the frequency is between about 10 kHz and about 20 kHz, and has an amplitude between about 12.4 mV and about 56.6 mV. A frequency of 20 kHz is used in the example of FIG. 1. Those skilled in the art will appreciate that these values may be optimised to various parameters such as cell geometry and the particular cell chemistry.

At time 110 a test strip is inserted into the meter and several possible responses to the insertion of the test strip into the glucose meter are shown. It will be appreciated that the test strip may also be inserted before the excitation signal 100 is initiated (i.e. before time 101); however, the test strip itself may advantageously be tested as a control for the suitability of the strip. It is therefore desirable that the excitation signal 100 be initiated prior to test strip insertion. For example, relatively large current leakage, as shown at 112, may occur if the strip is wet, either because the test strip was pre-dosed, or due to environmental moisture. If the test strip has been pre-dosed and permitted to largely or completely dry out, an intermediate current leakage may occur, as shown at 114. Ideally, insertion of the test strip will cause no or negligible leakage current due to an expected absence of charge carriers between the test electrodes, as shown at 116. Measured current leakage above a predetermined threshold level will preferably cause an error message to be displayed and prevent the test from continuing.

Once a suitable test strip has been inserted, the user doses the strip, as shown at time 120. While the blood sample is covering the electrodes the current response will rapidly increase, as the glucose reacts with the reagent and the contact area increases to maximum. The response current will reach a stable state, which indicates the impedance of the sample at this frequency. Once this measurement is made and recorded by the test meter, the excitation frequency is then stepped down to about 10 kHz in the preferred embodiment, as shown at time 130. Another measurement is made and recorded by the test meter, and the frequency is stepped down to about 2 kHz in the preferred embodiment, as shown at 140. A third measurement is made and recorded by the test meter at this frequency. A fourth measurement is made at about 1 kHz in the preferred embodiment, as shown at 150. In the preferred embodiment, measurements are taken at regular intervals (e.g. 10 points per cycle). It will be appreciated that the stable state response may be measured as current or voltage (preferably both magnitude and phase) and the impedance and/or admittance can be calculated therefrom. Although the present specification and claims may refer alternately to the AC response as impedance or admittance (magnitude and/or phase), resistance, conductivity, current or charge, and to the DC response as current, charge, resistance or conductivity, those skilled in the art will recognize that these measures are interchangeable, it only being necessary to adjust the measurement and correction mathematics to account for which measure is being employed. In the preferred embodiment, the test meter applies a voltage to one electrode and measures the current response at the other electrode to obtain both the AC and DC response.

In certain alternative embodiments measurements are made at fewer or more frequencies. Preferably measurements are made at at least two AC frequencies at least an order of magnitude apart. If more than two AC frequencies are used, then it is preferable that the highest and lowest frequencies be at least an order of magnitude apart.

It will be appreciated that various waveforms may be used in an AC signal, including, for example, sinusoidal, trapezoidal, triangle, square and filtered square. In the presently preferred embodiment the AC signal has a filtered square waveform that approximates a sine wave. This waveform can be generated more economically than a true sine wave, using a square wave generator and one or more filters.

Once all four AC measurements are made, the signal is preferably briefly reduced to zero amplitude, as shown at 160. The DC excitation is then begun, as shown at 170. The amplitude of the DC excitation is advantageously selected based on the reagent being used, in order to maximise the resulting response or response robustness. For example, if ferricyanide is being used in a biamperometry system, the DC amplitude is preferably about 300 mV. For another example, if a nitrosoaniline derivative is being used in a biamperometry system, the DC amplitude is preferably about 500-550 mV. In the alternative, if a third reference electrode is used, the DC applitude is preferably 600 mV (versus the silver/silver chloride reference electrode) for ferricyanide, and 40-100 mV (versus the silver/silver chloride reference electrode) for nitrosoaniline derivative. During DC excitation, measurements are preferably made at a rate of 100 pts/sec. The current response will follow a decay curve (known as a Cottrell curve), as the reaction is limited by the diffusion of unreacted glucose next to the working electrode. The resulting stable-state amplitude (measured or projected) is used to determine a glucose estimation of the sample, as is known in the art. A corrected estimation is then determined that corresponds more closely to the concentration of glucose in the blood, by using the impedance of the sample to the AC signal to correct for the effects of interferants, as explained in greater detail hereinbelow.

It will be appreciated that a method according to the present invention may also be used to measure the concentration of other analytes and in other fluids. For example, a method according to the present invention may be used to measure the concentration of a medically significant analyte in urine, saliva, spinal fluid, etc. Likewise, by appropriate selection of reagent a method according to the present invention may be adapted to measure the concentration of, for example, lactic acid, hydroxybutyric acid, etc.

Sample Measurement with Simultaneously Applied AC and DC Signals

Figure 2:
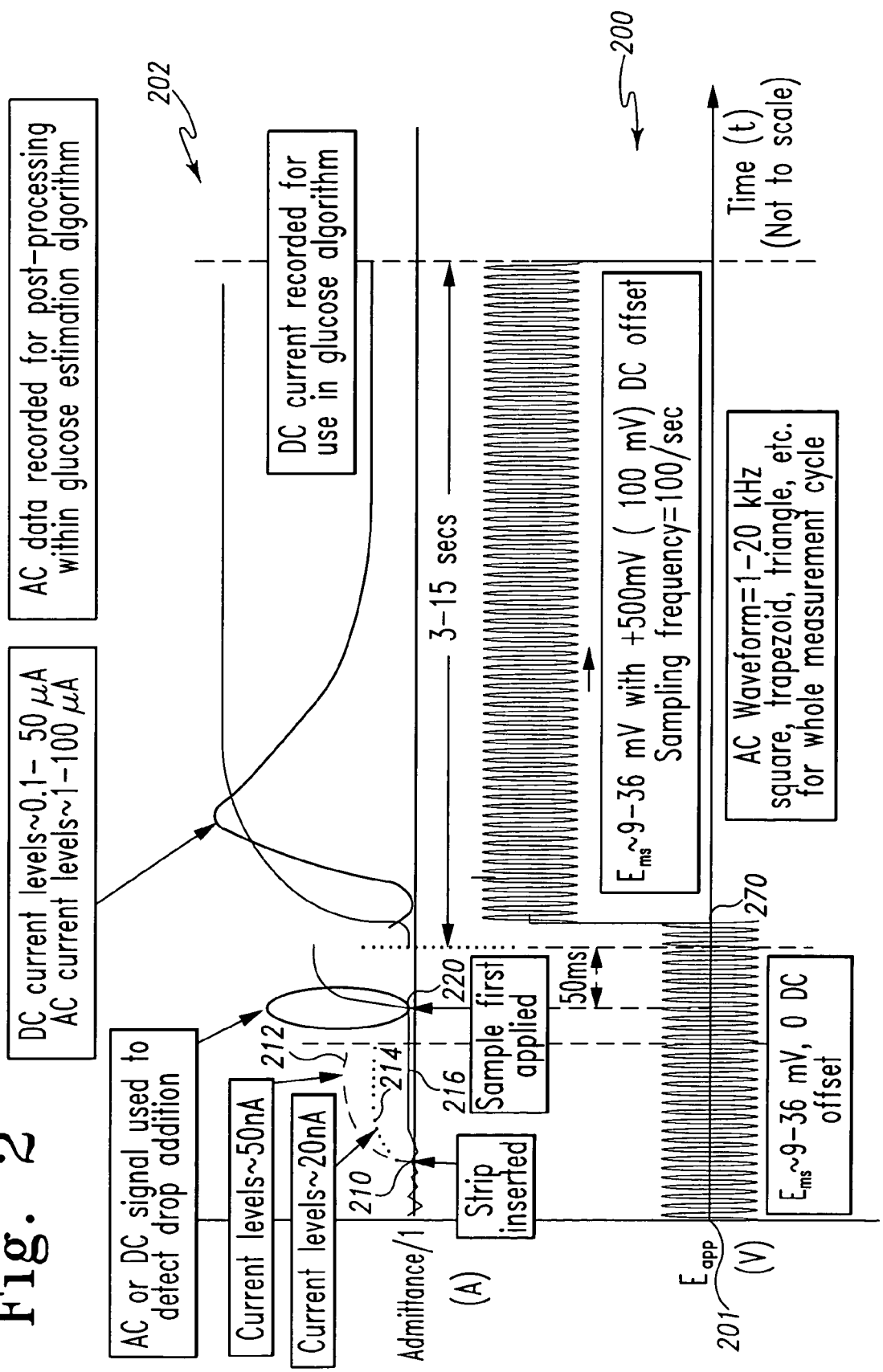
FIG. 2 is a diagram of a second embodiment excitation signal suitable for use in a system and method according to the present invention, having a simultaneously-applied AC component and DC component.

It will be appreciated that at least some of the applied DC and AC components can also be applied simultaneously. FIG. 2 illustrates an excitation signal suitable for use in a system and method according to the present invention in which some of the AC and DC components are applied simultaneously, indicated generally at 200, and having corresponding events numbered correspondingly to FIG. 1 (so, for example, the signal 200 is initiated at time 201, and a strip is inserted at time 210, etc.). As with the signal 100, the signal 200 has a frequency of about 10-20 kHz and an amplitude of about 12.4-56.6 mV. However, after the strip has been dosed, as shown at time 220, a DC offset is superimposed, as shown at 270. Typical AC and DC responses are shown in FIG. 2. The AC and DC responses are measured simultaneously and mathematically deconvoluted and used to determine the impedance (admittance magnitude and phase) and the amperometric or coulometric response.

A system for measuring blood glucose according to the present invention advantageously employs a blood glucose meter and test strips generally similar to those used in prior art systems, such as those commercially available from Roche Diagnostics, and such as are described in U.S. Pat. Nos. 6,270,637; and 5,989,917, which are hereby incorporated in their entireties. These test strips provide apparati having a sample cell in which the blood sample is received for testing, and electrodes disposed within the sample cell through which the excitation signal is provided and the measurements are made. Those skilled in the art will appreciate that these test strips and meters may advantageously be used for the measurement of glucose in blood, but that other apparati may be more suitable for the measurement of other analytes or other biological fluids when practising the present invention.

A suitable glucose meter may be adapted from such known meters by the addition of electronic circuitry that generates and measures signals having AC and DC components, such as those described hereinabove, and by being programmed to correct the DC measurement using the AC measurement(s), as described in greater detail hereinbelow. It will be appreciated that the specific geometry and chemistry of the test strips can cause variations in the relationships between the concentration of glucose, hematocrit, and temperature, and the impedance of a sample. Thus, a given combination of test strip geometry and chemistry must be calibrated, and the meter programmed with the corresponding algorithm. The present invention comprehends the application of excitation signals in any order and combination. For example, the present invention comprehends the application of 1) AC only, 2) AC then DC, 3) AC then DC then AC, 4) DC then AC, and 5) AC with a DC offset, just to name a few of the possible permutations.

The use of the complex AC impedance measurement data to correct for the effects of interferants on the DC measurement is advantageously illustrated by the following series of examples. These examples illustrate how the principles of the present invention can facilitate improvements in accuracy and test speed when measuring the concentration of an analyte in a test specimen. Although the following examples deal with correcting for the interfering effects of hematocrit and temperature on blood glucose determinations, those skilled in the art will recognize that the teachings of the present invention are equally useful for correcting for the effects of other interferants in both blood glucose measurements and in the measurement of other analytes. Furthermore, the present specification and claims refer to steps such as "determine the hematocrit value" and "determine the temperature," etc. To use the hematocrit value as an example, it is intended that such statements include not only determining the actual hematocrit value, but also a hematocrit correction factor vs. some nominal point. In other words, the process may never actually arrive at a number equal to the hematocrit value of the sample, but instead determine that the sample's hematocrit differs from a nominal value by a certain amount. Both concepts are intended to be covered by statements such as "determine the hematocrit value."

EXAMPLE 1

DC-Only Measurement Dose Response Study

Figure 3:
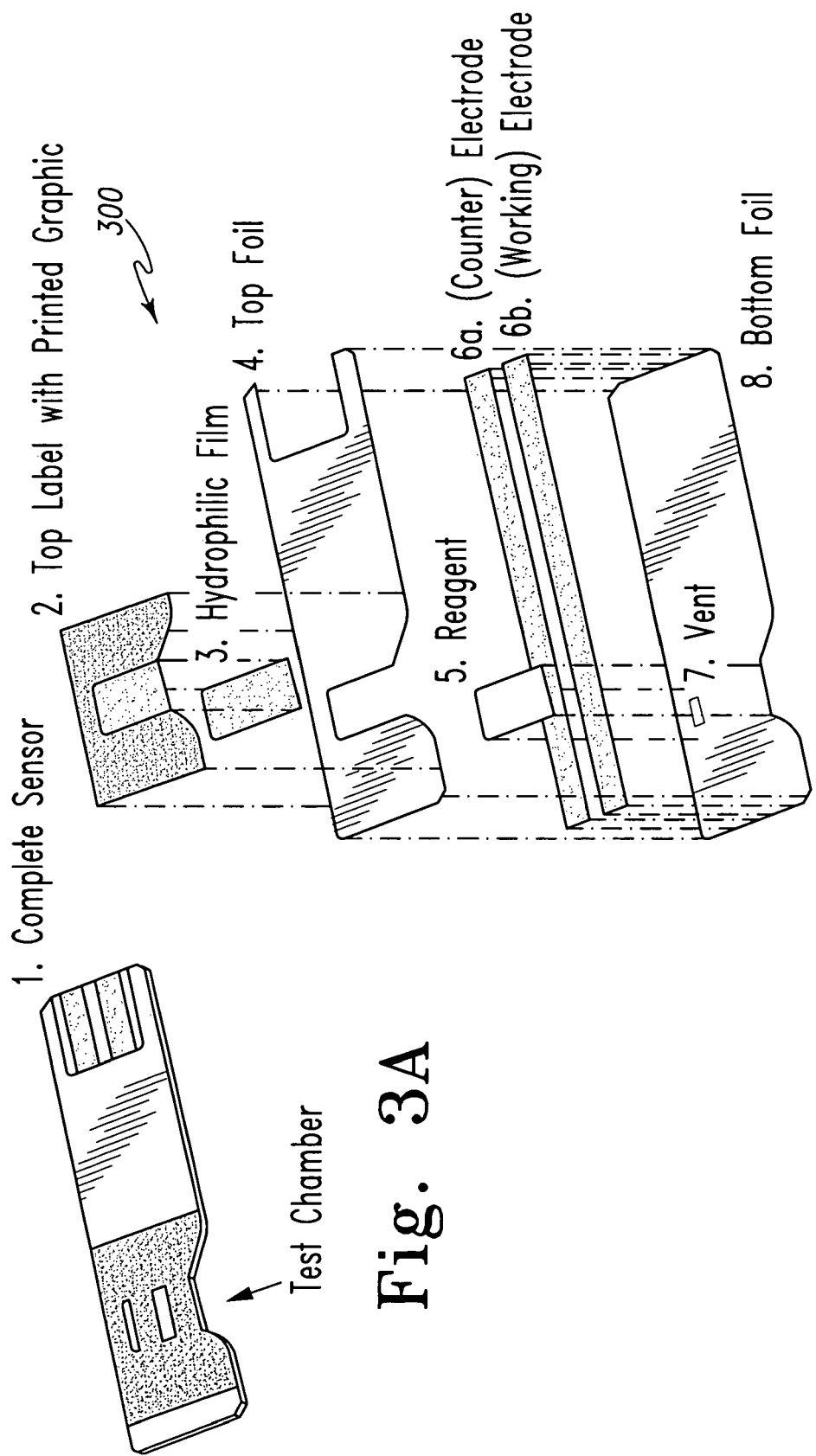
FIGS. 3A-B illustrate a first embodiment test strip of the present invention.

The measurements made in Example 1 were achieved using the test strip illustrated in FIGS. 3A-B and indicated generally at 300. The test strip 300 includes a capillary fill space containing a relatively thick film reagent and working and counter electrodes, as described in U.S. Pat. No. 5,997,817, which is hereby incorporated by reference. The test strip 300 is commercially available from Roche Diagnostics Corporation (Indianapolis, Ind.) under the brand name Comfort Curve®. The ferricyanide reagent used had the composition described in Tables I and II.

TABLE I

Reagent Mass Composition - Prior to Dispense and Drying

| | Component | % w/w | Mass for 1 kg |
|---|---|---|---|
| solid | Polyethylene oxide (300 kDa) | 0.8400% | 8.4000 g |
| solid | Natrosol 250M | 0.0450% | 0.4500 g |
| solid | Avicel RC-591F | 0.5600% | 5.6000 g |
| solid | Monobasic potassium phosphate (annhydrous) | 1.2078% | 12.0776 g |
| solid | Dibasic potassium phosphate (annhydrous) | 2.1333% | 21.3327 g |
| solid | Sodium Succinate hexahydrate | 0.6210% | 6.2097 g |
| solid | Quinoprotein glucose dehydrogenase (EnzC#: 1.1.99.17) | 0.1756% | 1.7562 g |
| solid | PQQ | 0.0013% | 0.0125 g |
| solid | Trehalose | 2.0000% | 20.0000 g |
| solid | Potassium Ferricyanide | 5.9080% | 59.0800 g |
| solid | Triton X-100 | 0.0350% | 0.3500 g |
| solvent | Water | 86.4731% | 864.7313 g |
| | % Solids | | 0.1352687 |
| | Target pH | | 6.8 |
| | Specific Enzyme Activity Used (U/mg) | | 689 DCIP |
| | Dispense Volume per Sensor | | 4.6 mg |

TABLE II

Reagent Layer Composition - After Drying

| | Component | % w/w | Mass per Sensor |
|---|---|---|---|
| solid | Polyethylene oxide (300 kDa) | 6.2099% | 38.6400 ug |
| solid | Natrosol 250M | 0.3327% | 2.0700 ug |
| solid | Avicel RC-591F | 4.1399% | 25.7600 ug |
| solid | Monobasic potassium phosphate (annhydrous) | 8.9286% | 55.5568 ug |
| solid | Dibasic potassium phosphate (annhydrous) | 15.7706% | 98.1304 ug |
| solid | Sodium Succinate hexahydrate | 4.5906% | 28.5646 ug |

TABLE II-continued

Reagent Layer Composition - After Drying

| | Component | % w/w | Mass per Sensor |
|---|---|---|---|
| solid | Quinoprotein glucose dehydrogenase (EnzC#: 1.1.99.17) | 1.2983% | 8.0784 ug |
| solid | PQQ | 0.0093% | 0.0576 ug |
| solid | Trehalose | 14.7854% | 92.0000 ug |
| solid | Potassium Ferricyanide | 43.6760% | 271.7680 ug |
| solid | Triton X-100 | 0.2587% | 1.6100 ug |

Figure 4:
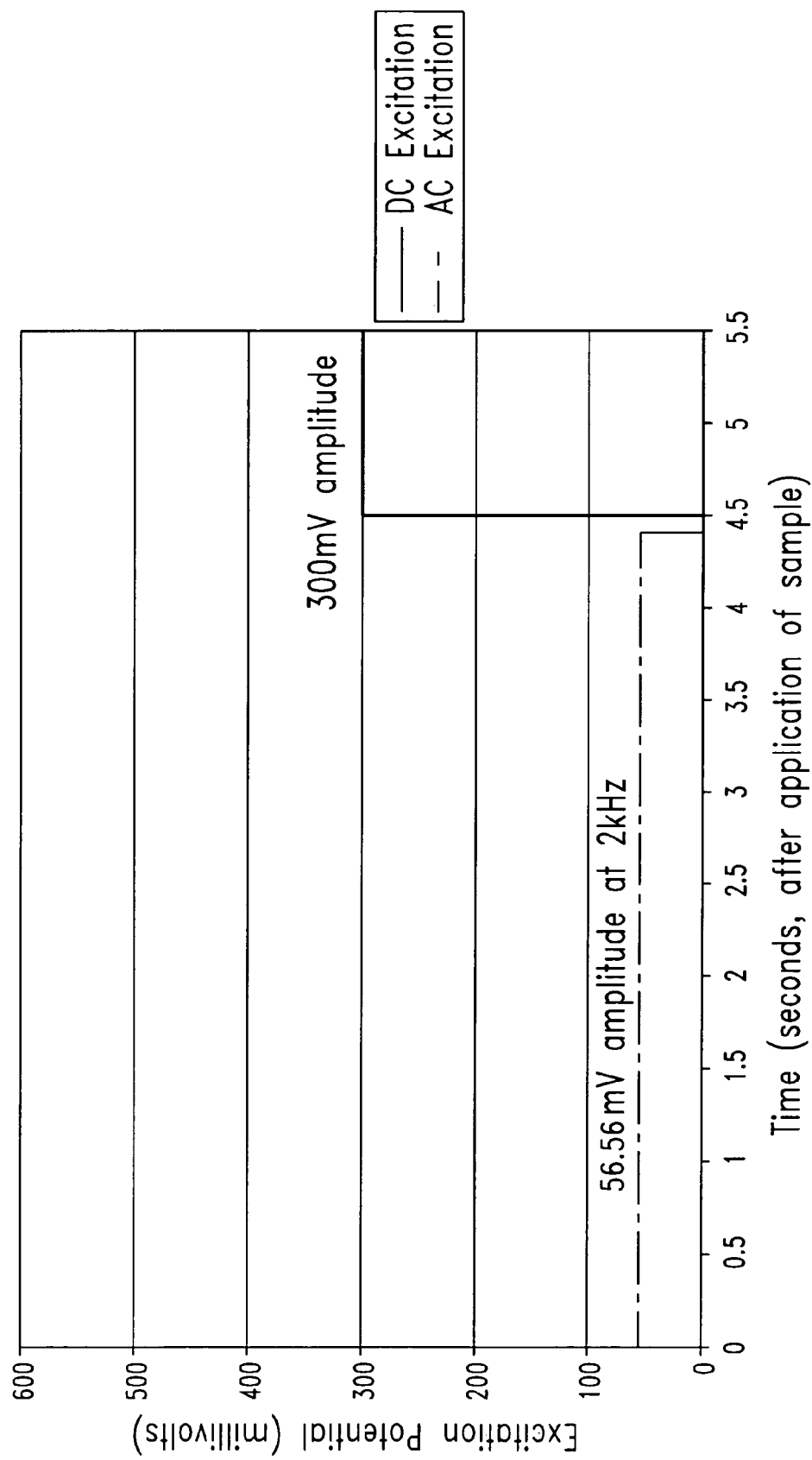
FIG. 4 is a diagram of an excitation signal utilized in the test of Example 1.

In the measurements, blood samples were applied to test strip 300 and the excitation potentials illustrated in FIG. 4 were applied to the electrodes. The excitation comprised a 2 kHz 40 $mV_{rms}$ (56.56 mV peak) AC signal applied between 0 seconds and approximately 4.5 seconds after sample application, followed by a 300 mV DC signal applied thereafter. For the calculations of this example, however, only the DC measurement data was analyzed.

In order to determine the minimum needed DC excitation time, a "dose response" study was performed, in which glycollyzed (glucose depleted) blood was divided into discrete aliquots and controlled levels of glucose were added to obtain five different known levels of glucose in the blood samples. The resulting DC current profile was then examined as two parameters were varied. The first parameter was the Incubation Time, or the time between the detection of the blood sample being applied to the test strip 300 and the application of the DC potential to the test strip 300. The second parameter to be varied was the Read Time, or the time period after application of the DC potential and the measurement of the resulting current. The length of time between detection of the blood sample being applied to the test strip to the taking of the last measurement used in the concentration determination calculations is the Total Test Time. In this study, therefore, the sum of the Incubation Time and the Read Time is the Total Test Time. The results of this study are illustrated in FIGS. 5 and 6.

Figure 5:
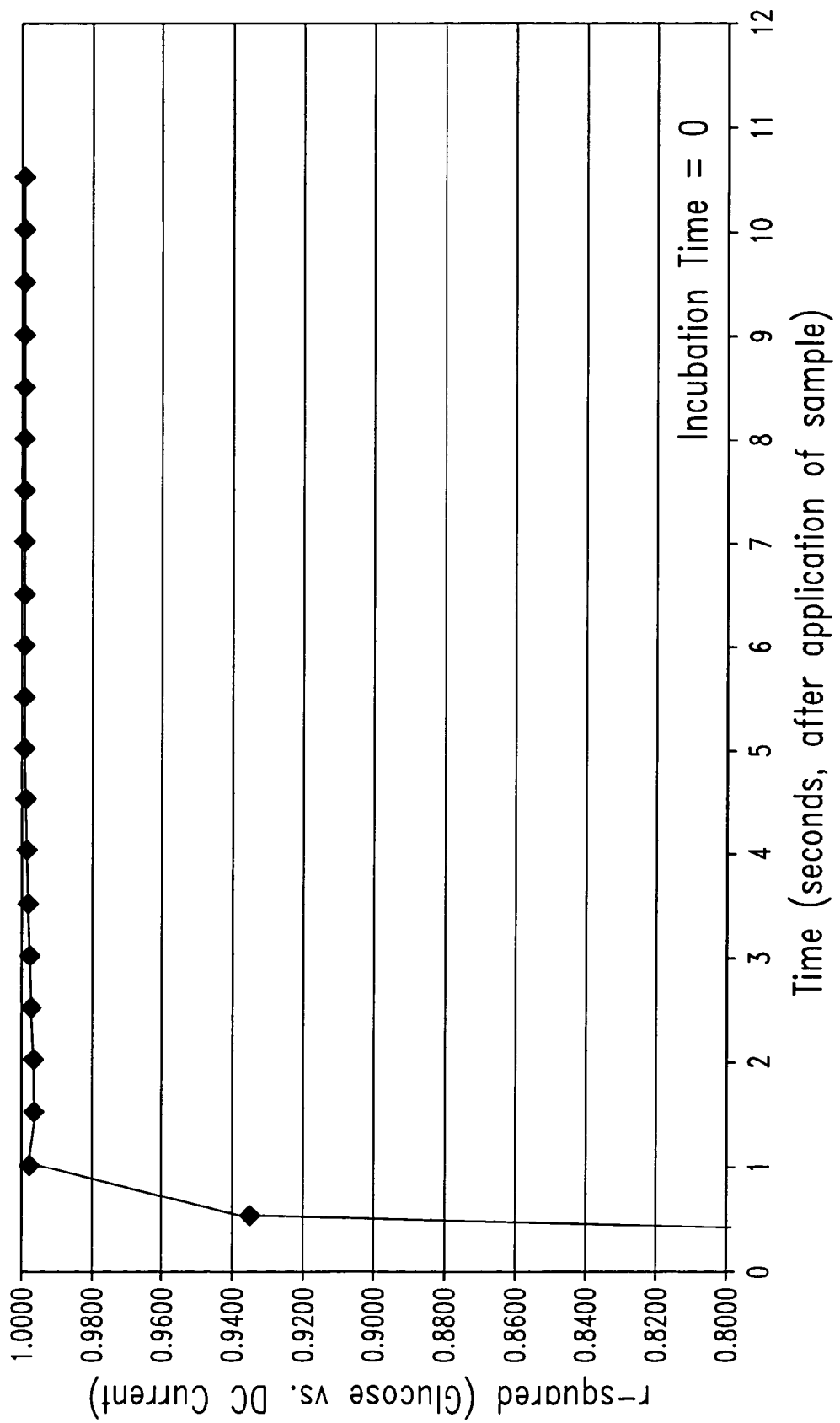
FIG. 5 is a plot of the correlation coefficient $r^2$ (glucose vs. DC current) versus Read Time for the test of Example 1 with no incubation time.
Figure 6:
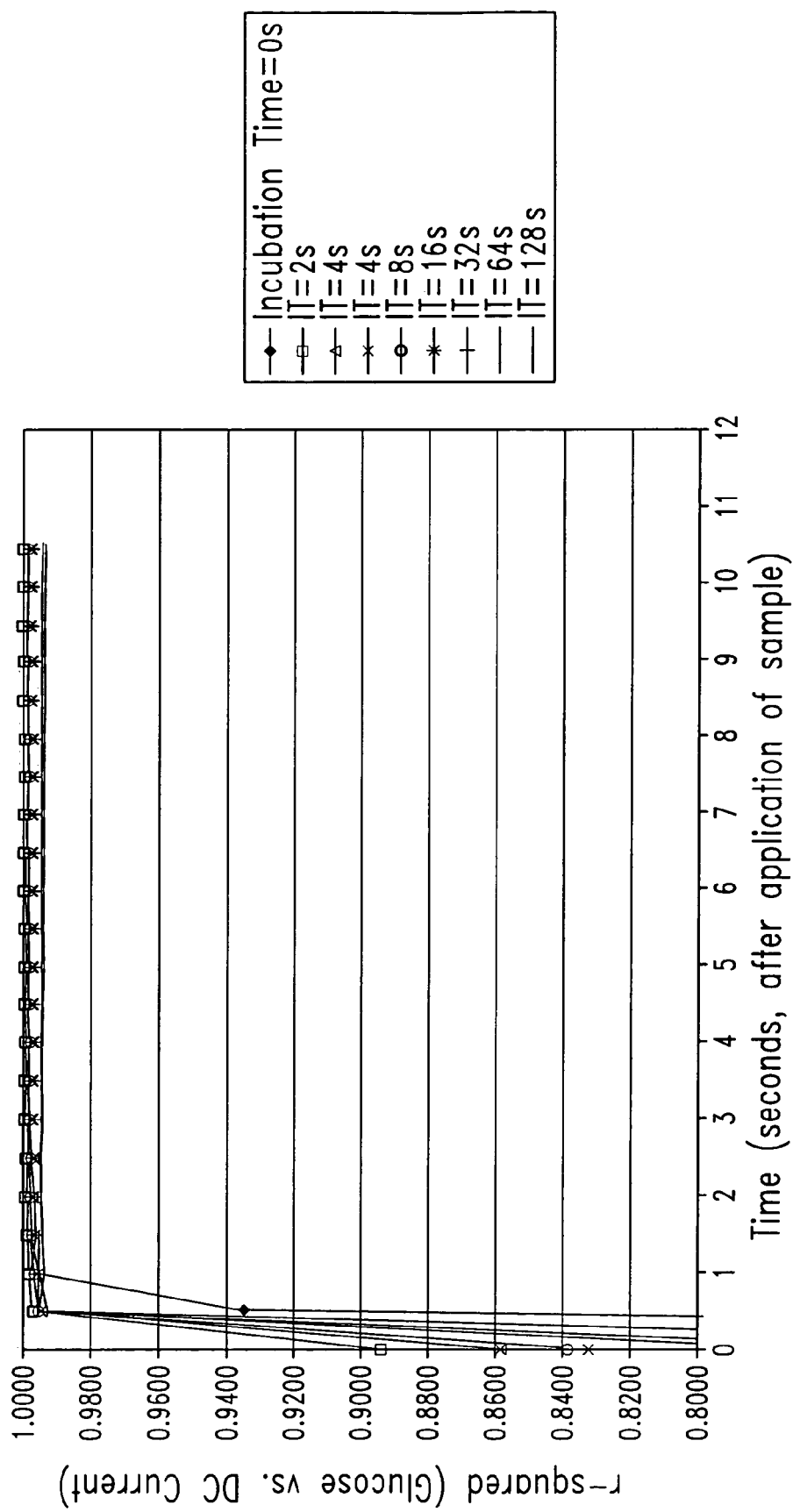
FIG. 6 is a plot of the correlation coefficient $r^2$ (glucose vs. DC current) versus Read Time for the test of Example 1 with varying incubation time.

In FIG. 5, the DC response was measured with no incubation time (Read Time=Total Test Time). FIG. 5 plots the correlation coefficient $r^2$ versus Read Time. As can be seen, the correlation exceeds 0.95 within 1.0 second. In FIG. 6, the DC response was measured with varying Incubation Time. When an Incubation Time is provided (even an Incubation Time as short as two (2) seconds), the $r^2$ value rose to over 0.99 in 0.5 seconds or less after application of the DC potential.

The barrier to implementation of such fast test times in a consumer glucose test device, however, is the variation from blood sample to blood sample of the level of interference from the presence of blood cells in the sample. The hematocrit (the percentage of the volume of a blood sample which is comprised of cells versus plasma) varies from individual to individual. The interference effect of hematocrit on such measurements is fairly complex. In the tests of Example 1, however, all samples contained the same level of hematocrit. With no variable hematocrit influence at the different glucose levels, the hematocrit term cancels out in the correlation figures.

EXAMPLE 2

Combined AC and DC Measurement of Capillary Blood Samples

The measurements made in Example 2 were also achieved using the test strip illustrated in FIGS. 3A-B and indicated generally at 300. As described above, the test strip 300 includes a capillary fill space containing a relatively thick film reagent and working and counter electrodes, as described in U.S. Pat. No. 5,997,817, which is hereby incorporated herein by reference.

In the measurements, capillary blood samples from various fingerstick donors were applied to test strip 300 and the excitation potentials illustrated in FIG. 4 were applied to the electrodes. The excitation comprised a 2 kHz 40 mV$_{rms}$ AC signal applied between 0 seconds and approximately 4.5 seconds after sample application, followed by a 300 mV DC signal applied thereafter.

Figure 7:
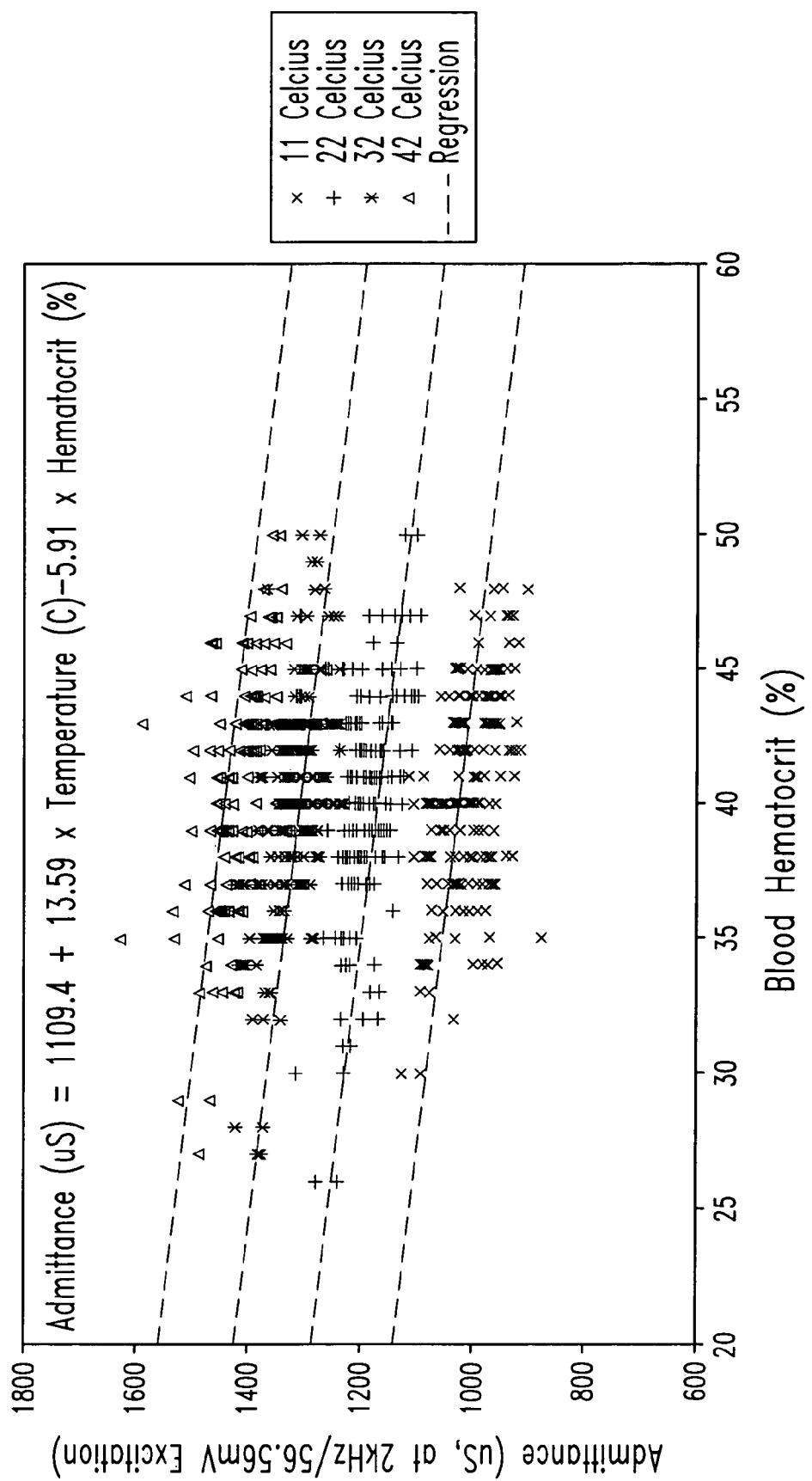
FIG. 7 is a plot of AC admittance versus hematocrit for the test of Example 2.

In this Example 2, the AC response of the sample was derived as admittance (the inverse of impedance). The admittance response is proportional to the hematocrit level of the sample in a temperature dependent manner. The relationship between admittance, hematocrit and testing temperature is illustrated in FIG. 7. The data used for the admittance charted in FIG. 7 is the last admittance measurement made for each sample during the AC portion of the excitation illustrated in FIG. 4.

Regression analysis of this data allows admittance, hematocrit and temperature to be related according to the following formula:

$$H_{est} = c_0 + c_1 Y_{2\,kHz} + c_2 dT \qquad \text{(Equation 1)}$$

Using this relationship to predict the blood hematocrit is accomplished using test temperature data reported by the temperature sensor in the meter and the measured admittance. In Equation 1, $c_0$, $c_1$ and $c_2$ are constants, dT is the deviation in temperature from a center defined as "nominal" (24° C. for example), and $H_{est}$ is the estimated deviation in hematocrit from a similar "nominal" value. For the present purposes, the actual hematocrit value is not necessary, and it is generally preferred to produce a response which is proportionate but centers around a nominal hematocrit. Thus, for a 70% hematocrit, the deviation from a nominal value of 42% would be 28%, while conversely for a 20% hematocrit the deviation from that same nominal value would be −22%.

By using the AC admittance measurement to estimate the hematocrit level using Equation 1, the accuracy of the DC glucose response can be greatly improved by combining the estimated hematocrit, temperature and DC response to correct for the hematocrit interference in the DC response as follows:

$$\text{PRED} = (a_0 + hct_1 H_{est} + hct_2 H_{est}^2 + tau_1 dT + tau_2 dT^2) + (a_1 DC)(1 + hct_3 H_{est} + hct_4 H_{est}^2)(1 + tau_3 dT + tau_4 dT^2) \qquad \text{(Equation 2)}$$

where DC is the measured glucose current response to the applied DC signal and PRED is the compensated (predicted) glucose response corrected for the effects of hematocrit and temperature. The constants ($a_0$, $hct_1$, $hct_2$, $tau_1$, $tau_2$, $a_1$, $hct_3$, $hct_4$, $tau_3$ and $tau_4$) in Equation 2 can be determined using regression analysis, as is known in the art.

Figure 8:
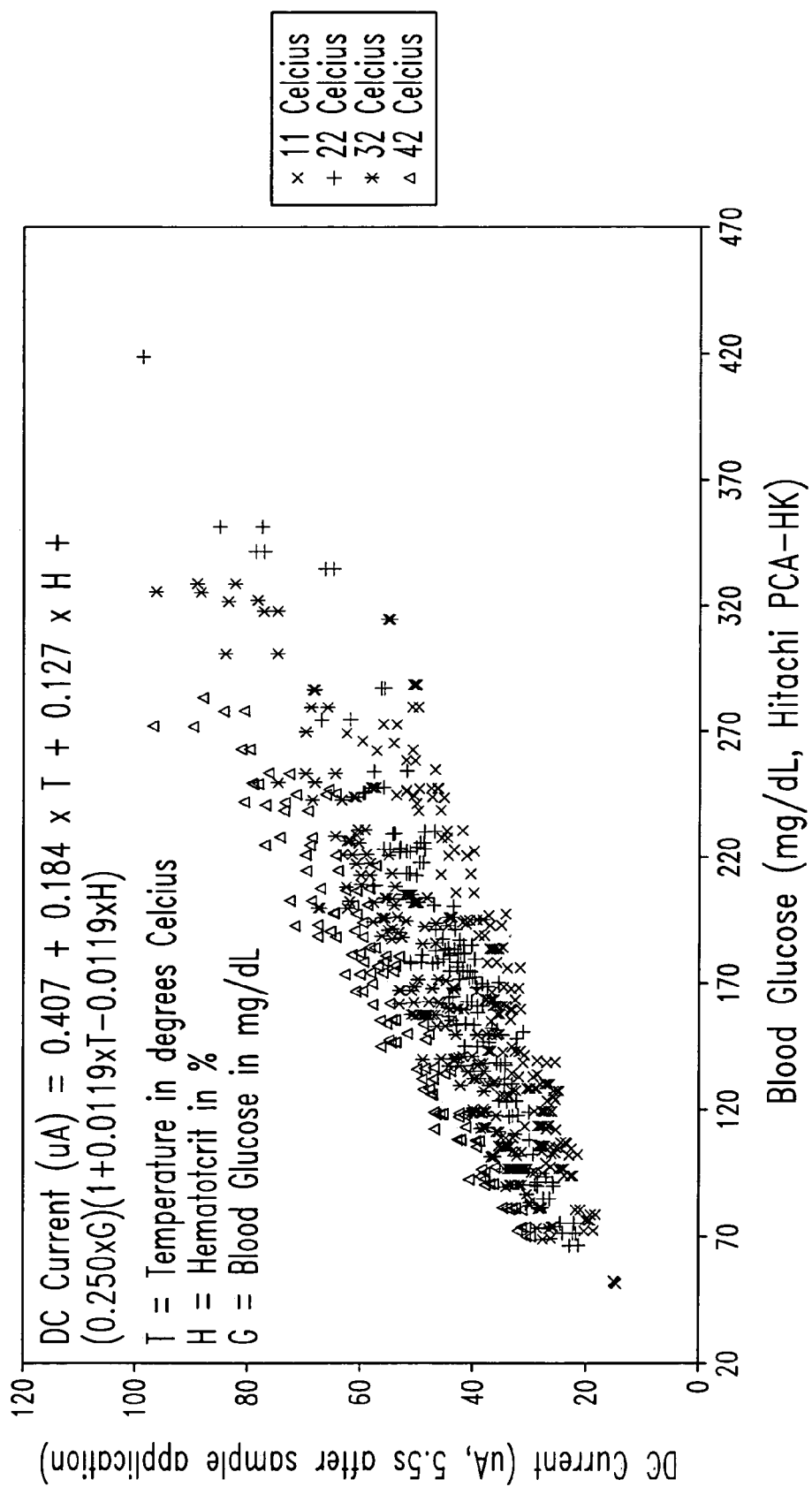
FIG. 8 is a plot of uncompensated DC current versus glucose for the test of Example 2.
Figure 9:
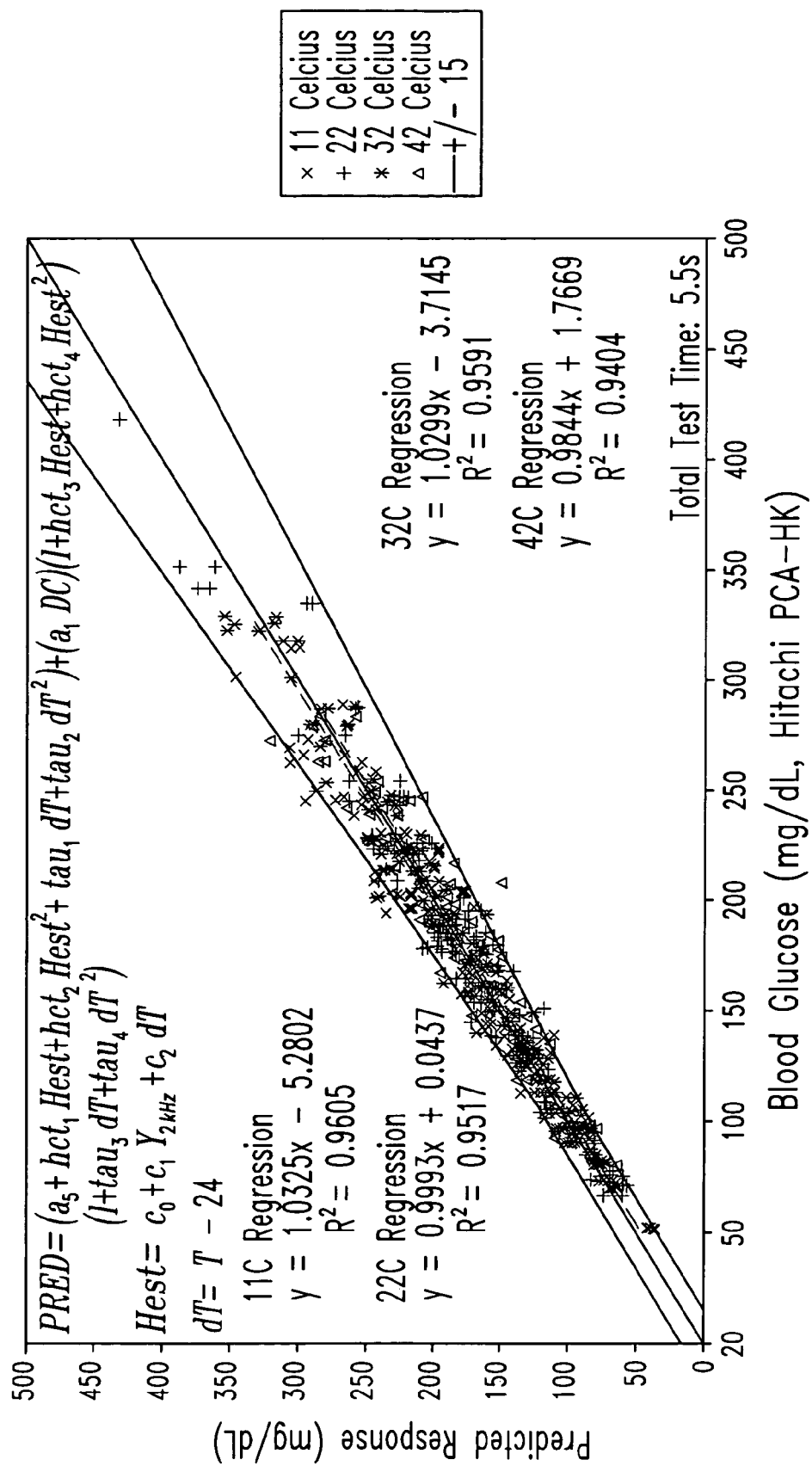
FIG. 9 is a plot of the predicted glucose response versus actual glucose response for the test of Example 2.

FIG. 8 illustrates the uncompensated 5.5 second DC glucose response of all of the capillary blood samples as temperature varies (ignoring the AC measurement data). As will be appreciated, there is a wide variation in the DC current response as temperature and hematocrit vary. FIG. 9 illustrates the correlation between the actual blood glucose level of the sample versus the predicted response using Equation 2. As can be seen, when the DC response is compensated for hematocrit levels using the AC response data, $r^2$ values of 0.9404 to 0.9605 are achieved with a Total Test Time of 5.5 seconds.

EXAMPLE 3

Use of AC Phase Angle to Estimate Blood Glucose Levels and Hematocrit

The measurements made in Example 3 were also achieved using the test strip illustrated in FIGS. 3A-B and indicated generally at 300. As described above, the test strip 300 includes a capillary fill space containing a relatively thick film reagent and working and counter electrodes, as described in U.S. Pat. No. 5,997,817, which is hereby incorporated by reference. Because hematocrit levels from capillary blood samples typically vary only between 30%-50%, spiked venous blood samples having a hematocrit range from 20%-70% were used for this Example 3. Five levels of glucose, temperature (14, 21, 27, 36 and 42° C.) and hematocrit (20, 30, 45, 60 and 70%) were independently varied, producing a covariance study with 125 samples.

Figure 10:
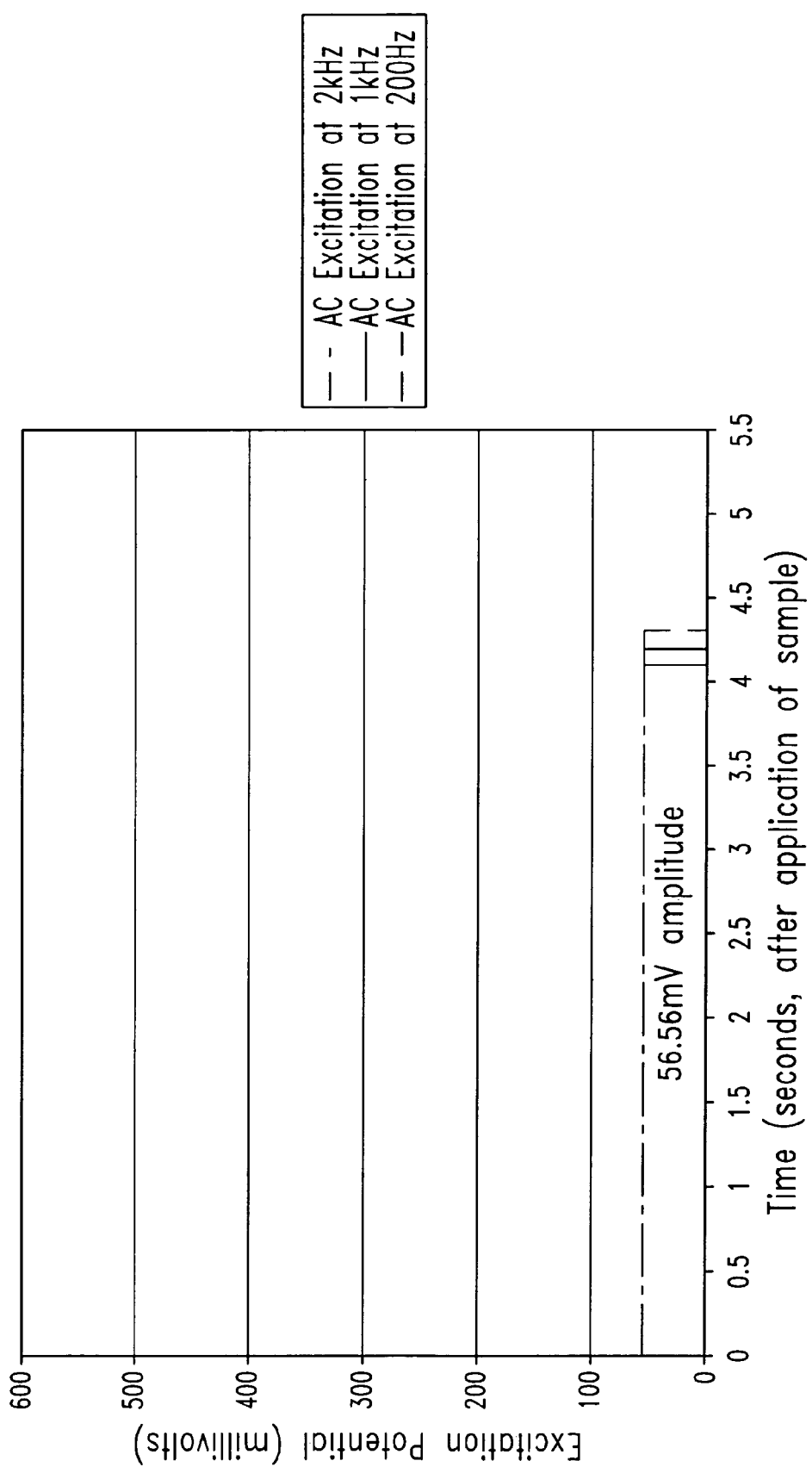
FIG. 10 is a diagram of an excitation signal utilized in the test of Example 3.

In the measurements, blood samples were applied to test strip 300 and the excitation potentials illustrated in FIG. 10 were applied to the electrodes. The excitation comprised a 2 kHz AC signal for approximately 4.1 seconds, a 1 kHz AC signal for approximately 0.1 seconds, and a 200 Hz signal for approximately 0.1 seconds. All three AC signals had an amplitude of 56.56 mV peak. No DC excitation was used in this example. The Total Test Time was 4.3 seconds from sample application time.

Figure 11:
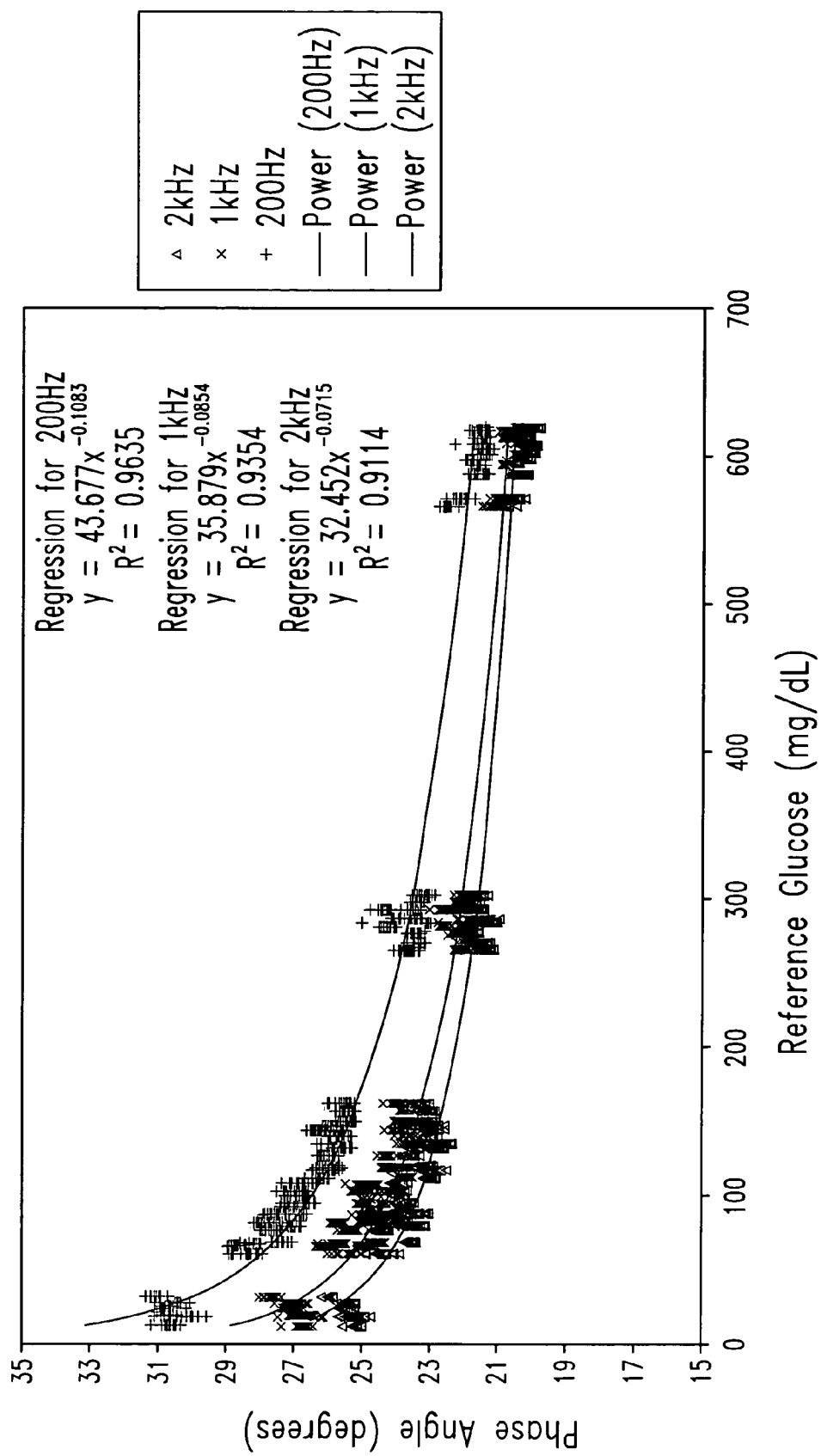
FIG. 11 is a plot of the AC phase angle versus reference glucose for the test of Example 3.

It was found that another component of the AC response, the phase angle (particularly at lower frequencies, such as 200 Hz in this Example 3), is also a function of the sample glucose level in the case of this test strip and reagent. This relationship is demonstrated in FIG. 11, where the AC phase angle for each of the three test frequencies is plotted versus the reference glucose level. Regression analysis for each of the three frequencies produces AC phase angle-to-reference glucose level $r^2$ correlation values of 0.9114 at 2 kHz, 0.9354 at 1 kHz, and 0.9635 at 200 Hz. The present invention therefore comprehends the use of the AC phase angle to measure glucose levels. The AC excitation frequency producing the measured phase angle is preferably 2 kHz or below, more preferably 1 kHz or below, and most preferably 200 Hz or below, but not including DC excitation.

The linearized relationship between the 200 Hz phase angle response and the blood glucose level is as follows:

$$P_{eff} = (\Phi_{200\,Hz}/\Gamma)^{-\gamma} \qquad \text{(Equation 3)}$$

where $P_{eff}$ is the effective phase, which is proportional to glucose, the terms $\Gamma$ and $\gamma$ are constants, and $\Phi$ is the measured AC phase angle.

Using the same approach to compensate for temperature and hematocrit as used in Example 1 above (see Equations 1 and 2) produced a predictive algorithm as follows:

$$\text{PRED} = (a_0 + hct_1 H_{est} + hct_2 H_{est}^2 + tau_1 dT + tau_2 dT^2) + (a_1 P_{eff})(1 + hct_3 H_{est} + hct_4 H_{est}^2)(1 + tau_3 dT + tau_4 dT^2) \qquad \text{(Equation 4)}$$

Figure 12:
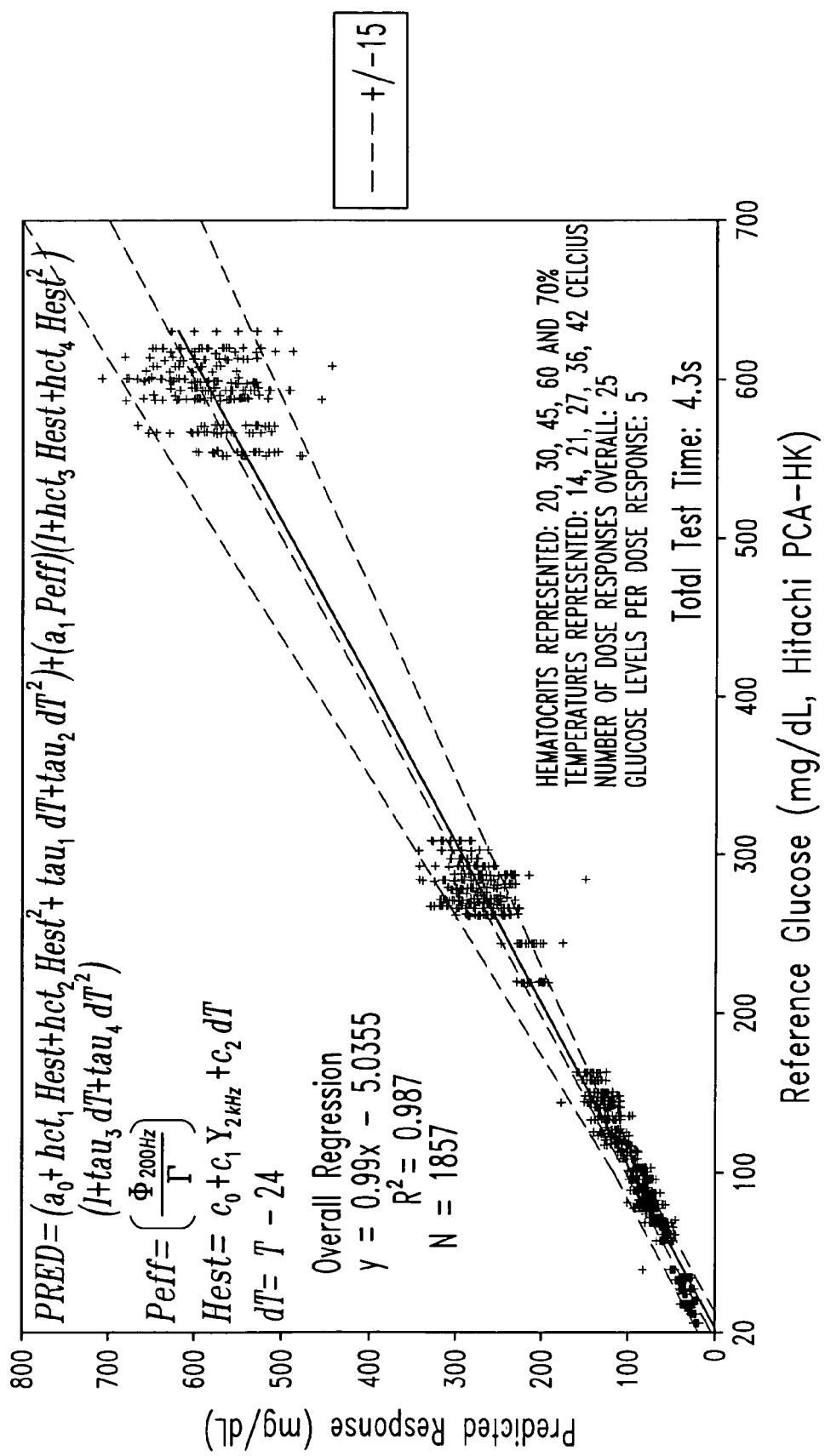
FIG. 12 is a plot of the predicted glucose response versus the actual glucose response for the test of Example 3.

The resulting compensated (predicted) response PRED versus glucose for the 125 blood samples (each tested with eight test strips) is shown in FIG. 12. The $r^2$ correlation of the PRED response vs. known glucose level, where all temperatures and all hematocrits are combined, is 0.9870. This Example 3 demonstrates again the value of AC measurements for compensating for interferants that reduce the accuracy of blood glucose measurements. Using an existing commercially available sensor, the present invention yields a 4.3 second Total Test Time with an overall $r^2$ of 0.9870.

It was also determined that AC phase angle measurements can produce hematocrit level measurements that are almost immune to the effects of temperature variation. In another covariant study of 125 samples (five glucose concentrations, five hematocrit concentrations and five temperatures), each of the samples was tested using an excitation profile of 20 kHz, 10 kHz, 2 kHz, 1 kHz and DC. The AC phase angle at various frequencies was related to glucose, hematocrit and temperature using linear regression to determine the coefficients of the following formula at each of the four AC frequencies:

$$\text{Phase} = c_0 + c_1 \text{Glu} + c_2 \text{HCT} + c_3 \text{Temp} \quad \text{(Equation 5)}$$

where Glu is the known glucose concentration, HCT is the known hematocrit concentration and Temp is the known temperature.

The determined coefficients revealed that the temperature coefficient ($c_3$) was essentially zero at 20 kHz and 10 kHz, cancelling temperature from the equation at these frequencies. Furthermore, the glucose coefficient ($c_1$) is essentially zero at all of the AC frequencies because, as explained hereinabove, the higher frequency AC impedance measurements are largely unaffected by glucose levels and are therefore useful for measuring the levels of interfering substances. It was therefore found that the hematocrit level could be determined independent of temperature and glucose level using only the AC phase angle measurements. In a preferred embodiment, the hematocrit may be measured using the phase angle data from all four measured frequencies:

$$H_{est} = c_0 + c_1 \Phi_{20\ kHz} + c_2 \Phi_{10\ kHz} + c_3 \Phi_{2\ kHz} + c_4 \Phi_{1\ kHz} \quad \text{(Equation 6)}$$

Those skilled in the art will recognise that that the coefficients can be empirically determined for any particular test strip architecture and reagent chemistry. The present invention therefore may be used to estimate hematocrit using only AC phase angle measurements preferably made at at least one AC frequency, more preferably made at at least two AC frequencies, and most preferably made at at least four AC frequencies.

EXAMPLE 4

Combined AC and DC Measurement Using Nitrosoaniline Reagent

The measurements made in Example 4 were also achieved using the test strip illustrated in FIGS. 3A-B and indicated generally at 300. As described above, the test strip 300 includes a capillary fill space containing a relatively thick film reagent and working and counter electrodes, as described in U.S. Pat. No. 5,997,817, which is hereby incorporated by reference. The test strip was modified from that described in U.S. Pat. No. 5,997,817, however, by the use of a different reagent. The nitrosoaniline reagent used had the composition described in Tables III and IV.

TABLE III

Reagent Mass Composition - Prior to Dispense and Drying

| | Component | % w/w | Mass for 1 kg |
|---|---|---|---|
| solid | Polyethylene oxide (300 kDa) | 0.8054% | 8.0539 g |
| solid | Natrosol 250M | 0.0470% | 0.4698 g |
| solid | Avicel RC-591F | 0.5410% | 5.4104 g |
| solid | Monobasic potassium phosphate (annhydrous) | 1.1437% | 11.4371 g |
| solid | Dibasic potassium phosphate (annhydrous) | 1.5437% | 15.4367 g |
| solid | Disodium Succinate hexahydrate | 0.5876% | 5.8761 g |
| solid | Potassium Hydroxide | 0.3358% | 3.3579 g |
| solid | Quinoprotein glucose dehydrogenase (EnzC#: 1.1.99.17) | 0.1646% | 1.6464 g |
| solid | PQQ | 0.0042% | 0.0423 g |
| solid | Trehalose | 1.8875% | 18.8746 g |
| solid | Mediator 31.1144 | 0.6636% | 6.6363 g |
| solid | Triton X-100 | 0.0327% | 0.3274 g |
| solvent | Water | 92.2389% | 922.3888 g |

| % Solids | 0.1352687 |
|---|---|
| Target pH | 6.8 |
| Specific Enzyme Activity Used (U/mg) | 689 DCIP |
| Dispense Volume per Sensor | 4.6 mg |

TABLE IV

Reagent Layer Composition - After Drying

| | Component | % w/w | Mass per Sensor |
|---|---|---|---|
| solid | Polyethylene oxide (300 kDa) | 10.3829% | 37.0480 ug |
| solid | Natrosol 250M | 0.6057% | 2.1611 ug |
| solid | Avicel RC-591F | 6.9749% | 24.8877 ug |
| solid | Monobasic potassium phosphate (annhydrous) | 14.7445% | 52.6107 ug |
| solid | Dibasic potassium phosphate (annhydrous) | 19.9006% | 71.0087 ug |
| solid | Disodium Succinate hexahydrate | 7.5753% | 27.0299 ug |
| solid | Potassium Hydroxide | 4.3289% | 15.4462 ug |
| solid | Quinoprotein glucose dehydrogenase (EnzC#: 1.1.99.17) | 2.1225% | 7.5734 ug |
| solid | PQQ | 0.0546% | 0.1947 ug |
| solid | Trehalose | 24.3328% | 86.8243 ug |
| solid | Mediator BM 31.1144 | 8.5553% | 30.5268 ug |
| solid | Triton X-100 | 0.4220% | 1.5059 ug |

The method for the manufacture of the glucose biosensor for this Example 4 is the same in all respects as disclosed in U.S. Pat. No. 5,997,817 except for the manufacture of the reagent. A protocol for the preparation of the preferred embodiment nitrosoaniline reagent is as follows:

Step 1: Prepare a buffer solution by adding 1.54 g of dibasic potassium phosphate (anhydrous) to 43.5 g of deionized water. Mix until the potassium phosphate is dissolved.

Step 2: To the solution from step 1, add 1.14 g of monobasic potassium phosphate and mix until dissolved.

Step 3: To the solution from step 2, add 0.59 g of disodium succinate (hexahydrate) and mix until dissolved.

Step 4: Verify that the pH of the solution from step 3 is 6.7+/−0.1. Adjustment should not be necessary.

Step 5: Prepare a 5 g aliquot of the solution from step 4, and to this add 113 kilounits (by DCIP assay) of the apoenzyme of quinoprotein glucose dehydrogenase (EC#: 1.1.99.17). This is approximately 0.1646 g. Mix, slowly, until the protein is dissolved.

Step 6: To the solution from step 5, add 4.2 milligrams of PQQ and mix for no less than 2 hours to allow the PQQ and the apoenzyme to reassociate in order to provide functional enzyme.

Step 7: To the solution from step 4, add 0.66 g of the mediator precursor, N,N-bis(hydroxyethyl)-3-methoxy-4-nitrosoaniline (hydrochloride) (BM 31.1144). Mix until dissolved (this solution will have a greenish black coloration).

Step 8: Measure the pH of the solution from step 7 and adjust the pH to a target of 7.0+/−0.1. Normally this is accomplished with 1.197 g of 5N potassium hydroxide. Because the specific amount of potassium hydroxide may vary as needed to reach the desired pH, generally deviations in mass from the 1.197 g are made up from an aliquot of 3.309 g deionized water which is also added at this step.

Step 9: Prepare a solution of Natrosol 250M (available from Aqualon), by slowly sprinkling 0.047 g over 44.57 g of deionized water which is mixed (using a rotary mixer and blade impeller) at a rate of approximately 600 rpm in a vessel of sufficient depth such that the rotor blades are not exposed nor the solution running over. Mix until the Natrosol is completely dissolved.

Step 10: Prepare a suspension of Avicel RC-591F (available from FMS), by slowly sprinkling 0.54 g onto the surface of the solution from step 9, mixing at a rate of approximately 600 rpm for not less than 60 minutes before proceeding.

Step 11: To the suspension from step 10, gradually add 0.81 g of Polyethylene oxide of 300 kDa mean molecular weight while mixing and continue to mix for not less than 60 minutes before proceeding.

Step 12: Gradually add the solution from step 8 to the suspension from step 11 while mixing. Reduce the mixing rate to 400 rpm.

Step 13: To the reagent from step 12, add 1.89 g of Trehalose and continue mixing for not less than 15 minutes.

Step 14: To the reagent from step 13, add 32.7 mg of Triton X-100 (available from Roche Diagnostics) and continue mixing.

Step 15: To the reagent from step 14, add the enzyme solution from step 6. Mix for no less than 30 minutes. At this point the reagent is complete. At room temperature the wet reagent mass is considered acceptable for use for 24 hours.

Figure 13:
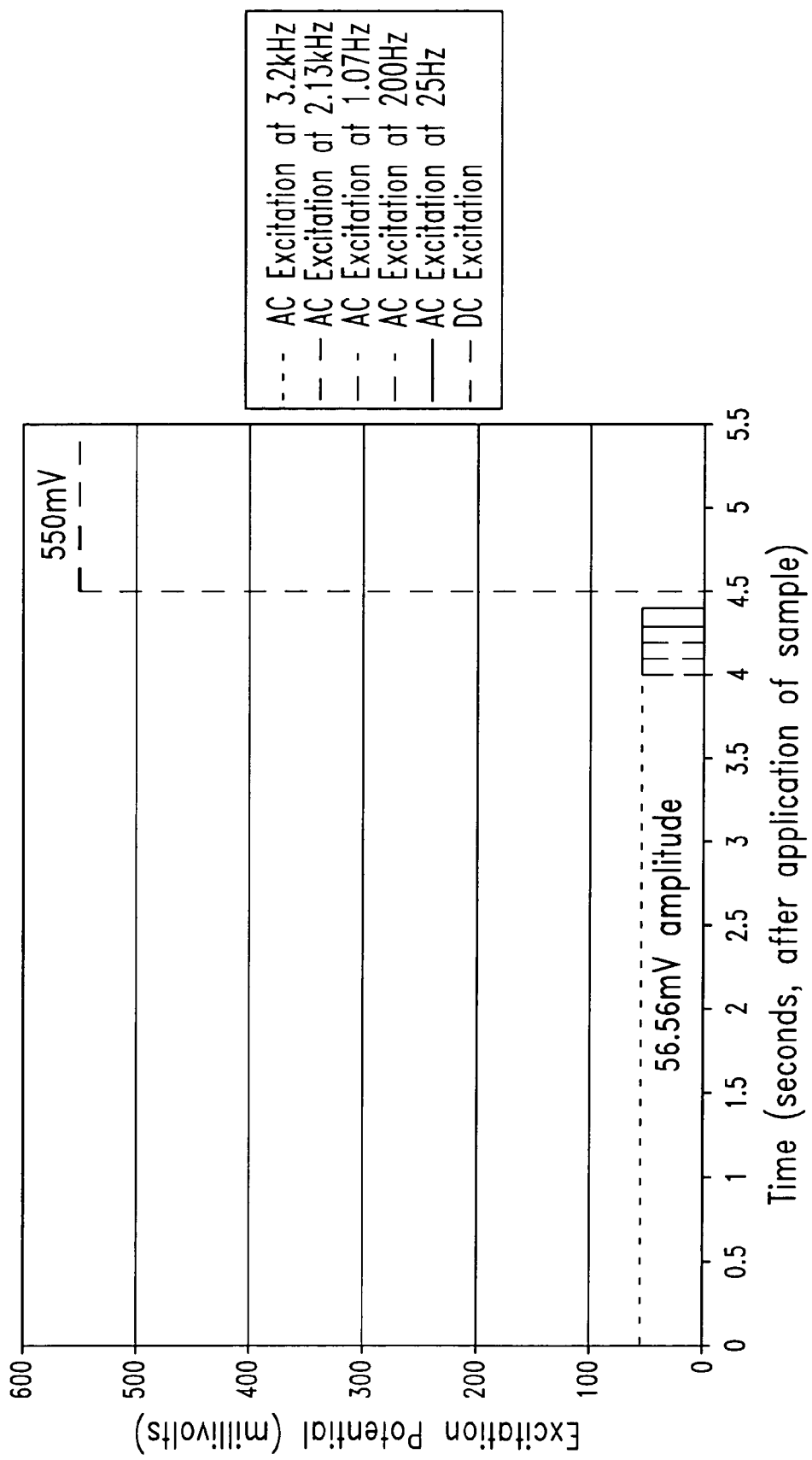
FIG. 13 is a diagram of an excitation signal utilized in the test of Example 4.

Spiked venous blood samples were used. Five levels of glucose, four temperatures (19, 23, 32 and 38° C.) and five levels of hematocrit (20, 30, 45, 60 and 70%) were independently varied, producing a covariance study with 100 samples. 16 test strips 300 were tested for each unique combination of glucose, temperature and hematocrit. The blood samples were applied to test strip 300 and the excitation potentials illustrated in FIG. 13 were applied to the electrodes. The excitation comprised a 3.2 kHz AC signal for approximately 4.0 seconds, a 2.13 kHz AC signal for approximately 0.1 seconds, a 1.07 kHz AC signal for approximately 0.1 seconds, a 200 Hz AC signal for approximately 0.1 seconds, a 25 Hz AC signal for approximately 0.1 seconds, followed by a DC signal of 550 mV for approximately 1.0 second. All four AC signals had an amplitude of 56.56 mV peak. The Total Test Time was 5.5 seconds from sample application time.

Figure 14:
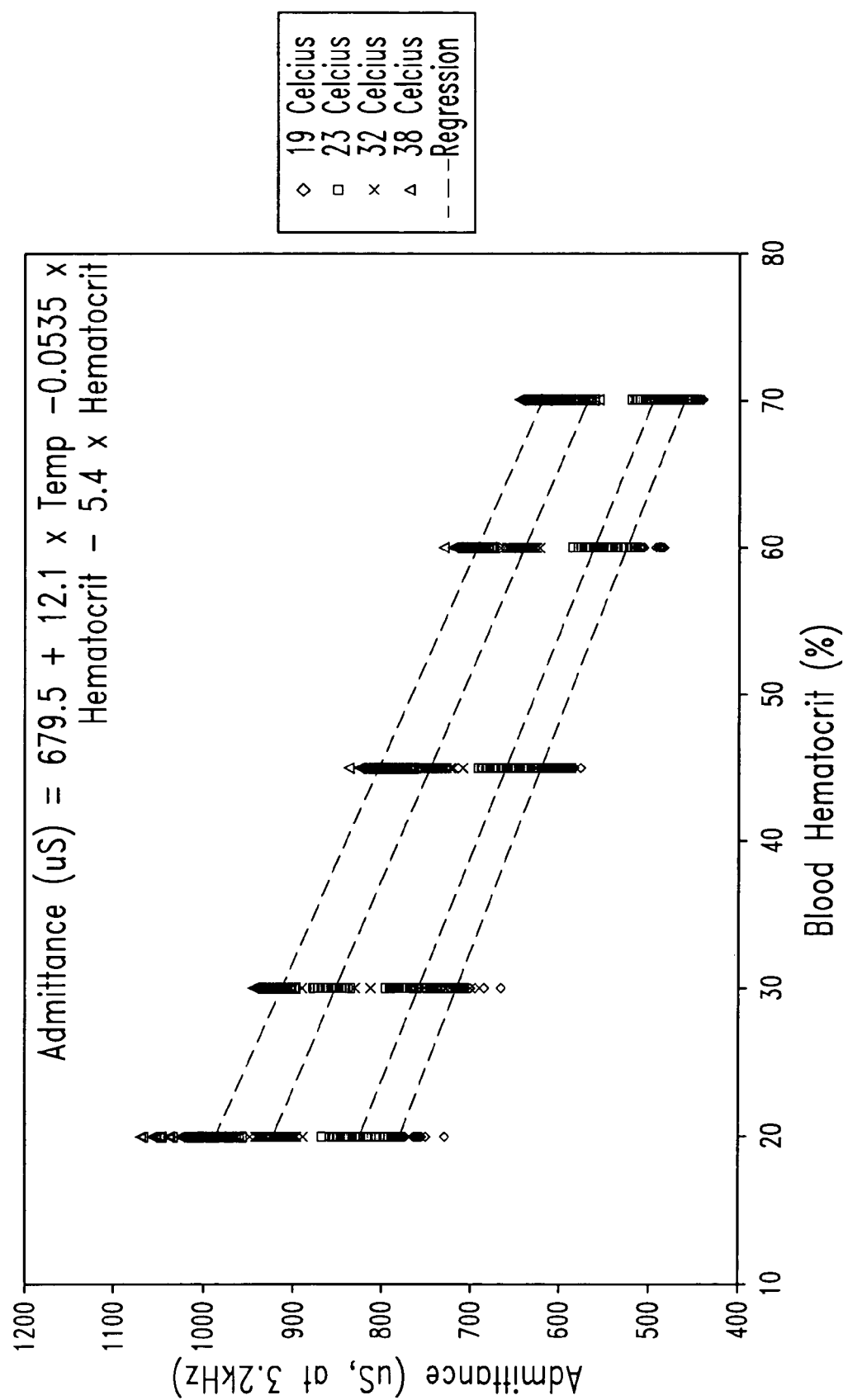
FIG. 14 is a plot of AC admittance versus hematocrit (parametrically displayed with temperature) for the test of Example 4.

In this Example 4, the AC response of the sample was derived as admittance (the inverse of impedance). The admittance response is proportionate to the hematocrit level of the sample in a temperature dependent manner. The relationship between admittance, hematocrit and testing temperature is illustrated in FIG. 14. As compared to the test strip architecture of Example 2, the orthogonality of the temperature and hematocrit influence on glucose was not as strong in this Example 4, therefore a cross product term (T×HCT) was added to the admittance regression formula used in FIG. 14. The data used for the admittance charted in FIG. 14 is the last admittance measurement made for each sample during the 3.2 kHz AC portion of the excitation illustrated in FIG. 13.

Regression analysis of this data allows admittance, hematocrit and temperature to be related according to the following formula:

$$H_{est} = (Y_{3.2\ kHz} + c_0 + c_1 dT)/(c_2 dT + c_3)$$ (Equation 7)

It was determined that the admittance measurement made at 3.2 kHz was best correlated with hematocrit for this test system. Using this relationship to predict the blood hematocrit is accomplished using test temperature data reported by the temperature sensor in the meter and the measured admittance. In Equation 7, $c_0$, $c_1$, $c_2$ and $c_3$ are constants, dT is the deviation in temperature from a center defined as "nominal" (24° C. for example), and $H_{est}$ is the estimated deviation in hematocrit from a similar "nominal" value. For the present purposes, the actual hematocrit value is not; necessary, and it is generally preferred to produce a response which is proportionate but centers around a nominal hematocrit. Thus, for a 70% hematocrit, the deviation from a nominal value of 42% would be 28%, while conversely for a 20% hematocrit the deviation from the same nominal value would be −22%.

By using the AC admittance measurement to estimate the hematocrit level using Equation 7, the accuracy of the DC glucose response can be greatly improved by combining the estimated hematocrit, temperature and DC response to correct for the hematocrit interference in the DC response as follows (same as Equation 2 above):

$$PRED = (a_0 + hct_1 H_{est} + hct_2 H_{est}^2 + tau_1 + tau_2 dT^2) + (a_1 DC)(1 + hct_3 H_{est} + hct_4 H_{est}^2)(1 + tau_3 dT + tau_4 dT^2)$$ (Equation 8)

The constants in Equation 8 can be determined using regression analysis, as is known in the art.

Figure 15:
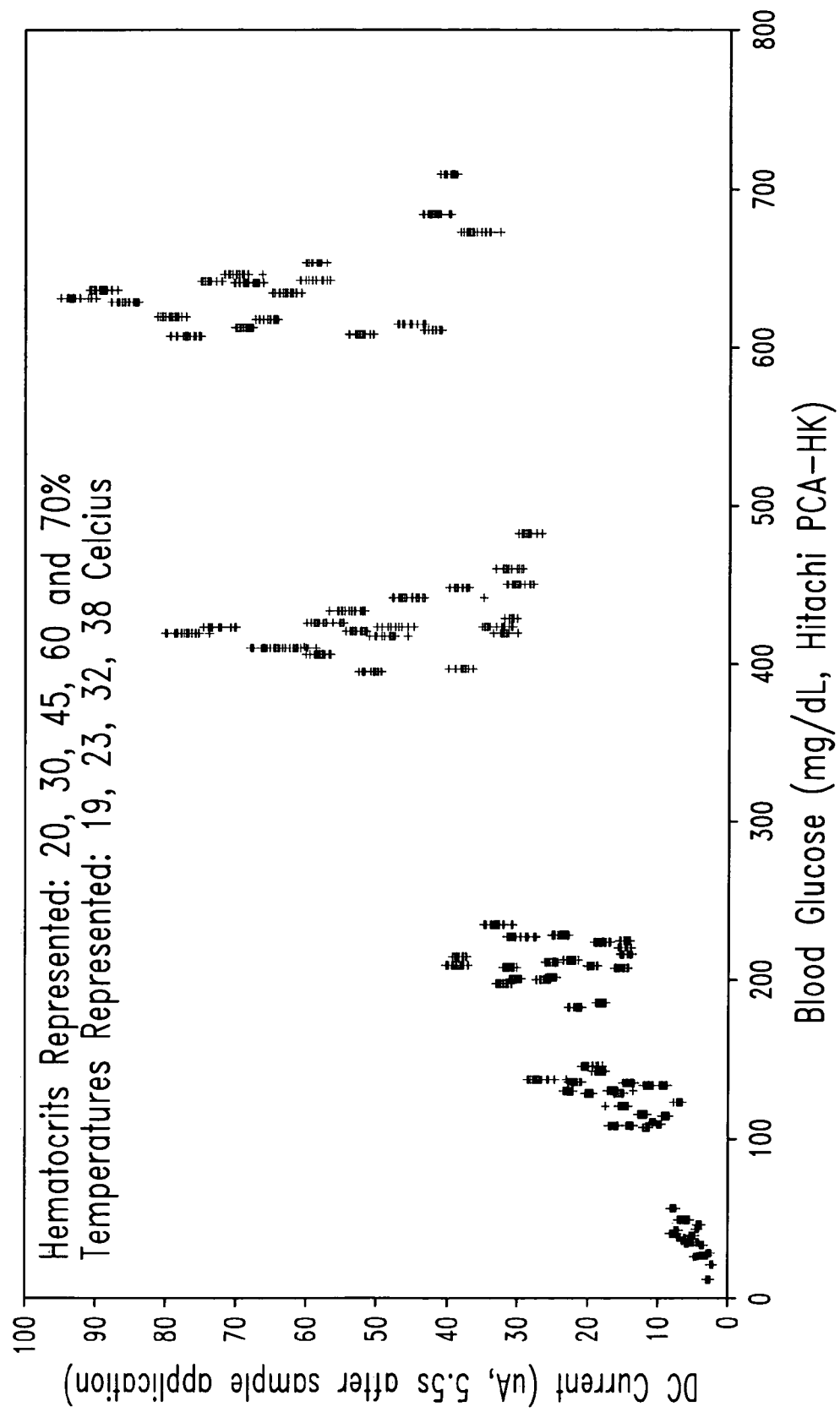
FIG. 15 is a plot of the uncompensated DC response versus actual glucose for the test of Example 4.
Figure 16:
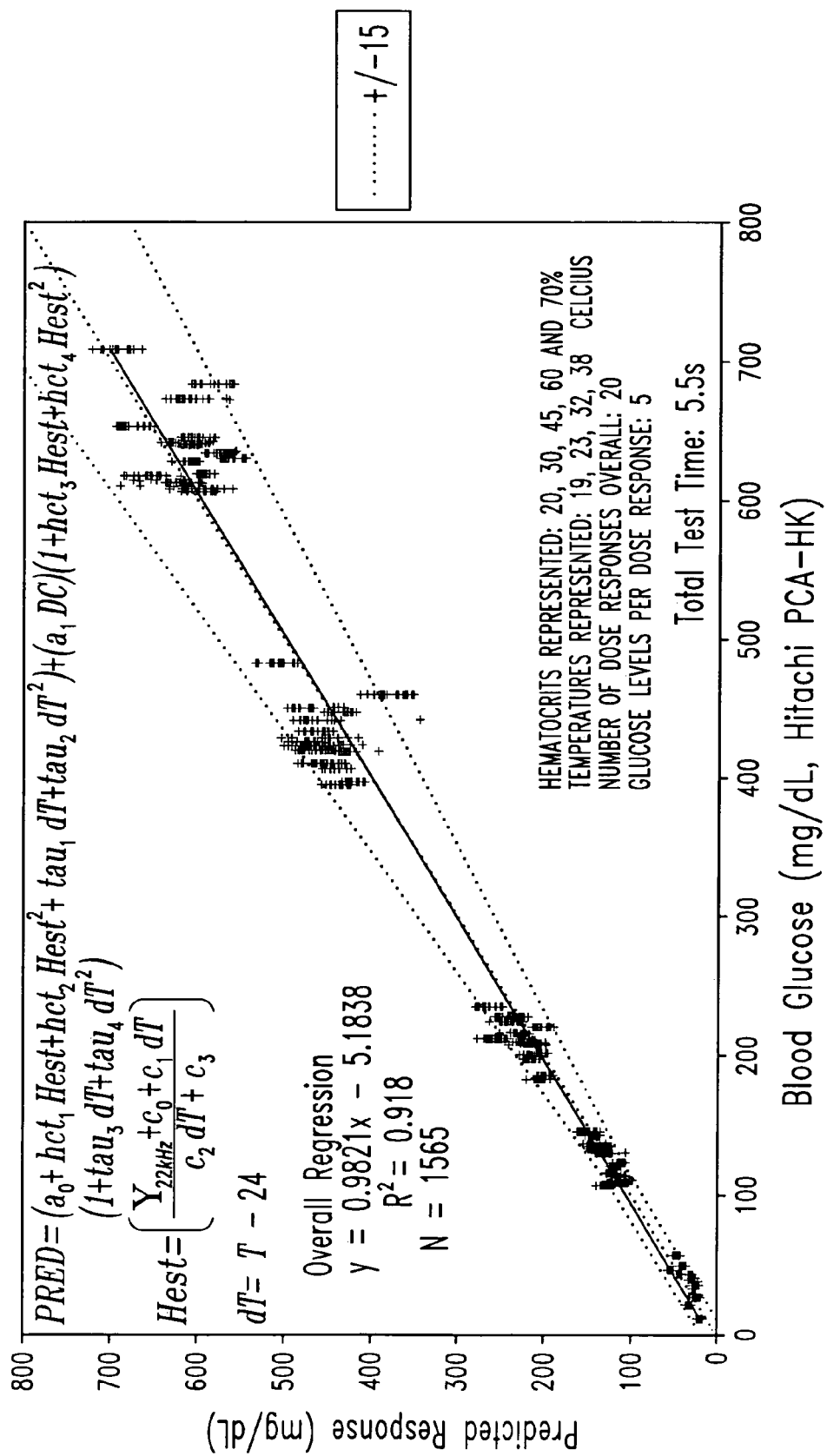
FIG. 16 is a plot of the predicted glucose response versus actual glucose response for the test of Example 4.

FIG. 15 illustrates the uncompensated 5.5 second DC glucose response of all of the blood samples as hematocrit and temperature vary (ignoring the AC measurement data). As will be appreciated, there is a wide variation in the DC current response as temperature and hematocrit vary. FIG. 16 illustrates the correlation between the actual blood glucose level of the sample versus the predicted response using Equation 8. As can be seen, when the DC response is compensated for hematocrit levels using the AC response data, an overall $r^2$ value of 0.9818 is achieved with a Total Test Time of 5.5 seconds. This demonstrates the applicability of the present invention in achieving high accuracy and fast test times with a different reagent class than was used in Examples 1-3.

EXAMPLE 5

Combined AC and DC Measurement Using a 0.397 μl Sample

The measurement methods of the present invention have been found to be useful with other test strip designs as well. Example 5 was conducted using the test strip design illustrated in FIGS. 17A-B, and indicated generally at 1700. Referring to FIG. 17A, the test strip 1700 comprises a bottom foil layer 1702 formed from an opaque piece of 350 μm thick polyester (in the preferred embodiment this is Melinex 329 available from DuPont) coated with a 50 nm conductive (gold) layer (by sputtering or vapor deposition, for example). Electrodes and connecting traces are then patterned in the conductive layer by a laser ablation process to form working, counter, and dose sufficiency electrodes (described in greater detail hereinbelow) as shown. The laser ablation process is performed by means of an excimer laser which passes through a chrome-on-quartz mask. The mask pattern causes parts of the laser field to be reflected while allowing other parts of the field to pass through, creating a pattern on the gold which is ejected from the surface where contacted by the laser light.

Examples of the use of laser ablation techniques in preparing electrodes for biosensors are described in U.S. patent application Ser. No. 09/866,030, "Biosensors with Laser Ablation Electrodes with a Continuous Coverlay Channel" filed May 25, 2001, and in U.S. patent application Ser. No. 09/411,940, entitled "Laser Defined Features for Patterned Laminates and Electrode," filed Oct. 4, 1999, both disclosures incorporated herein by reference.

The bottom foil layer 1702 is then coated in the area extending over the electrodes with a reagent layer 1704 in the form of an extremely thin reagent film. This procedure places a stripe of approximately 7.2 millimeters width across the bottom foil 1702 in the region labelled "Reagent Layer" on FIG. 17. In the present Example, this region is coated at a wet-coat weight of 50 grams per square meter of coated surface area leaving a dried reagent less than 20 µm thick. The reagent stripe is dried conventionally with an in-line drying system where the nominal air temperature is at 110° C. The rate of processing is nominally 30-38 meters per minute and depends upon the rheology of the reagent.

The materials are processed in continuous reels such that the electrode pattern is orthogonal to the length of the reel, in the case of the bottom foil 1702. Once the bottom foil 1702 has been coated with reagent, the spacer is slit and placed in a reel-to-reel process onto the bottom foil 1702. Two spacers 1706 formed from 100 µm polyester (in the preferred embodiment this is Melinex 329 available from DuPont) coated with 25 µm PSA (hydrophobic adhesive) on both the dorsal and ventral surfaces are applied to the bottom foil layer 1702, such that the spacers 1706 are separated by 1.5 mm and the working, counter and dose sufficiency electrodes are centered in this gap. A top foil layer 1708 formed from 100 µm polyester coated with a hydrophilic film on its ventral surface (using the process described in U.S. Pat. No. 5,997,817) is placed over the spacers 1706. In the preferred embodiment, the hydrophilic film is coated with a mixture of Vitel and Rhodapex surfactant at a nominal thickness of 10 microns. The top foil layer 1708 is laminated using a reel-to-reel process. The sensors can then be produced from the resulting reels of material by means of slitting and cutting.

The 1.5 mm gap in the spacers 1706 therefore forms a capillary fill space between the bottom foil layer 1702 and the top foil layer 1708. The hydrophobic adhesive on the spacers 1706 prevents the test sample from flowing into the reagent under the spacers 1706, thereby defining the test chamber volume. Because the test strip 1700 is 5 mm wide and the combined height of the spacer 1706 and conductive layer is 0.15 mm, the sample receiving chamber volume is $$5 \text{ mm} \times 1.5 \text{ mm} \times 0.15 \text{ mm} = 1.125 \text{ µl} \quad \text{(Equation 9)}$$

As shown in FIG. 17B, the distance from the sample application port 1710 and the dose sufficiency electrodes is 1.765 mm. The volume of sample needed to sufficiently cover the working, counter and dose sufficiency electrodes (i.e. the minimum sample volume necessary for a measurement) is $$1.5 \text{ mm} \times 1.765 \text{ mm} \times 0.15 \text{ mm} = 0.397 \text{ µl} \quad \text{(Equation 10)}$$

The reagent composition for the test strip 1700 is given in Tables V and VI.

TABLE V

Reagent Mass Composition - Prior to Dispense and Drying

| | Component | % w/w | Mass for 1 kg |
|---|---|---|---|
| solid | Polyethylene oxide (300 kDa) | 1.0086% | 10.0855 g |
| solid | Natrosol 250M | 0.3495% | 3.4954 g |
| solid | Carboxymethylcellulose 7HF | 0.3495% | 3.4954 g |
| solid | Monobasic potassium phosphate (annhydrous) | 0.9410% | 9.4103 g |
| solid | Dibasic potassium phosphate (trihydrous) | 1.6539% | 16.5394 g |
| solid | Disodium Succinate hexahydrate | 0.2852% | 2.8516 g |
| solid | Potassium Hydroxide | 0.2335% | 2.3351 g |
| solid | Quinoprotein glucose dehydrogenase (EnzC#: 1.1.99.17) | 0.3321% | 3.3211 g |
| solid | PQQ | 0.0093% | 0.0925 g |
| solid | Trehalose | 0.7721% | 7.7210 g |
| solid | Mediator 31.1144 | 0.6896% | 6.8956 g |
| solid | Triton X-100 | 0.0342% | 0.3419 g |
| solvent | Water | 93.7329% | 937.3293 g |

| % Solids | 6.6585% |
|---|---|
| Target pH | 7 |
| Specific Enzyme Activity Used (U/mg) | 689 DCIP |
| Wet Reagent Coat Weight per Sensor (ug/mm$^2$) | 50 |

TABLE VI

Reagent Layer Composition - After Drying

| | Component | % w/w | Mass per Sensor* |
|---|---|---|---|
| solid | Polyethylene oxide (300 kDa) | 15.1469% | 3.7821 ug |
| solid | Natrosol 250M | 5.2495% | 1.3108 ug |
| solid | Carboxymethylcellulose 7HF | 5.2495% | 1.3108 ug |
| solid | Monobasic potassium phosphate (annhydrous) | 14.1328% | 3.5289 ug |
| solid | Dibasic potassium phosphate (trihydrous) | 24.8395% | 6.2023 ug |
| solid | Disodium Succinate hexahydrate | 4.2827% | 1.0694 ug |
| solid | Potassium Hydroxide | 3.5069% | 0.8757 ug |
| solid | Quinoprotein glucose dehydrogenase (EnzC#: 1.1.99.17) | 4.9878% | 1.2454 ug |
| solid | PQQ | 0.1390% | 0.0347 ug |
| solid | Trehalose | 11.5958% | 2.8954 ug |
| solid | Mediator BM31.1144 | 10.3562% | 2.5859 ug |
| solid | Triton X-100 | 0.5135% | 0.1282 ug |

*"Mass per Sensor" is the amount of the component within the capillary; this does not reflect the reagent that is outside of the capillary.

A protocol for the preparation of the preferred embodiment nitrosoaniline reagent is as follows:

Step 1: Prepare a buffer solution by adding 1.654 g of dibasic potassium phosphate (trihydrous) to 31.394 g of deionized water. Mix until the potassium phosphate is dissolved.

Step 2: To the solution from step 1, add 0.941 g of monobasic potassium phosphate and mix until dissolved.

Step 3: To the solution from step 2, add 0.285 g of disodium succinate (hexahydrate) and mix until dissolved.

Step 4: Verify that the pH of the solution from step 3 is 6.8+/−0.1. Adjustment should not be necessary.

Step 5: Prepare a 4.68 g aliquot of the solution from step 4, and to this add 229 kilounits (by DCIP assay) of the apoenzyme of quinoprotein glucose dehydrogenase (EC#: 1.1.99.17). This is approximately 0.3321 g. Mix, slowly, until the protein is dissolved.

Step 6: To the solution from step 5, add 9.3 milligrams of PQQ and mix for no less than 2 hours to allow the PQQ and the apoenzyme to reassociate in order to provide functional enzyme.

Step 7: Prepare a solution by dissolving 0.772 g of Trehalose into 1.218 g of deionized water.

Step 8: After enzyme reassociation, add the solution from step 7 to the solution from step 6 and continue mixing for not less than 30 minutes.

Step 9: To the solution from step 4, add 0.690 g of the mediator precursor BM 31.1144. Mix until dissolved (this solution will have a greenish black coloration).

Step 10: Measure the pH of the solution from step 9 and adjust the pH to a target of 7.0+/−0.1. Normally this is accomplished with 1.006 g of 5N potassium hydroxide. Because the specific amount of potassium hydroxide may vary as needed to reach the desired pH, generally deviations in mass from the 1.006 g are made up from an aliquot of 3.767 g deionized water which is also added at this step.

Step 11: Prepare a solution of Natrosol 250M (available from Aqualon), by slowly sprinkling 0.350 g over 56.191 g of deionized water which is mixed (using a rotary mixer and blade impeller) at an initial rate of approximately 600 rpm in a vessel of sufficient depth such that the rotor blades are not exposed nor the solution running over. As the Natrosol dissolves, the mixing rate needs to be increased to a speed of. 1.2-1.4 krpm. Mix until the Natrosol is completely dissolved. Note that the resulting matrix will be extremely viscous—this is expected.

Step 12: To the solution from step 11, gradually add 0.350 g of Sodium-Carboxymethylcellulose 7HF (available from Aqualon). Mix until the polymer is dissolved.

Step 13: To the suspension from step 13, gradually add 1.01 g of Polyethylene oxide of 300 kDa mean molecular weight while mixing and continue to mix for not less than 60 minutes before proceeding.

Step 14: Gradually add the solution from step 10 to the suspension from step 13 while mixing.

Step 15: To the reagent from step 14, add 34.2 mg of Triton X-100 (available from Roche Diagnostics) and continue mixing.

Step 16: To the reagent from step 15, add the enzyme solution from step 8. Mix for no less than 30 minutes. At this point the reagent is complete. At room teperature the wet reagent mass is considered acceptable for use for 24 hours.

Figure 18:
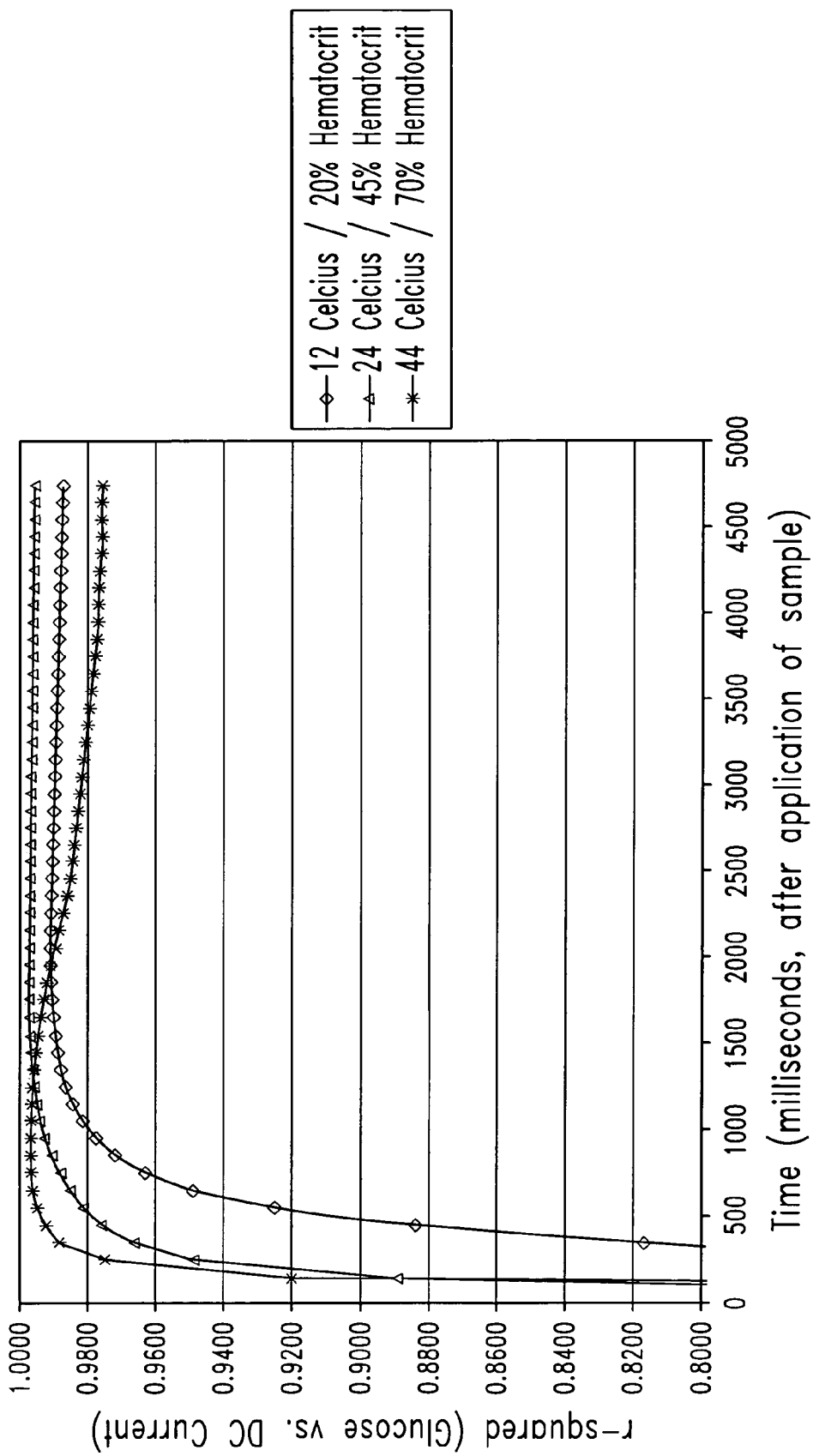
FIG. 18 is a plot parametrically illustrating the correlation coefficient $r^2$ between the DC current response and glucose level as Read Time varies for three combinations of temperature and hematocrit in the test of Example 5.

The measurement results illustrated in FIG. 18 show the correlation coefficient $r^2$ between the DC current response and the glucose level as the Read Time varies for three combinations of temperature and hematocrit. These results demonstrate that a robust DC response should be anticipated for tests as fast as 1 second. However, those skilled in the art will recognise that there are undesirable variations in the sensor accuracy (correlation) due to the interfering effects of temperature and hematocrit levels, suggesting that the combined AC and DC measurement method of the present invention should produce more closely correlated results.

Figure 19:
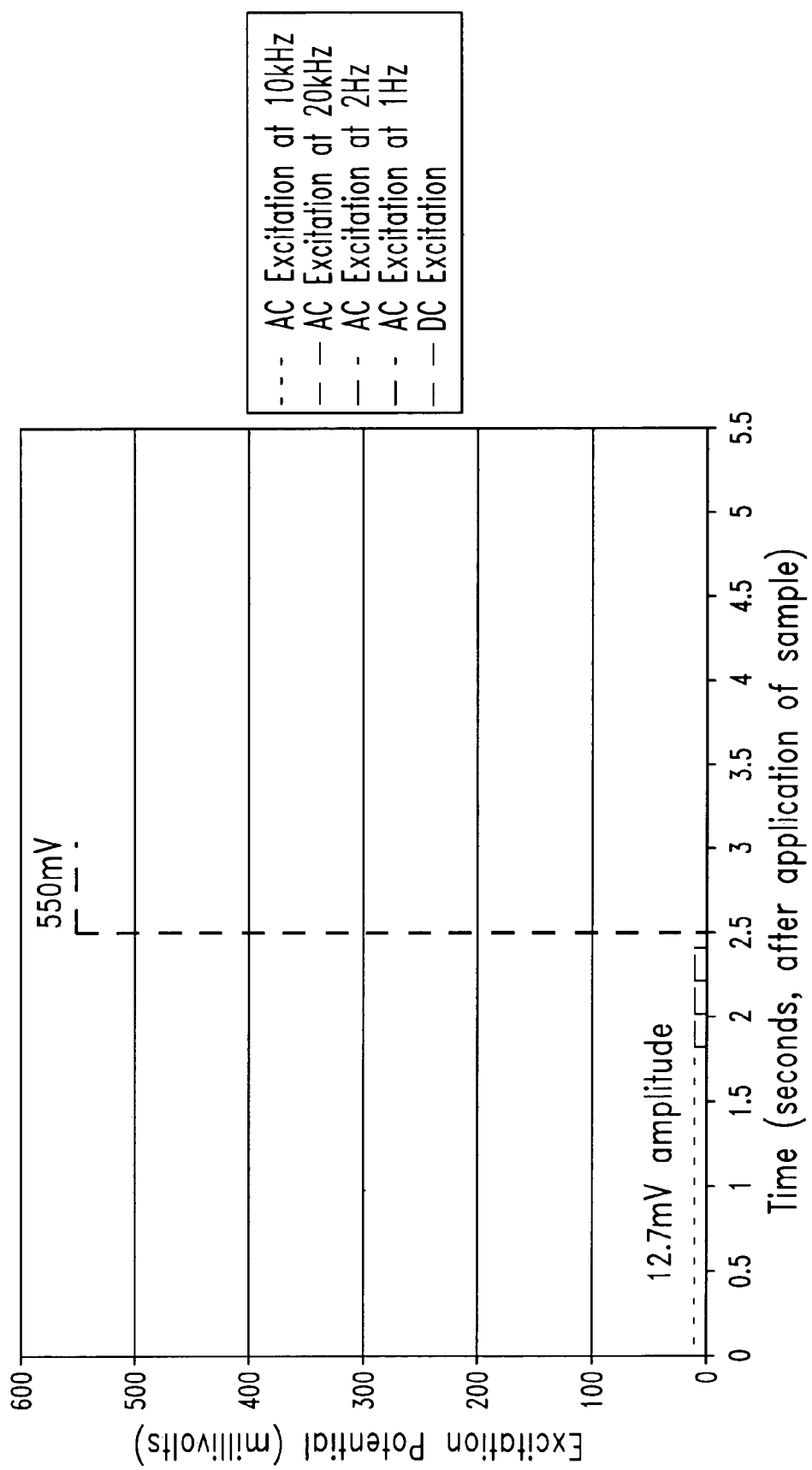
FIG. 19 is a diagram of the excitation signal utilized in the test of Example 5.

Based upon the encouraging results obtained in FIG. 18, a further test was designed using the excitation signal of FIG. 19 applied to the test strip 1700. The excitation comprised a 10 kHz AC signal applied for approximately 1.8 seconds, a 20 kHz AC signal applied for approximately 0.2 seconds, a 2 Hz AC signal applied for approximately 0.2 seconds, a 1 Hz AC signal applied for approximately 0.2 seconds, and a DC signal applied for approximately 0.5 seconds. The AC signals had an amplitude of 12.7 mV peak, while the DC signal had an amplitude of 550 mV. The Total Test Time was 3.0 seconds.

Figure 20:
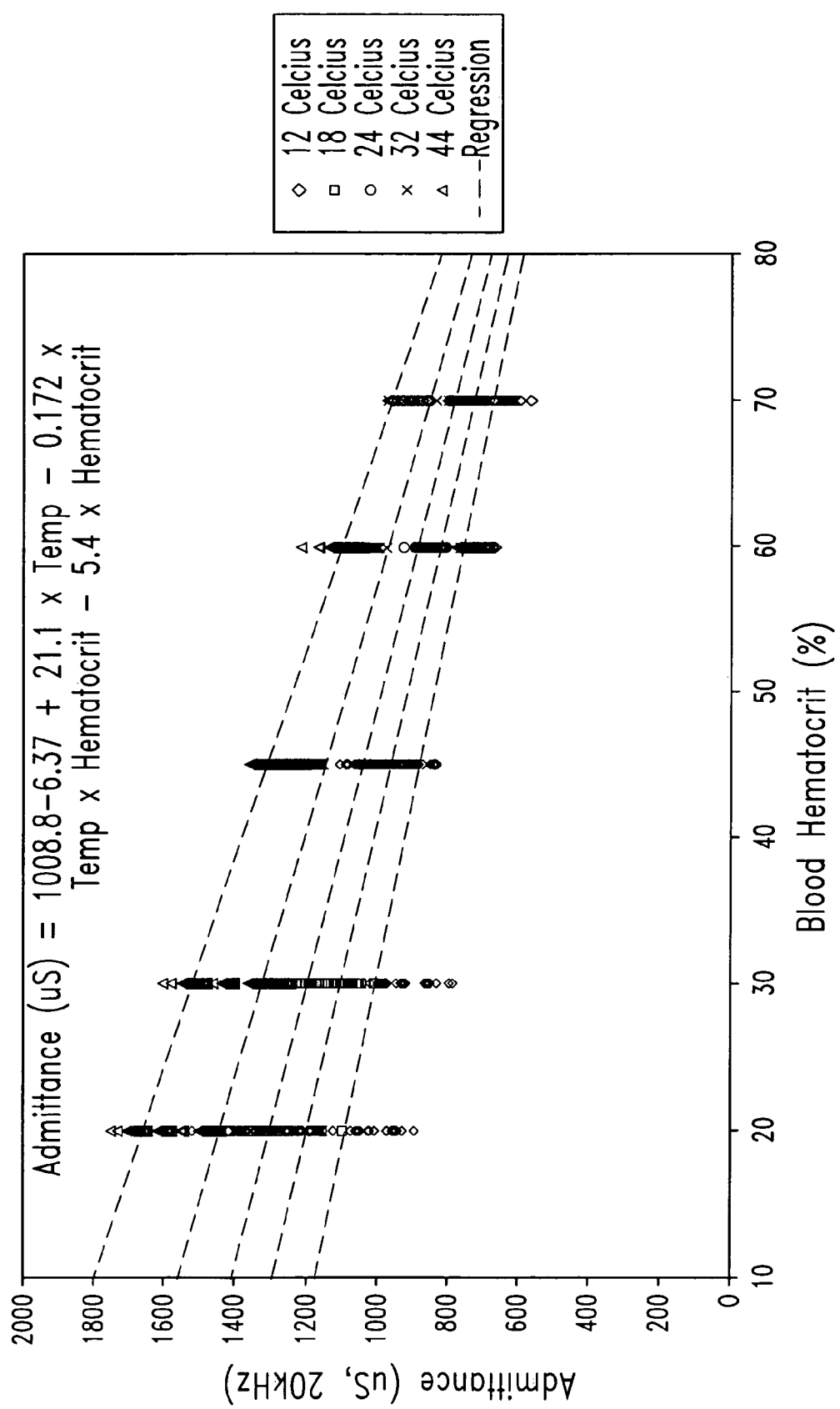
FIG. 20 is a plot of AC admittance versus hematocrit as temperature is parametrically varied in the test of Example 5.
Figure 21:
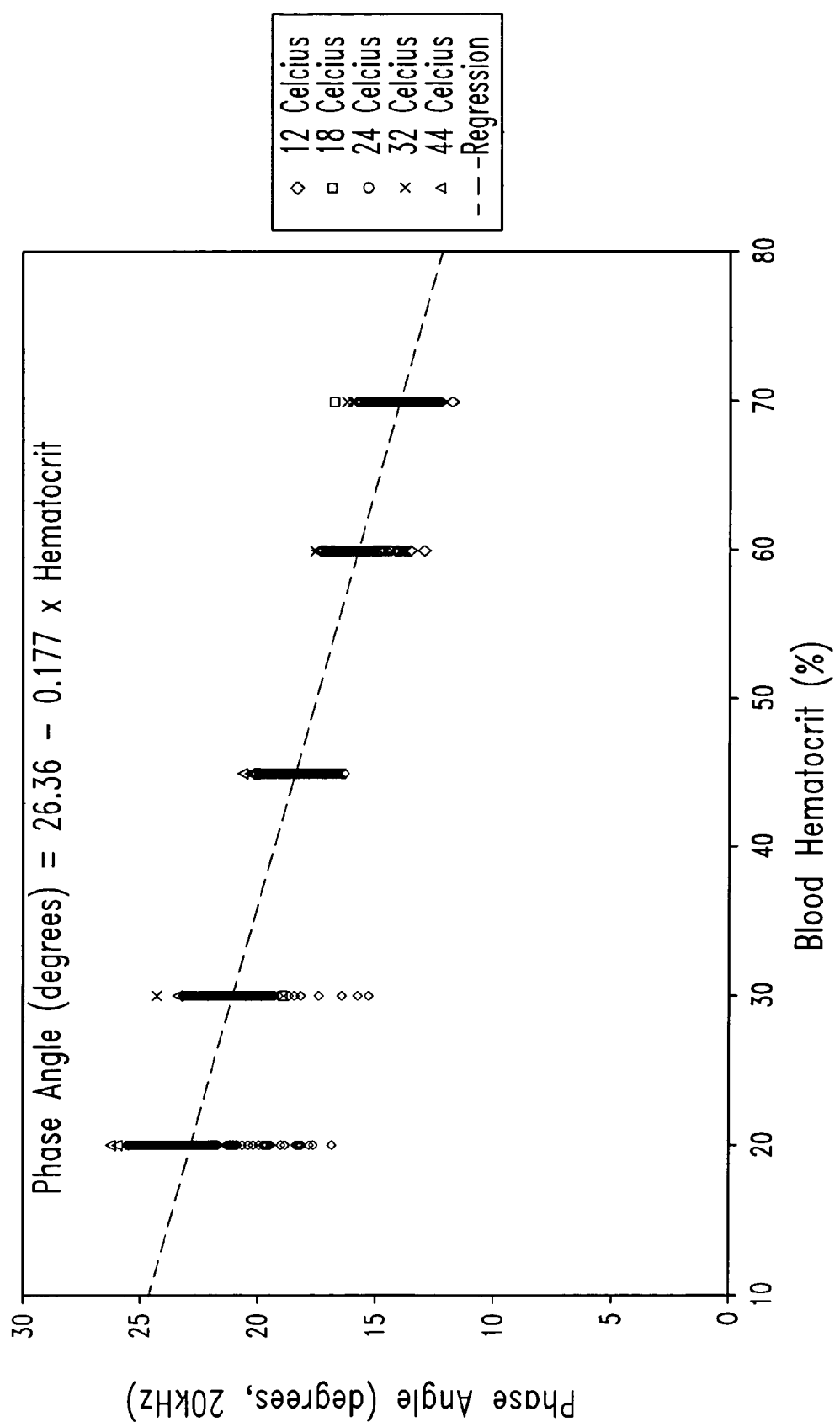
FIG. 21 is a plot of AC admittance phase angle versus hematocrit as temperature is parametrically varied in the test of Example 5.

A covariance study using spiked venous blood samples representing five glucose levels (40, 120, 200, 400 and 600), five hematocrit levels (20, 30, 45, 60 and 70%) and five temperatures (12, 18, 24, 32 and 44° C.) was designed, resulting in 125 separate combinations. As in the previous examples, the relationship between admittance, temperature and hematocrit was examined and plotted (FIG. 20 shows the admittance at 20 kHz versus hematocrit as temperature varies) and it was confirmed that the admittance was linearly related to hematocrit in a temperature dependent manner. An additional discovery, however, was that the phase angle of the AC response was correlated with hematocrit in a temperature independent manner. The phase angle of the 20 kHz AC response is plotted versus hematocrit in FIG. 21. The results for phase angle measured at 10 kHz are similar. The hematocrit of the blood sample may therefore be reliably estimated using only the phase angle information as follows:

$$H_{est}=c_0+c_1(\Phi_{10\,kHz}-\Phi_{20\,kHz})+c_2(\Phi_{2\,kHz}-\Phi_{1\,kHz}) \quad \text{(Equation 11)}$$

For the test strip used in this Example 5, the correlation between phase angle and hematocrit was better at higher frequencies. Because of this, the $c_2$ constant approaches zero and $H_{est}$ can reliably be estimated using only the 10 kHz and 20 kHz data. Use of lower frequencies, however, allows for slight improvements in the strip-to-strip variability of the $H^{est}$ function. The present invention therefore may be used to estimate hematocrit using only AC phase angle measurements preferably made at at least one AC frequency, more preferably made at at least two AC frequencies, and most preferably made at at least four AC frequencies.

Because the hematocrit can be determined using only the AC response data, and we know from FIG. 20 that admittance is linearly related to hematocrit and temperature, we can now determine the temperature of the sample under analysis using only the AC response as follows:

$$T_{est}=b_0+b_1(Y_{10\,kHz}-Y_{20\,kHz})+b_2(Y_{2\,kHz}-Y_{1\,kHz})+b_3H_{est} \quad \text{(Equation 12)}$$

where $b_0$, $b_1$, $b_2$ and $b_3$ are constants. It will be appreciated that the estimation of hematocrit and temperature from the AC response data may be made with more or fewer frequency measurements, and at different frequencies than those chosen for this example. The particular frequencies that produce the most robust results will be determined by test strip geometries and dimensions. The present invention therefore may be used to estimate test sample temperature using only AC response measurements preferably made at at least one AC frequency, more preferably made at at least two AC frequencies, and most preferably made at at least four. AC frequencies.

Those skilled in the art will recognise that the direct measurement of the temperature of the sample under test (by means of the AC response) is a great improvement over prior art methods for estimating the temperature of the sample. Typically, a thermistor is placed in the test meter near where the test strip is inserted into the meter. Because the thermistor is measuring a temperature remote from the actual sample, it is at best only a rough approximation of the true sample temperature. Furthermore, if the sample temperature is changing (for example due to evaporation), then the thermal inertia of the test meter and even the thermistor itself will prevent the meter-mounted thermistor from accurately reflecting the true temperature of the sample under test. By contrast, the temperature estimation of the present invention is derived from measurements made within the sample under test (i.e. within the reaction zone in which the sample under test reacts with the reagent), thereby eliminating any error introduced by the sample being remote from the measuring location. Additionally, the temperature estimation of the present invention is made using data that was collected very close in time to the glucose measurement data that will be corrected using the temperature estimation, thereby further improving accuracy. This represents a significant improvement over the prior art methods.

Figure 22:
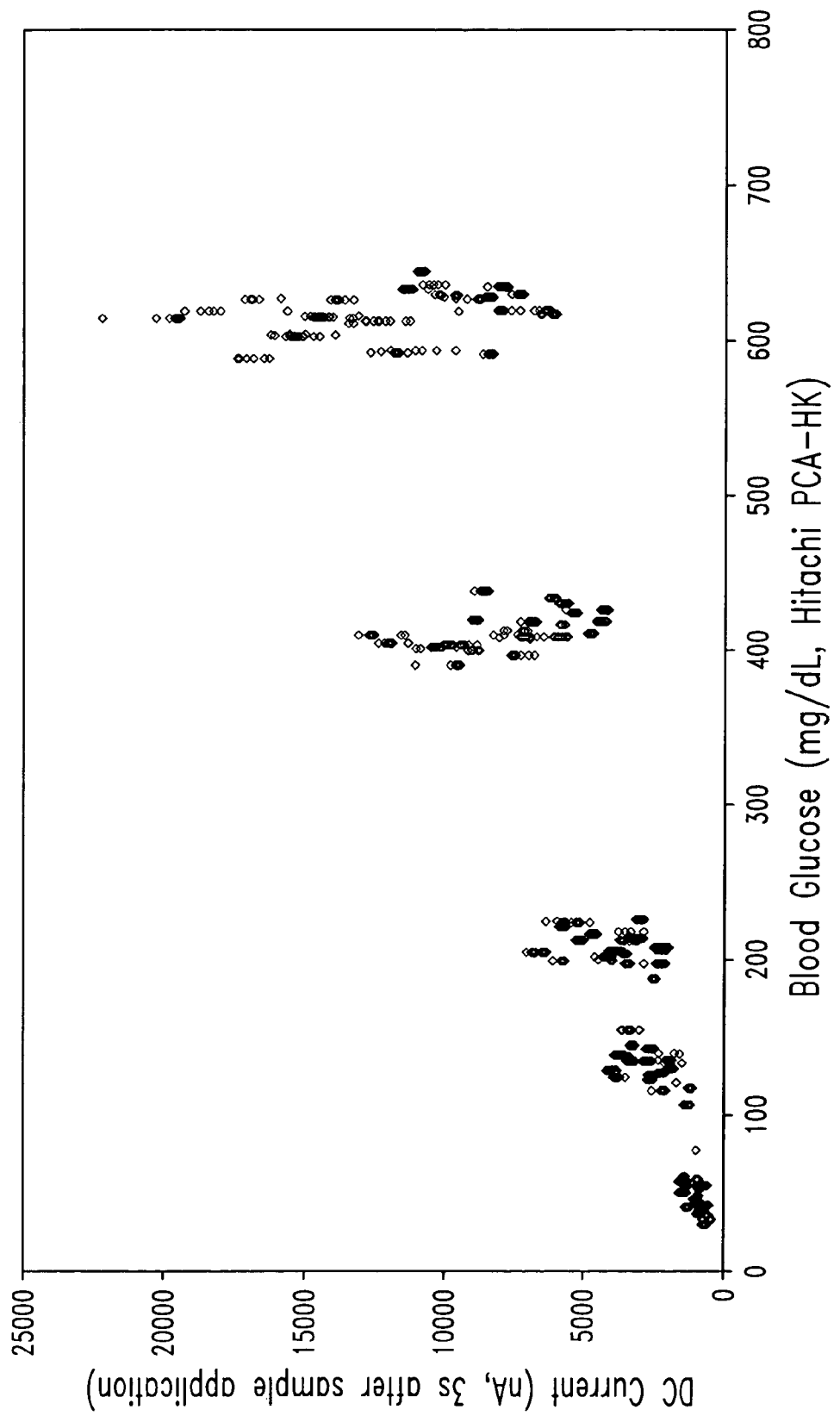
FIG. 22 is a plot of the uncompensated DC response versus actual glucose for the test of Example 5.

As a demonstration of the effectiveness of the method of this Example 5 for correcting for the effects of interferants on the blood glucose measurement, the uncompensated DC current response versus known glucose concentration is plotted in FIG. 22 for all 125 combinations of glucose, temperature and hematocrit (the AC measurements were ignored when plotting this data). As will be appreciated by those skilled in the art, the data exhibits huge variation with respect to hematocrit and temperature.

As previously discussed, the accuracy of the DC glucose response can be greatly improved by combining the estimated hematocrit, temperature and DC response to correct for the hematocrit and temperature interference in the DC response as follows:

$$\text{PRED} = (a_0 + hct_1 H_{est} + hct_2 H_{est}^2 + tau_1 T_{est} + tau_2 T_{est}) + (a_1 \text{DC})(1 + hct_3 H_{est} + hct_4 H_{est}^2)(1 + tau_3 T_{est} + tau_4 T_{est}) \quad \text{(Equation 13)}$$

The constants in Equation 13 can be determined using regression analysis, as is known in the art. The present invention therefore allows one to estimate hematocrit by using the AC phase angle response (Equation 11). The estimated hematocrit and the measured AC admittance can be used to determine the estimated temperature (Equation 12). Finally, the estimated hematocrit and estimated temperature can be used with the measured DC response to obtain the predicted glucose concentration (Equation 13).

Figure 23:
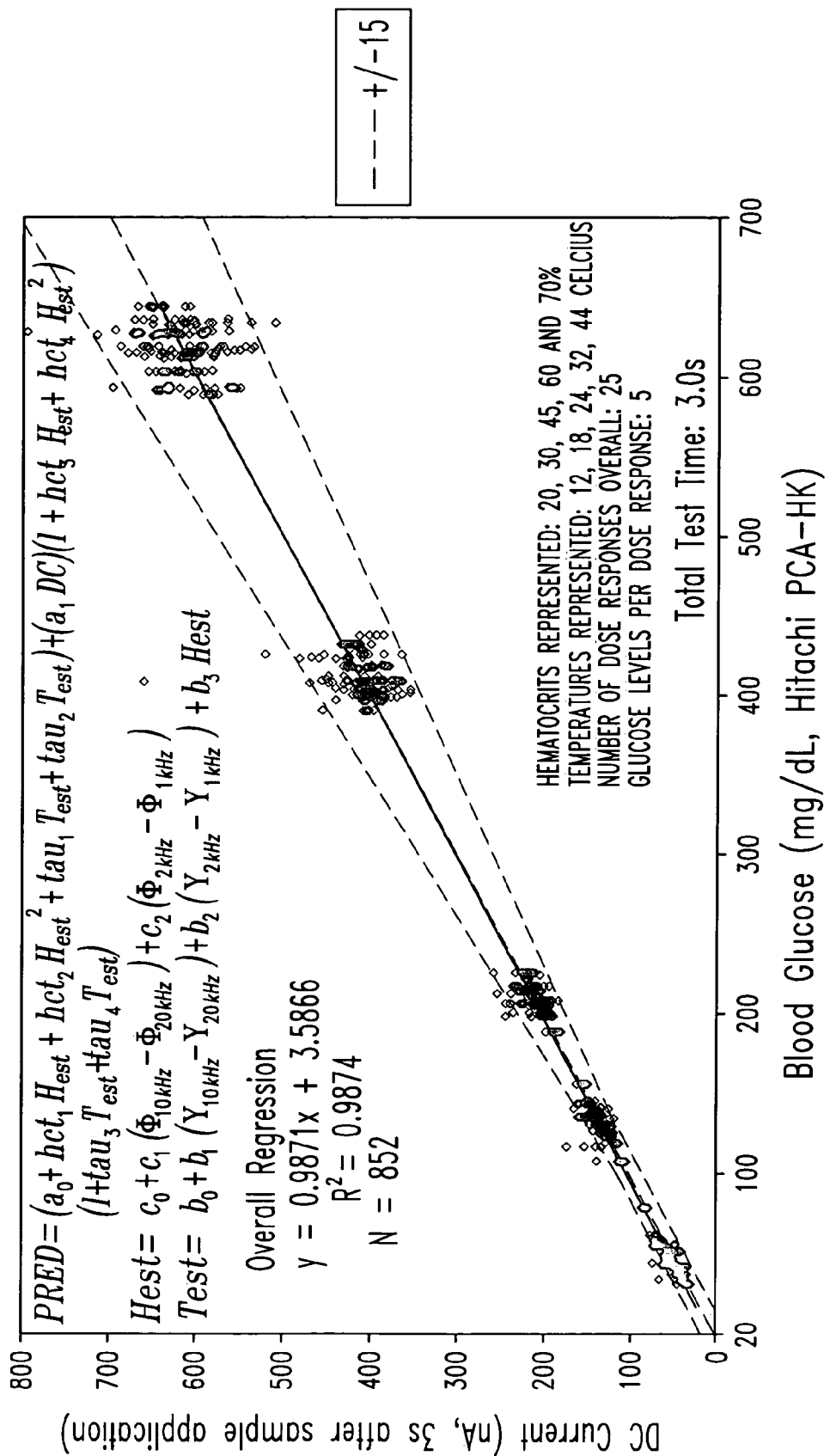
FIG. 23 is a plot of the predicted glucose response versus actual glucose response for the test of Example 5.

Applying the above methodology to the test data plotted in FIG. 22, we obtain the predicted glucose versus DC current response illustrated in FIG. 23. This data represents 125 covariant samples having hematocrit levels ranging from 20%-70% and temperatures ranging from 12° C.-44° C. Even with these wide variations in interferant levels, the measurement method of the present invention produced an overall $r^2$ correlation of 0.9874 using a 3.0 second Total Test Time.

EXAMPLE 6

Simultaneous AC and DC Measurement Using a 0.397 µl Sample

Figure 24:
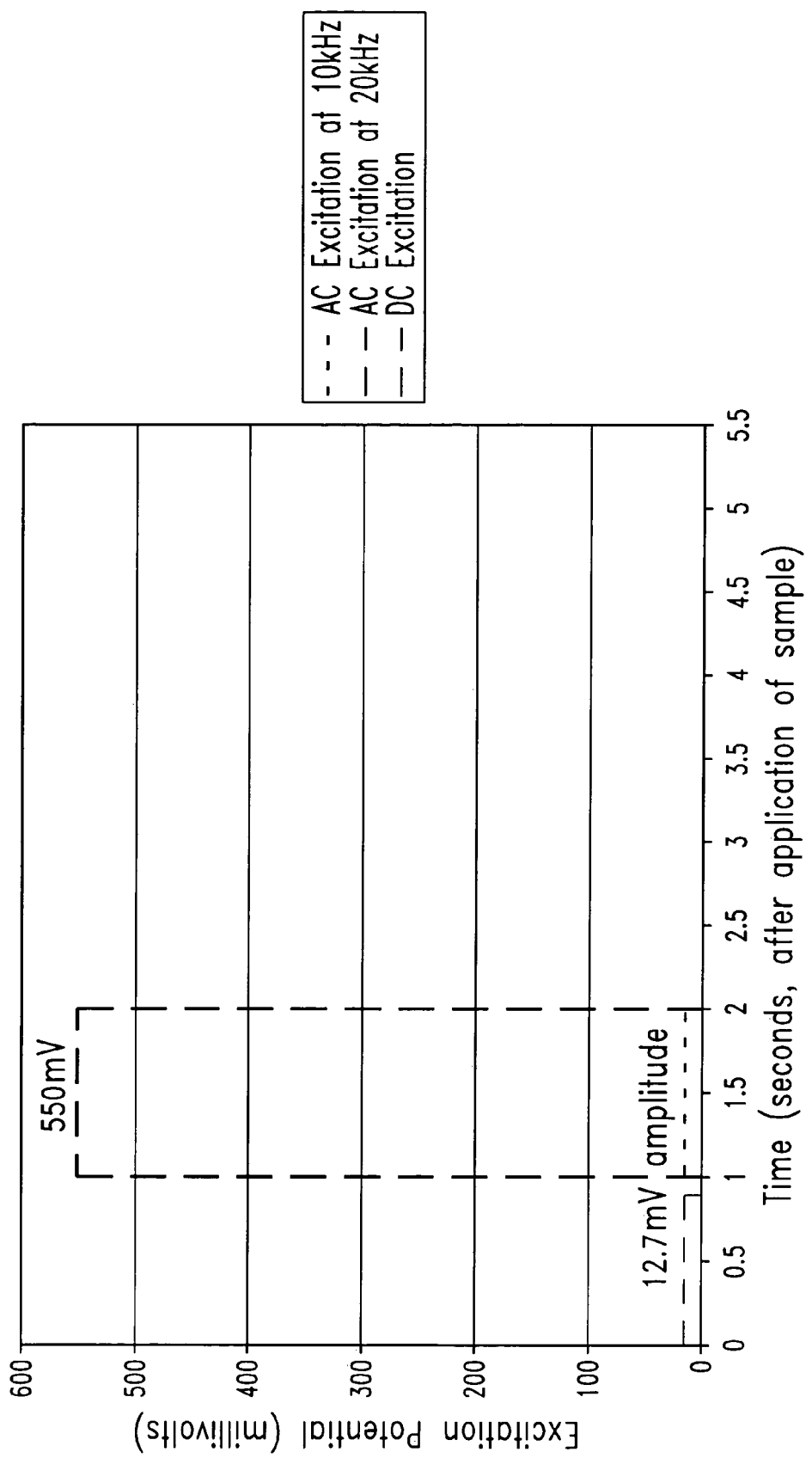
FIG. 24 is a diagram of the excitation signal utilized in the test of Example 6.

Using the same test strip 1700 and reagent described above for Example 5, the excitation profile illustrated in FIG. 24 was utilized in order to decrease the Total Test Time. As described above with respect to Example 5, it was determined that the phase angle at 20 kHz and at 10 kHz were most closely correlated with the hematocrit estimation. It was therefore decided to limit the AC portion of the excitation to these two frequencies in Example 6 in order to decrease the Total Test Time. In order to make further reductions in Total Test Time, the 10 kHz AC excitation was applied simultaneously with the DC signal (i.e. an AC signal with a DC offset), the theory being that this combined mode would allow for the collection of simultaneous results for DC current, AC phase and AC admittance, providing the fastest possible results. Therefore, the 20 kHz signal was applied for 0.9 seconds. Thereafter, the 10 kHz and DC signals were applied simultaneously for 1.0 second after a 0.1 second interval.

Figure 25:
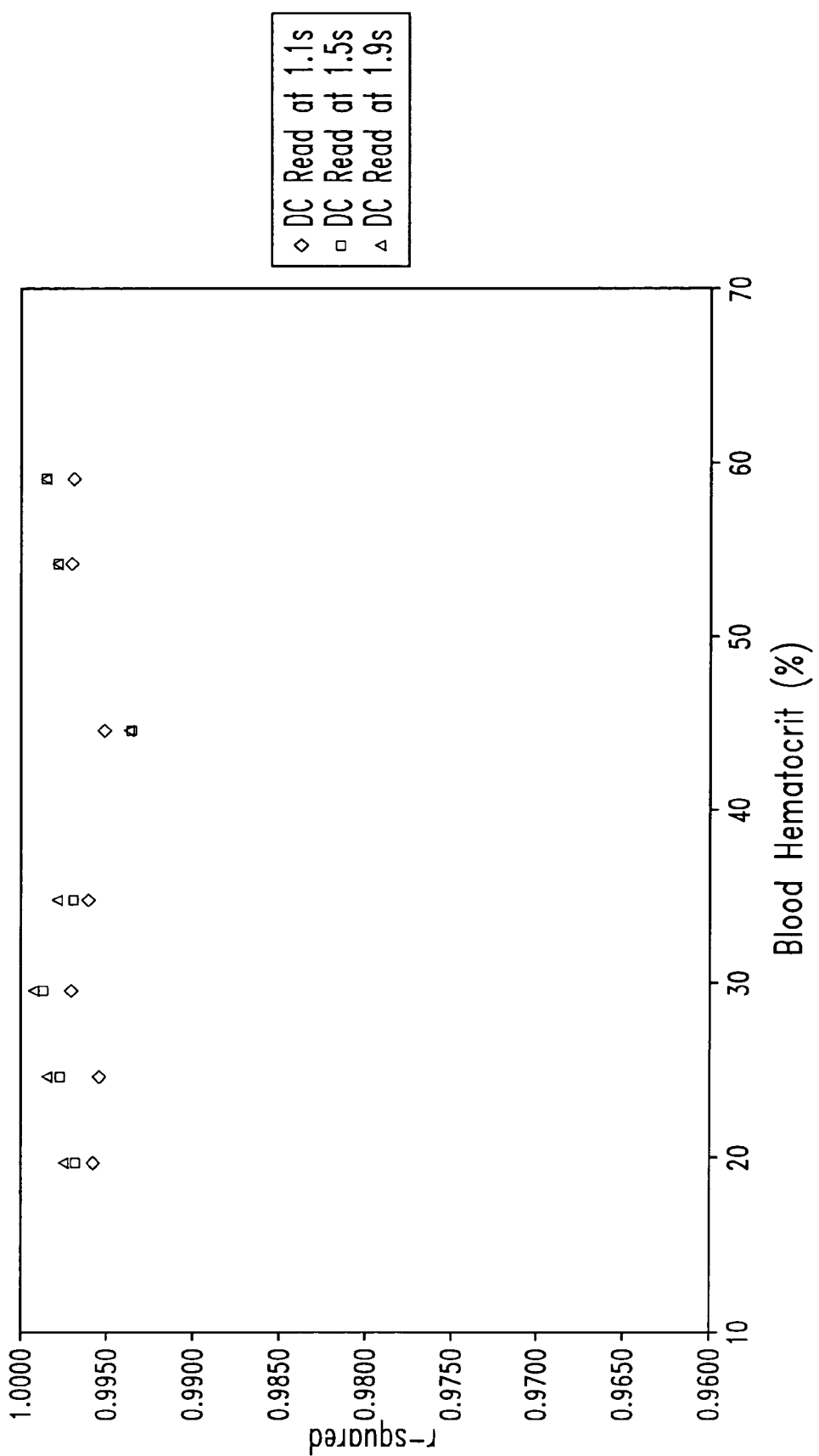
FIG. 25 is a plot of the correlation coefficient $r^2$ between hematocrit and DC response current plotted against hematocrit in the test of Example 6.

For this Example 6, 49 spiked venous blood samples representing seven glucose levels and seven hematocrit levels were tested. The correlation coefficient $r^2$ between the DC current and the blood hematocrit was then examined at three DC measurement times: 1.1 seconds, 1.5 seconds and 1.9 seconds after sample application. These correlations are plotted versus hematocrit level in FIG. 25. All of these results are comparable, although the correlation is generally poorest at 1.1 seconds and generally best at 1.5 seconds. The minimum correlation coefficient, however, exceeds 0.99.

Figure 26:
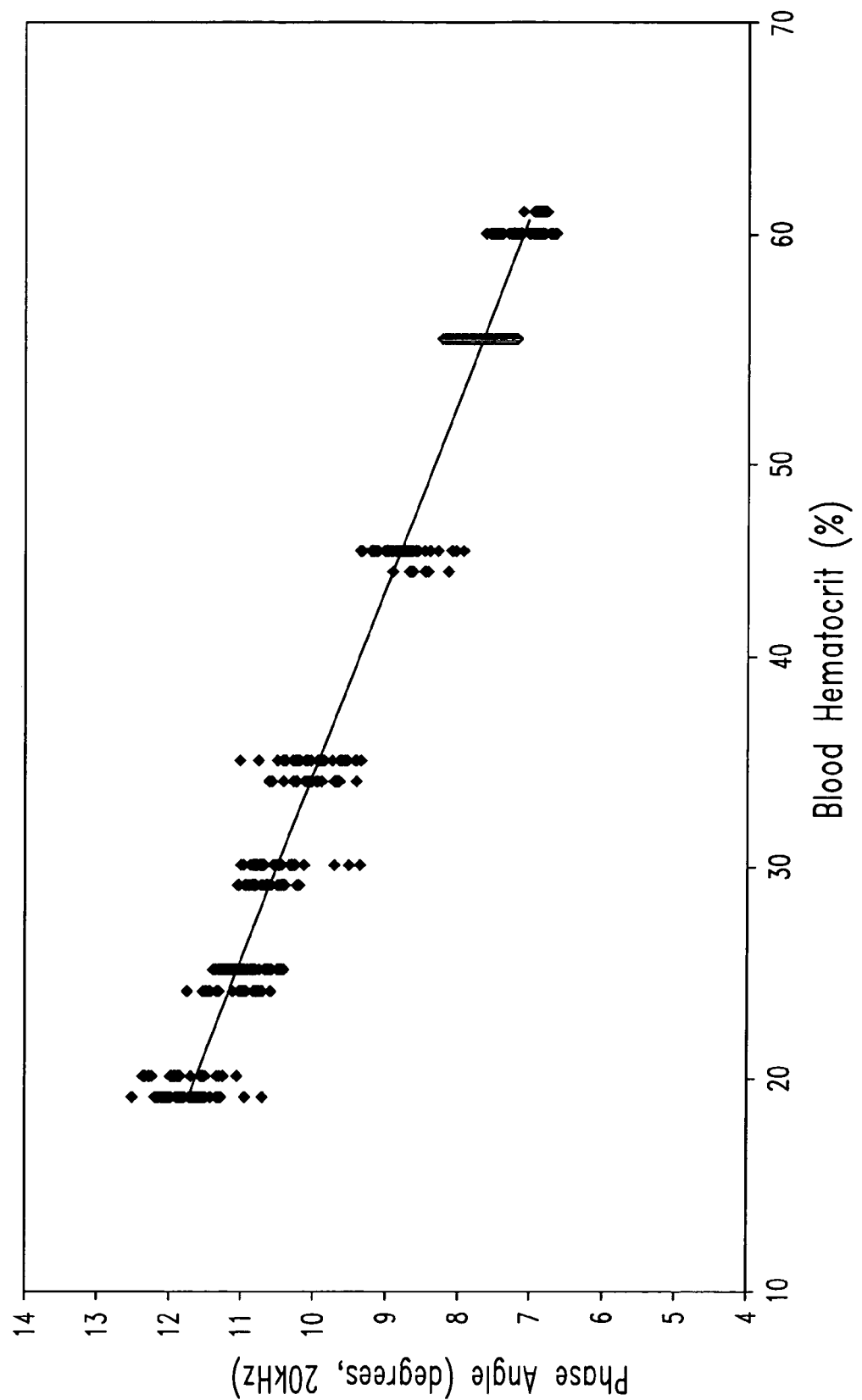
FIG. 26 is a plot of AC admittance phase angle versus hematocrit for the test of Example 6.

FIG. 26 illustrates the phase angle at 20 kHz plotted against hematocrit levels. The correlation between these two sets of data is very good, therefore it was decided that the 10 kHz data was unnecessary for estimating hematocrit. The hematocrit can therefore be estimated solely from the 20 kHz phase angle data as follows:

$$H_{est} = c_0 + c_1 \Phi_{20 kHz} \quad \text{(Equation 14)}$$

Figure 27:
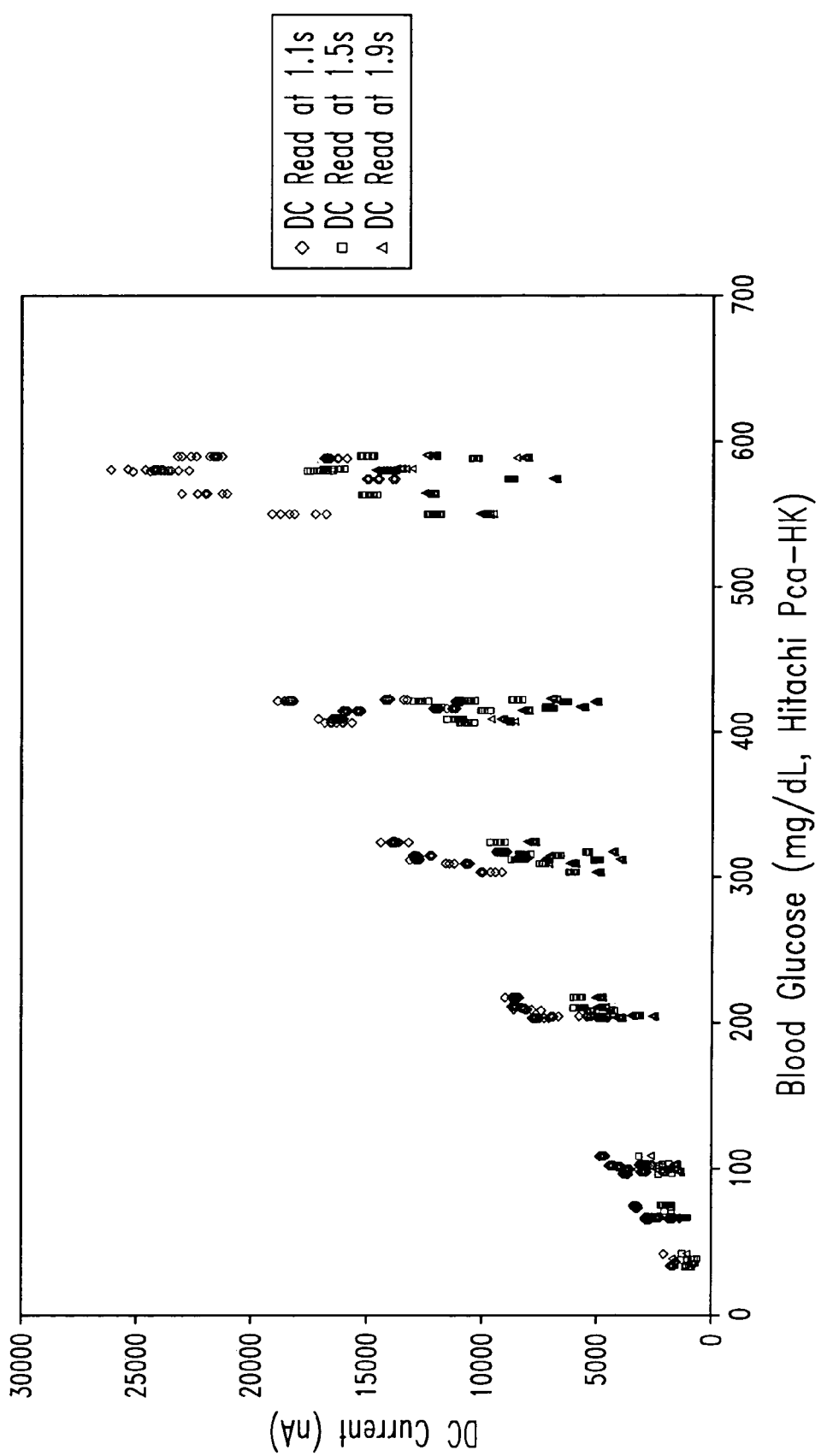
FIG. 27 is a plot of the uncompensated DC response versus actual glucose for the test of Example 6.

FIG. 27 illustrates the DC current response versus glucose level for all measured hematocrit levels as the read time is varied between 1.1 seconds, 1.5 seconds and 1.9 seconds. Not surprisingly, the DC current at 1.1 seconds is greater than the DC current at 1.5 seconds, which is greater than the DC current at 1.9 seconds. Those skilled in the art will recognise that the hematocrit level has a large effect on the DC current, particularly at high glucose concentrations.

As discussed hereinabove, the accuracy of the DC glucose response can be greatly improved by compensating for the interference caused by hematocrit as follows:

$$\text{PRED} = (a_0 + hct_1 H_{est} + hct_2 H_{est}^2) + (a_1 \text{DC})(1 + hct_3 H_{est} + hct_4 H_{est}^2) \quad \text{(Equation 15)}$$

Figure 28:
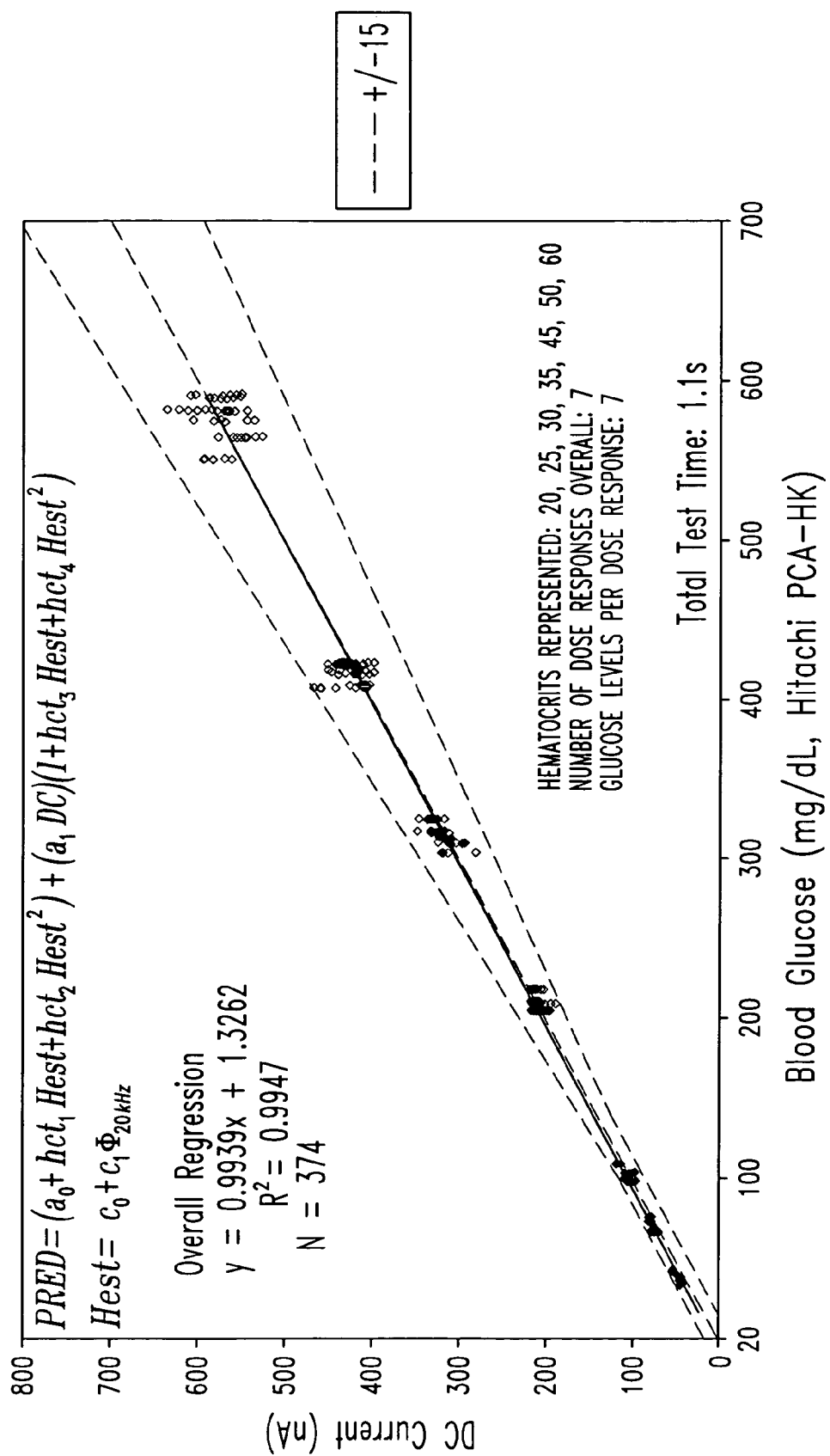
FIG. 28 is a plot of the compensated DC response versus actual glucose for a 1.1 second Total Test Time of Example 6.

Note that Equation 15 does not include temperature compensation terms since temperature variation was not included in the experiment of this Example 6, it can be reasonably inferred from previous examples that a Test term could be included using the 10 kHz and 20 kHz admittance values in combination with the $H_{est}$ term. Because the hematocrit can be reliably estimated using only the 20 kHz phase angle measurement data, the hematocrit compensated predicted glucose response can be determined using only this phase angle information and the measured DC response. The compensated DC response versus glucose level for only the DC read at 1.1 seconds (representing a 1.1 second Total Test Time) is illustrated in FIG. 28. The data shows an overall $r^2$ correlation of 0.9947 with a 1.1 second Total Test Time.

Figure 29:
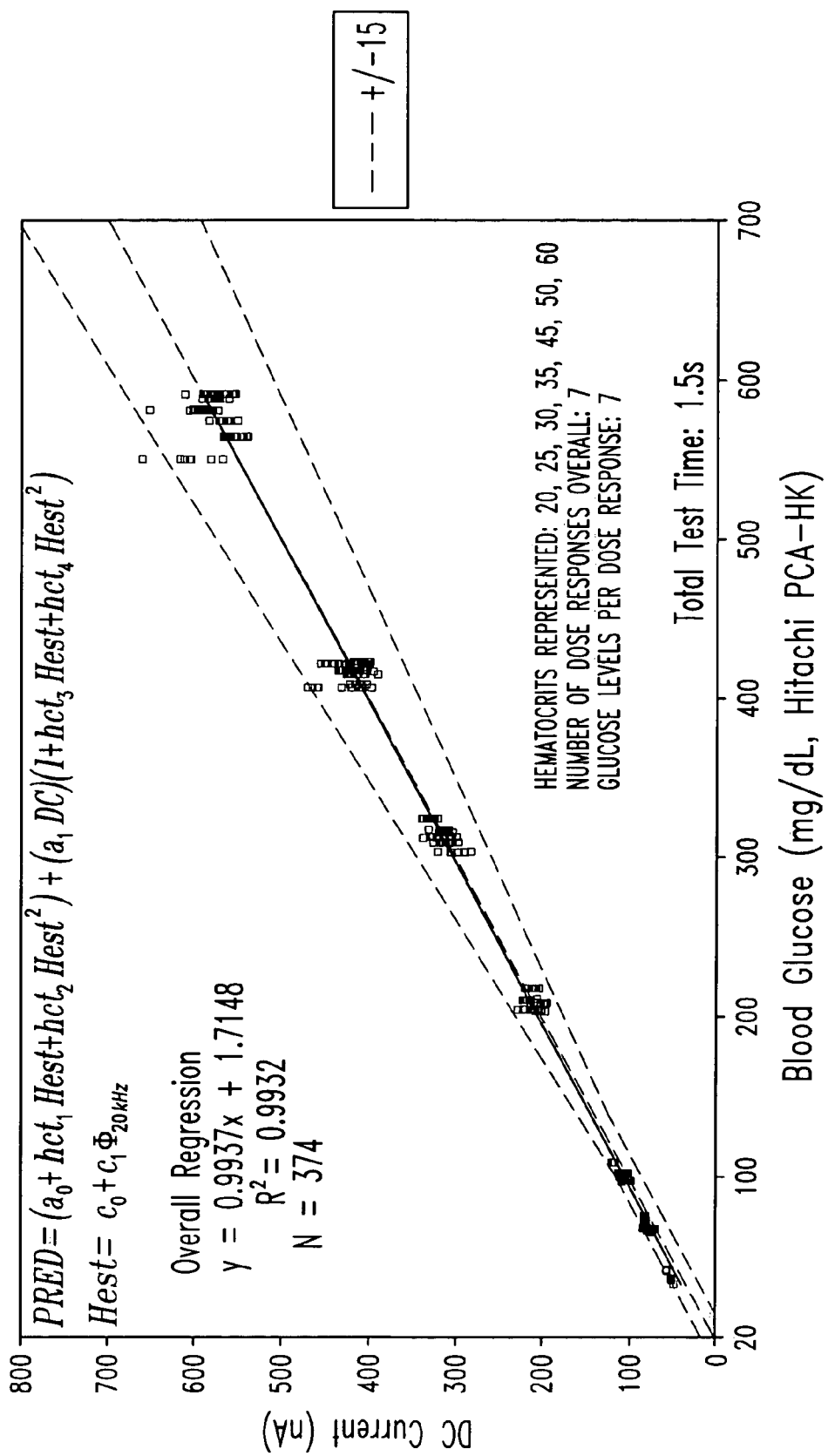
FIG. 29 is a plot of the compensated DC response versus actual glucose for a 1.5 second Total Test Time of Example 6.
Figure 30:
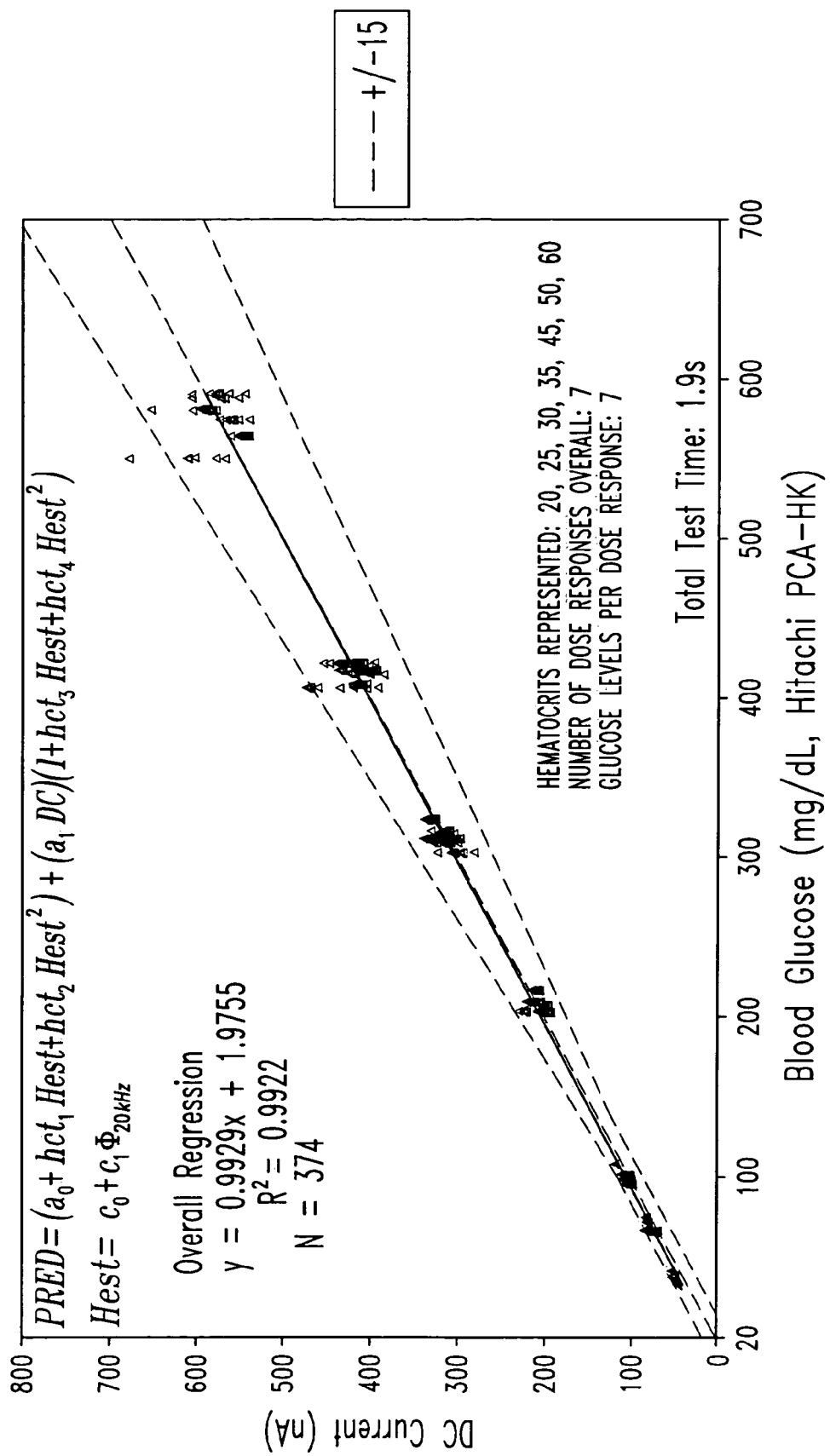
FIG. 30 is a plot of the compensated DC response versus actual glucose for a 1.9 second Total Test Time of Example 6.

The same data for the 1.5 second DC read is illustrated in FIG. 29, showing an overall $r^2$ correlation of 0.9932 for a 1.5 second Total Test Time. The same data for the 1.9 second DC read is illustrated in FIG. 30, showing an overall $r^2$ correlation of 0.9922 for a 1.9 second Total Test Time. Surprisingly, the $r^2$ correlation actually decreased slightly with the longer test times. Notwithstanding this, the correlation coefficients for all three compensated data sets—where all 7 hematocrits ranging from 20% through 60% are combined—were in excess of 0.99, demonstrating the applicability of the present invention to yield a blood glucose test as fast as 1.1 seconds, combined with improved accuracy, where the sensor requires less than 0.4 microliters of blood in order to perform the glucose measurement test.

EXAMPLE 7

Use of AC Phase Angle to Detect an Abused Sensor

In order to provide an extra measure of quality control to the analyte measurement process, particularly when the test system is to be used by a non-professional end user, it is desirable to detect sensors (test strips) that have been misdosed (double dosed, etc.), that have been previously used, or that have degraded enzymes (from being stored in too humid an environment, being too old, etc.). These conditions are collectively referred to as "abused sensors." It is desired to devise a test that will abort the analyte measurement process (or at least warn the user that the test results may not be accurate) if an abused sensor is inserted into the test meter.

When performing a blood glucose analysis, the test meter will typically make several successive current measurements as the blood sample continues to react with the reagent chemistry. As is well known in the art, this response current is known as the Cottrell current and it follows a pattern of decay as the reaction progresses. We may define a Cottrell Failsafe Ratio (CFR) as follows:

The Cottrell response of the biosensor in the Confidence system can be given by:

$$I_{cottrell} = \frac{nFA\sqrt{D}}{\sqrt{n}} Ct^\alpha \quad \text{(Equation 16)}$$

where:
n=electrons freed per glucose molecule
F=Faraday's Constant
A=Working electrode surface area
t=elapsed time since application of excitation
D=diffusion coefficient
C=glucose concentration
α=a cofactor-dependent constant.

All of the parameters of this equation will normally be constant for the sensor except the glucose concentration and time. We can therefore define a normalized Cottrell failsafe ratio (NCFR) as:

$$NCFR = \frac{\sum_{k=1}^{m} I_k}{mI_m} = \frac{\sum_{k=1}^{m} \frac{nFA\sqrt{D}}{\sqrt{\Pi}} Ct_k^\alpha}{m \frac{nFA\sqrt{D}}{\sqrt{\Pi}} Ct_m^\alpha} = \frac{\sum_{k=1}^{m} t_k^\alpha}{mt_m^\alpha} = \text{Constant} \quad \text{(Equation 17)}$$

As the time terms in this equation are known and constant for a sensor measurement, the ratio always yields a constant for Cottrell curves with identical sample times and intervals. Therefore, the sum of sensor currents divided by the last sensor current should yield a constant independent of glucose concentration. This relationship is used in the preferred embodiment to detect potentially faulty biosensor responses.

A Current Sum Failsafe can be devised that places a check on the Cottrell response of the sensor by summing all of the acquired currents during sensor measurement. When the final current is acquired, it is multiplied by two constants (which may be loaded into the meter at the time of manufacture or, more preferably, supplied to the meter with each lot of sensors, such as by a separate code key or by information coded onto the sensor itself). These constants represent the upper and lower threshold for allowable NCFR values.

The two products of the constants multiplied by the final current are compared to the sum of the biosensor currents. The sum of the currents should fall between the two products, thereby indicating that the ratio above was fulfilled, plus or minus a tolerance.

Therefore, the preferred embodiment performs the following check when there is a single DC block:

$$(I_m)(C_l) \leq \sum_{k=1}^{m} I_k \leq (I_m)(C_u) \quad \text{(Equation 18)}$$

where
$C_u$=upper constant from the Code Key
$C_l$=lower constant from the Code Key
$I_m$=final biosensor current Because some embodiments may contain two DC blocks in the measurement sequence, a Modified Cottrell Failsafe Ratio (MCFR) can be formulated as:

$$MCFR = \frac{w_1 NCFR_1 + w_2 NCFR_2}{w_1 + w_2} \quad \text{(Equation 19)}$$

where
$w_1, w_2$=weighting constants (e.g. from the Code Key)
$NCFR_1, NCFR_2$=the Normalized Cottrell Failsafe Ratios for DC blocks 1 and 2 respectively.

Therefore, the preferred embodiment performs the following check when there are two DC blocks:

$$(w_1 + w_2)I_{m_1}I_{m_2}C_L \leq \\ \left( w_1 I_{m_2} \sum_{k=1}^{m_1} I_k + w_2 I_{m_1} \sum_{k=1}^{m_2} I_k \right) \leq (w_1 + w_2)I_{m_1}I_{m_2}C_u \quad \text{(Equation 20)}$$

where
$C_u$=upper constant from the Code Key
$C_L$=lower constant from the Code Key
$I_{m1}, I_{m2}$=final biosensor current in DC blocks 1 and 2

The NCFR (and MCFR) is correlated with hematocrit. As demonstrated hereinabove in Example 3, the AC phase angle is also correlated with hematocrit. It follows then, that the AC phase angle and the NCFR are correlated with one another. This relationship holds only if the sensor is unabused. The correlation degrades for an abused sensor.

It is therefore possible to design an equation to analyze the measured phase angle data to produce a failsafe calculation that will indicate if an abused sensor is being used. In the preferred embodiment, it was chosen to use the difference between the phase angles measured at two separate frequencies in order to make the test more robust to errors caused by parasitic resistance, etc. Applying the arctangent function to drive the two populations to different asymptotes yields the following failsafe equation:

$$\text{FAILSAFE}=1000\times\arctan[NCFR/(fs_0+fs_1(\Phi_{10\,kHz}-\Phi_{20\,kHz}))] \quad \text{(Equation 21)}$$

where
1000=scaling factor
NCFR=Cottrell Failsafe Ratio
$fs_0$=linear regression intercept
$fs_1$=linear regression slope
$\Phi_{10\,kHz}$=phase angle at 10 kHz
$\Phi_{20\,kHz}$=phase angle at 20 kHz Using Equation 21, the intercept term $fs_0$ can be chosen such that a FAILSAFE value below zero indicates an abused sensor, while a FAILSAFE value above zero indicates a nonabused sensor. Those skilled in the art will recognise that the opposite result could be obtained by choosing a different intercept.

Use of Dose Sufficiency Electrodes

As described hereinabove, it has been recognised that accurate sample measurement requires adequate coverage of the measurement electrodes by the sample. Various methods have been used to detect the insufficiency of the sample volume in the prior art. For example, the Accu-Chek® Advantage® glucose test meter sold by Roche Diagnostics Corporation of Indianapolis, Ind. warned the user of the possible inadequacy of the sample volume if non-Cotrellian current decay was detected by the single pair of measurement electrodes. Users were prompted to re-dose the test strip within a specified time allotment.

The possibility of insufficient sample size has been heightened in recent years due to the use of capillary fill devices used in conjunction with blood lancing devices designed to minimize pain through the requirement of only extremely small sample volumes. If an inadequate amount of sample is drawn into the capillary fill space, then there is a possibility that the measurement electrodes will not be adequately covered and the measurement accuracy will be compromised. In order to overcome the problems associated with insufficient samples, various prior art solutions have been proposed, such as placing an additional electrode downstream from the measurement electrodes; or a single counter electrode having a sub-element downstream and major element upstream of a working electrode; or an indicator electrode arranged both upstream and downstream from a measurement electrode (allowing one to follow the flow progression of the sample across the working and counter electrodes or the arrival of the sample at a distance downstream). The problem associated with each of these solutions is that they each incorporate one or the other electrode of the measurement pair in communication with either the upstream or the downstream indicator electrodes to assess the presence of a sufficient volume of sample to avoid biased test results.

Despite these prior art design solutions, failure modes persist wherein the devices remain prone to misinterpretation of sample sufficiency. The present inventors have determined that such erroneous conclusions are related primarily to the distances between a downstream member of a measurement electrode pair (co-planar or opposing geometries) and the dose detection electrode, in combination with the diversity of non-uniform flow fronts. A sample traversing the capillary fill space having an aberrant (uneven) flow front can close the circuit between a measurement electrode and an indicator electrode and erroneously advise the system that sufficient sample is present to avoid a biased measurement result.

Many factors employed in the composition and/or fabrication of the test strip capillary fill spaces influence such irregular flow front behavior. These factors include:

disparities between surface energies of different walls forming the capillary fill space.

contamination of materials or finished goods in the test strip manufacturing facility.

unintentional introduction of a contaminant from a single component making up the walls of the capillary fill space (an example being a release agent (typically silicon) that is common to manufacturing processes wherein release liners are used).

hydrophobic properties of adhesives (or contaminated adhesives) used in the lamination processes.

disparate surface roughnesses on the walls of the capillary fill space.

dimensional aspect ratios.

contaminated mesh materials within the capillary fill space.

non-homogeneous application of surfactants onto mesh materials within the capillary fill space.

Another problem with prior art dose sufficiency methodologies determined by the present inventors relates to the use of one or the other of the available measurement electrodes in electrical communication with an upstream or downstream dose detection electrode. In such arrangements, the stoichiometry of the measurement zone (the area above or between the measurement electrodes) is perturbed during the dose detect/dose sufficiency test cycle prior to making a measurement of the analyte of interest residing in the measurement zone. As sample matrices vary radically in make-up, the fill properties of these samples also vary, resulting in timing differences between sample types. Such erratic timing routines act as an additional source of imprecision and expanded total system error metrics.

Trying to solve one or more of these obstacles typically can lead to 1) more complex manufacturing processes (additional process steps each bringing an additional propensity for contamination); 2) additional raw material quality control procedures; 3) more costly raw materials such as laminate composites having mixtures of hydrophobic and hydrophyllic resins and negatively impacting manufacturing costs; and 4) labor-intensive surfactant coatings of meshes and or capillary walls.

EXAMPLE 8

Determination of Fluid Flow Front Behavior in a Capillary Fill Space

In order to design an electrode system that will adequately indicate dose sufficiency in a test strip employing a capillary fill space, an experiment was performed to examine the flow front shape at the leading edge of the sample as it progresses through the capillary fill space. Test fixtures comprising two sheets of clear polycarbonate sheets joined together with double-sided adhesive tape were used, where the capillary fill space was formed by cutting a channel in the double-sided tape. Use of the polycarbonate upper and lower sheets allowed the flow fronts of the sample to be videotaped as it flowed through the capillary fill space.

Specifically, the test devices were laminated using laser cut 1 mm thick Lexan® polycarbonate sheets (obtained from Cadillac Plastics Ltd., Westlea, Swindon SN5 7EX, United Kingdom). The top and bottom polycarbonate sheets were coupled together using double-sided adhesive tapes (#200 MP High Performance acrylic adhesive obtained from 3M Corporation, St. Paul, Minn.). The capillary channels were defined by laser cutting the required width openings into the double-sided tape. Tape thicknesses of 0.05 µm, 0.125 µm, and 0.225 µm were used to give the required channel heights. The dimensions of the capillary spaces of the test devices are tabulated in FIG. 31.

The top and bottom polycarbonate parts were laminated together with the laser cut adhesive tapes using a custom-built jig to ensure reproducible fabrication. For each test device, a fluid receptor region defineing the entrance to the capillary channel was formed by an opening pre-cut into the upper polycarbonate sheet and adhesive tape components. For each of the three channel heights, channel widths of 0.5 mm, 1.00 mm, 1.5 mm, 2.00 mm, 3.00 mm, and 4.00 mm were fabricated. The capillary channel length for all devices was 50 mm. Twenty-eight (28) of each of the eighteen (18) device types were constructed. The assembled devices were plasma treated by Weidman Plastics Technology of Dortmund, Germany. The following plasma treatment conditions were used:
Processor: Microwave plasma processor 400
Microwave Power: 600 W
Gas: $O_2$
Pressure: 0.39 miilibar
Gas Flow: 150 ml/min
Time: 10 minutes
Surface Energy Pre-Treatment: <38 mN/m
Surface Energy Post-Treatment: 72 mN/m The plasma-treated devices were stored at 2-8° C. when not in use. The devices were allowed to equilibrate to room temperature for one (1) hour minimum before use.

Figure 31:
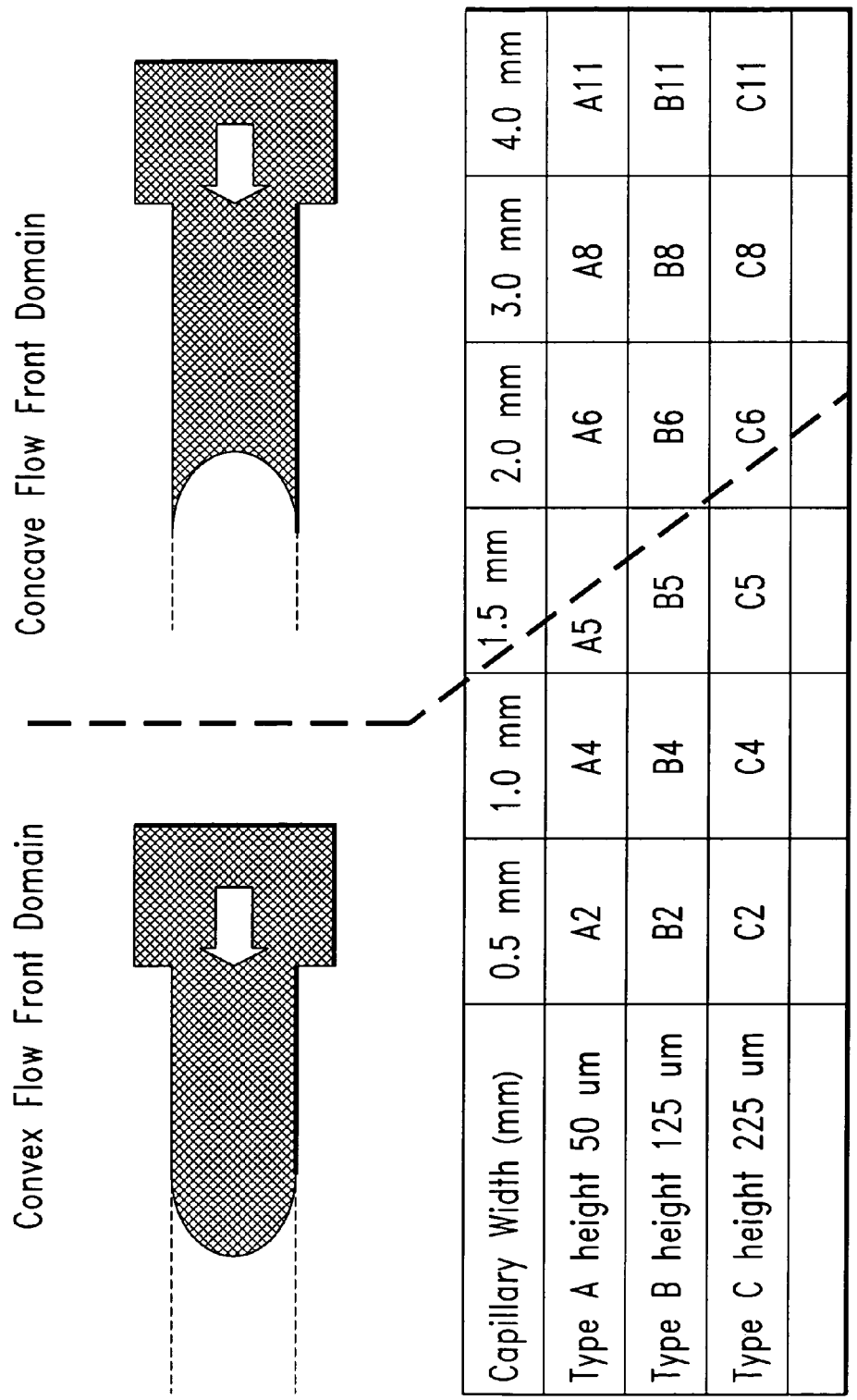
FIG. 31 is a table detailing the heights and widths of the capillary fill channels used in the test devices of Example 8, as well as schematic diagrams of convex and concave sample flow fronts in a capillary fill space.

Each of the test devices was dosed with a fixed volume of venous blood having a hematocrit value of 45%. Flow and flow front behavior was captured on videotape for later analysis. It was determined that the relative dimensions of the capillary fill channel determined the flow front behavior. Devices to the left of the dashed line in FIG. 31 (devices A2, A4, B2, B4, B5, C2, C4, and C5) resulted in a convex flow front behavior, while devices to the right of the dashed line (devices A6, A8, A11, B6, B8, B11, C6, C8, and C11) displayed a concave flow front behavior. Both the convex and concave flow front behaviors are schematically illustrated in FIG. 31. This data shows that the aspect ratio between the height and the width of the capillary fill space is a determining factor in whether the sample flow front is convex or concave.

Use of Dose Sufficiency Electrodes Cont'd

Figure 32A:
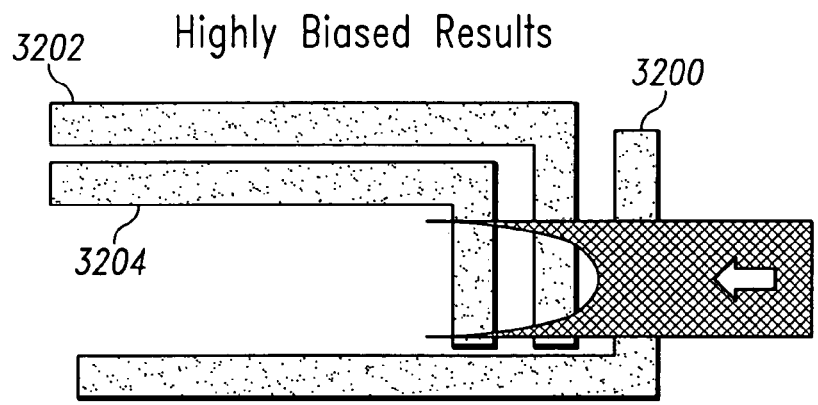
FIGS. 32A-C are schematic plan views of a test strip illustrating the potential for biased measurement results when a concave flow front encounters a prior art dose sufficiency electrode.
Figure 32B:
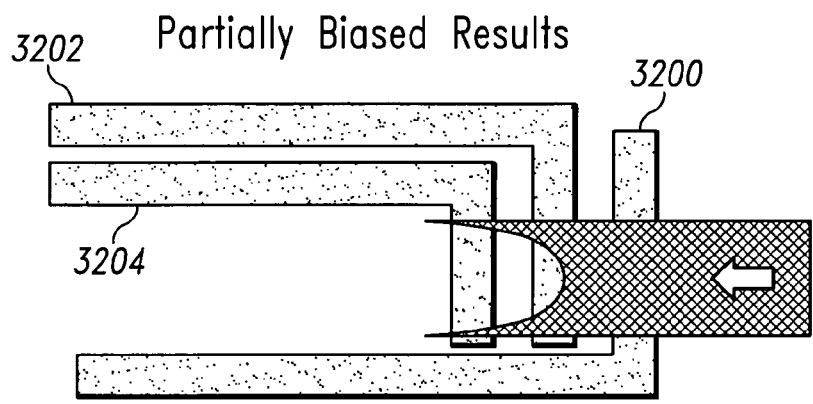
Figure 32C:
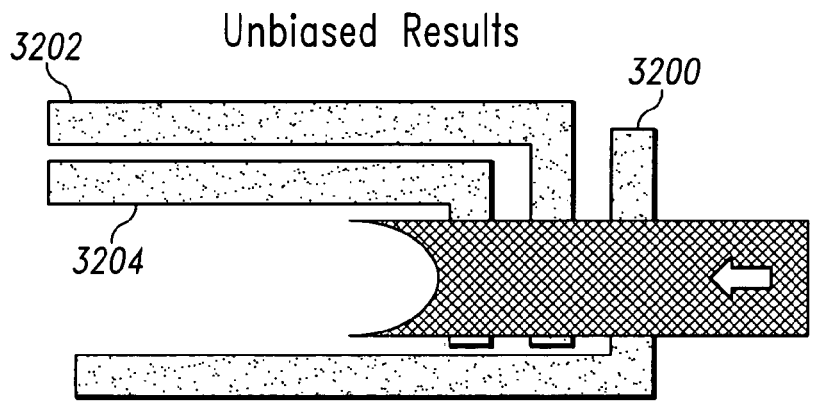

The problems associated with a concave flow front in a capillary fill space are illustrated in FIGS. 32A-C. In each of the figures, the test strip includes a working electrode 3200, a reference electrode 3202, and a downstream dose sufficiency electrode 3204 that works in conjunction with one of the measurement electrodes 3200 or 3202. In addition to the measurement zone stoichiometry problems associated with the use of the dose sufficiency electrode 3204 in conjunction with one of the measurement electrodes discussed above, FIGS. 32A-C illustrate that a sample flow front exhibiting a concave shape can also cause biased measurement results. In each drawing, the direction of sample travel is shown by the arrow. In FIG. 32A, the portions of the sample adjacent to the capillary walls have reached the dose sufficiency electrode 3204, thereby electrically completing the DC circuit between this electrode and one of the measurement electrode pair that is being monitored by the test meter in order to make the dose sufficiency determination. Although the test meter will conclude that there is sufficient sample to make a measurement at this time, the sample clearly has barely reached the reference electrode 3202 and any measurement results obtained at this time will be highly biased.

Similarly, FIG. 32B illustrates the situation where the dose sufficiency electrode 3204 has been contacted (indicating that the measurement should be started), but the reference electrode 3202 is only partially covered by the sample. Although the sample has reached the reference electrode 3202 at this time, the reference electrode 3202 is not completely covered by sample, therefore any measurement results obtained at this time will be partially biased. Both of the situations illustrated in FIGS. 32A-B will therefore indicate a false positive for dose sufficiency, thereby biasing the measurement test results. Only in the situation illustrated in FIG. 32C, where the reference electrode 3202 is completely covered by the sample, will the measurement results be unbiased due to the extent of capillary fill in the measurement zone.

Figure 33:
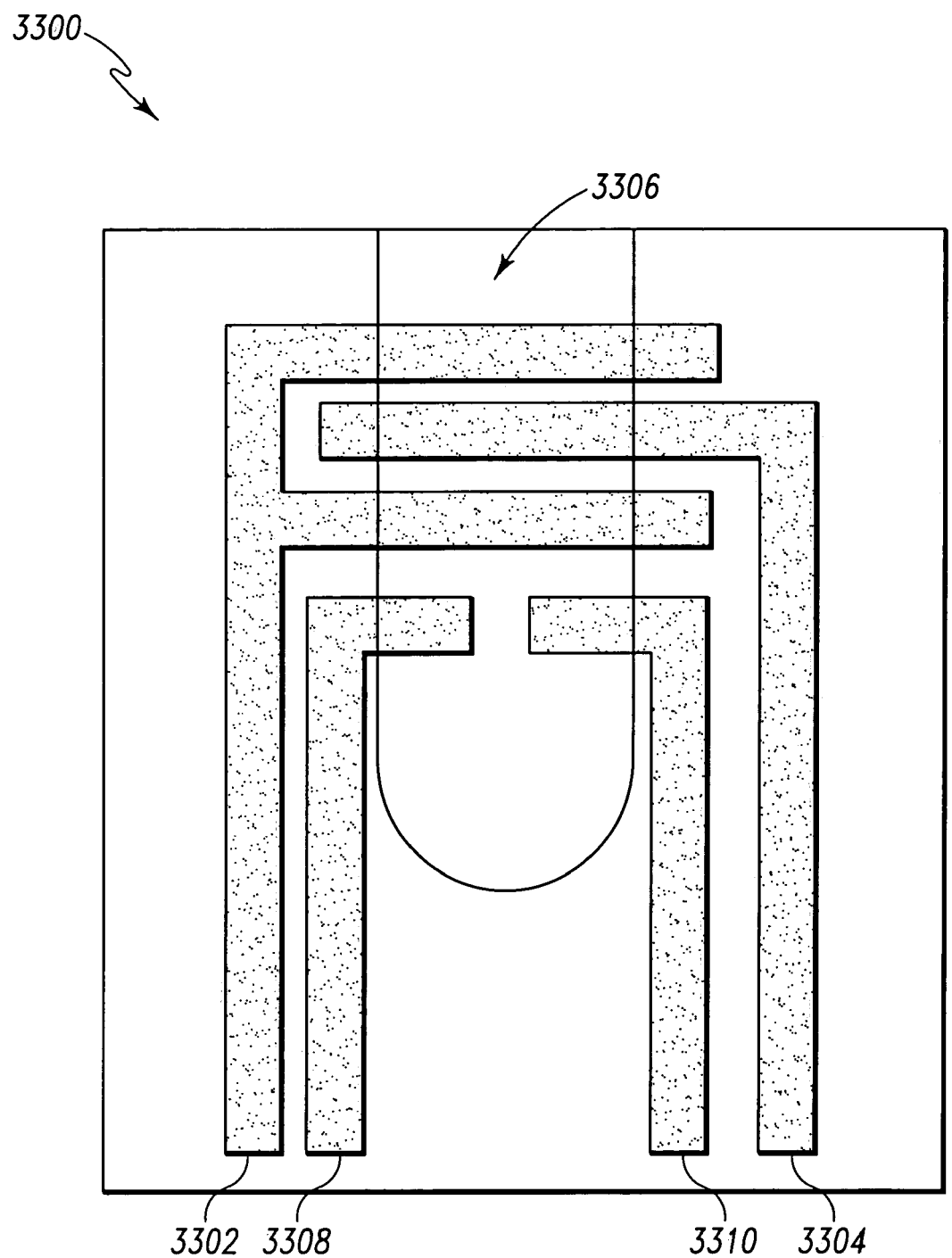
FIG. 33 is a schematic plan view of a test strip of the present invention having a pair of perpendicular dose sufficiency electrodes that are independent from the measurement electrodes.

The present invention solves the stoichiometric problems associated with the prior art designs pairing the dose sufficiency electrode with one of the measurement electrodes when making the dose sufficiency determination. As shown in FIG. 33, the present invention comprehends a test strip having an independent pair of dose sufficiency electrodes positioned downstream from the measurement electrodes. The test strip is indicated generally as 3300, and includes a measurement electrode pair consisting of a counter electrode 3302 and a working electrode 3304. The electrodes may be formed upon any suitable substrate in a multilayer test strip configuration as is known in the art and described hereinabove. The multilayer configuration of the test strip provides for the formation of a capillary fill space 3306, also as known in the art. Within the capillary fill space 3306, and downstream (relative to the direction of sample flow) from the measurement electrodes 3302 and 3304 are formed a dose sufficiency working electrode 3308 and a dose sufficiency counter electrode 3310, together forming a dose sufficiency electrode pair.

When the test strip 3300 is inserted into the test meter, the test meter will continuously check for a conduction path between the dose sufficiency electrodes 3308 and 3310 in order to determine when the sample has migrated to this region of the capillary fill space. Once the sample has reached this level, the test meter may be programmed to conclude that the measurement electrodes are covered with sample and the sample measurement sequence may be begun. It will be appreciated that, unlike as required with prior art designs, no voltage or current need be applied to either of the measurement electrodes 3302 and 3304 during the dose sufficiency test using the test strip design of FIG. 33. Thus the stoichiometry of the measurement zone is not perturbed during the dose sufficiency test cycle prior to making a measurement of the analyte of interest residing in the measurement zone. This represents a significant improvement over the dose sufficiency test methodologies of the prior art.

Figure 34A:
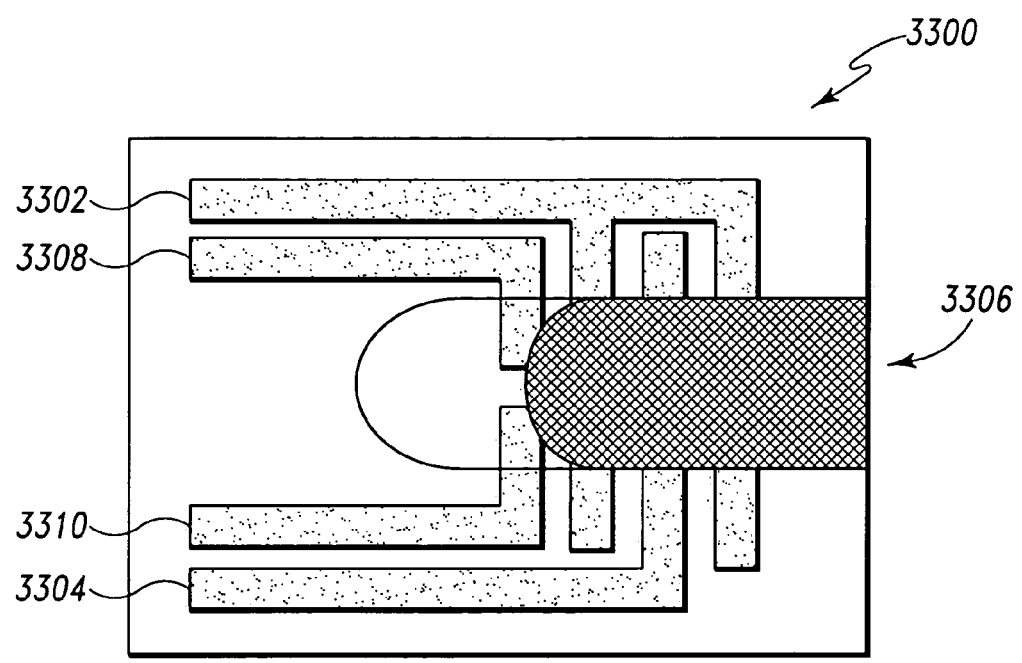
FIGS. 34A-B are schematic plan views of the test strip of FIG. 33 containing samples with convex and concave flow fronts, respectively.
Figure 34B:
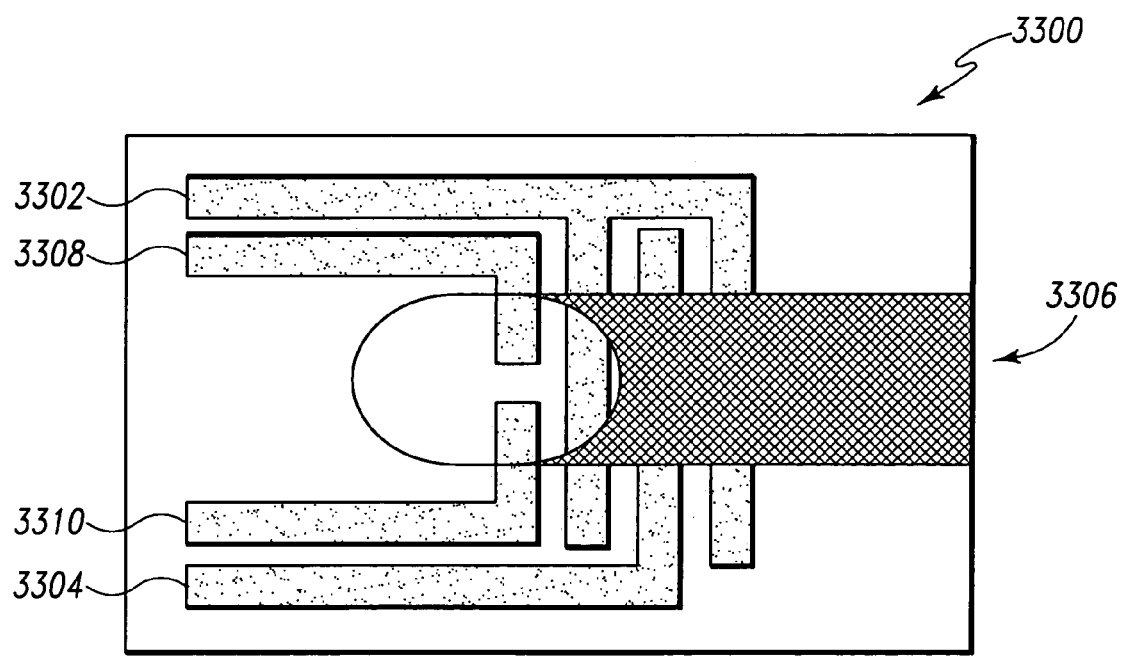

The test strip 3300 is also desirable for judging dose sufficiency when the capillary fill space is designed to produce samples that exhibit a convex flow front while filling the capillary fill space 3306, as illustrated in FIG. 34A. As can be seen, the measurement zone above the measurement electrodes 3302 and 3304 is covered with sample when the convex flow front reaches the dose sufficiency electrode pair 3308, 3310. The test strip design 3300 may not, however, produce ideal results if the capillary fill space 3306 allows the sample to exhibit a concave flow front while filling, as shown in FIG. 34B. As can be seen, the peripheral edges of the concave flow front reach the dose sufficiency electrodes 3308, 3310 before the measurement zone has been completely covered with sample. With DC or low frequency excitation (discussed in greater detail hereinbelow), the dose sufficiency electrodes 3308, 3310 will indicate sample sufficiency as soon as they are both touched by the edges of the flow front. Therefore, the dose sufficiency electrode design shown in the test strip of FIG. 33 works best when the sample filling the capillary space 3306 exhibits a convex flow front.

Figure 35A:
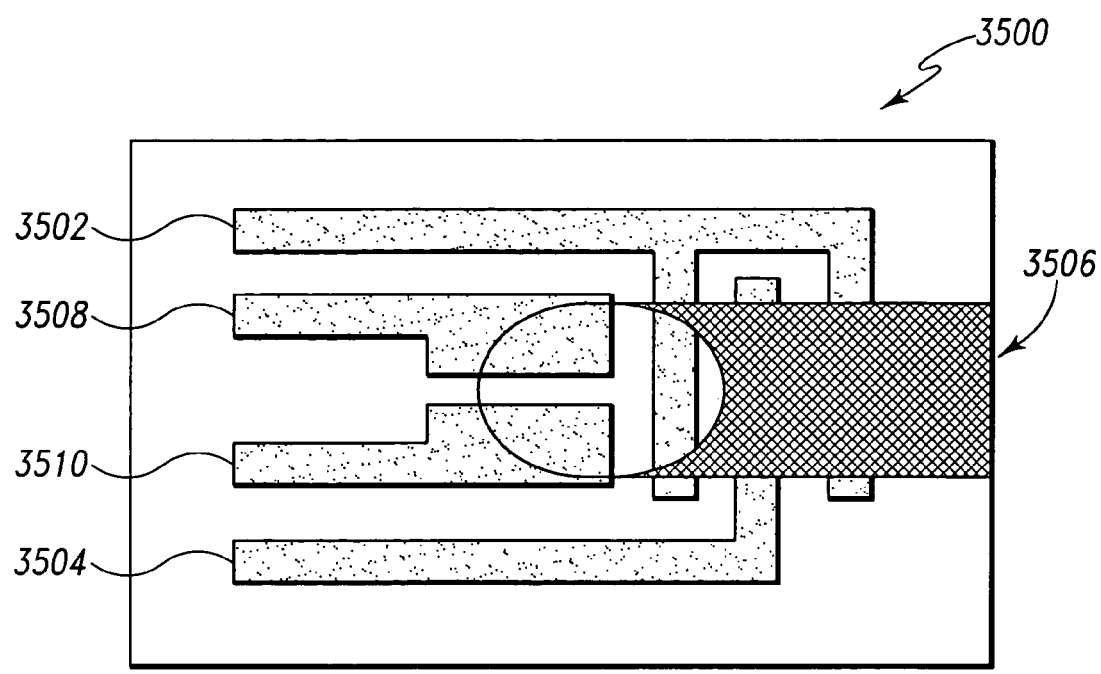
FIGS. 35A-B are schematic plan views of a test strip of the present invention having a pair of parallel dose sufficiency electrodes that are independent from the measurement electrodes.
Figure 35B:
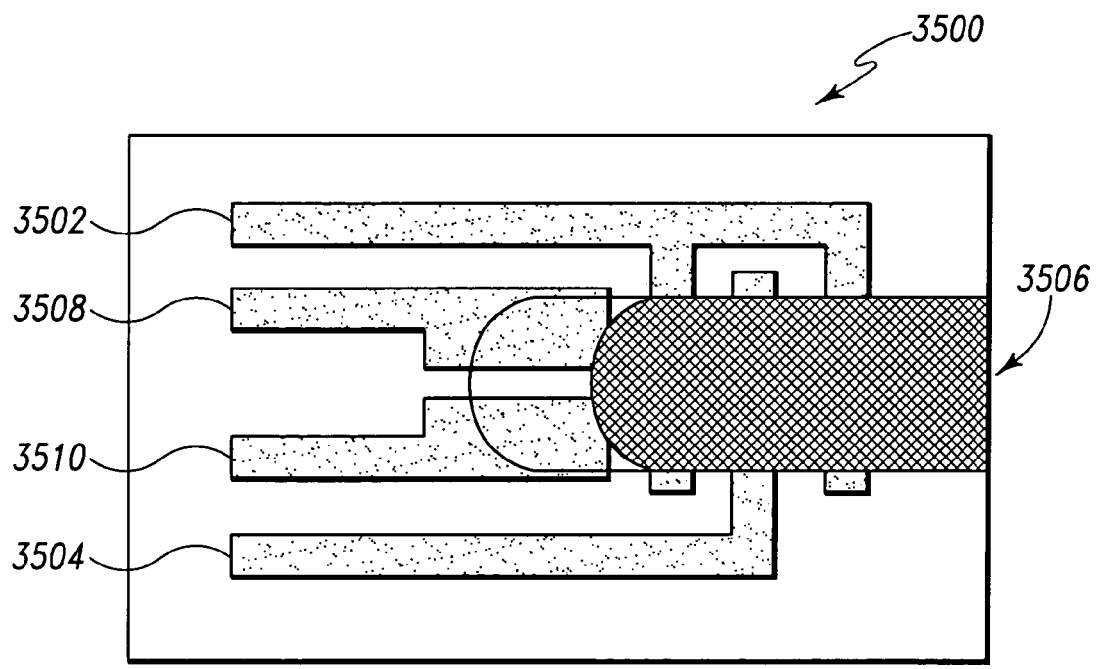

It will be appreciated that the dose sufficiency electrodes 3308, 3310 have their longest axis within the capillary fill space 3306 oriented perpendicular to the longitudinal axis of the capillary fill space 3306. Such electrodes are referred to herein as "perpendicular dose sufficiency electrodes." An alternative dose sufficiency electrode arrangement is illustrated in FIGS. 35A-B. As shown in FIG. 35A, the present invention also comprehends a test strip having an independent pair of dose sufficiency electrodes positioned downstream from the measurement electrodes, where the dose sufficiency electrodes have their longest axis within the capillary fill space oriented parallel to the longitudinal axis of the capillary fill space. Such electrodes are referred to herein as "parallel dose sufficiency electrodes." The test strip in FIG. 35 is indicated generally as 3500, and includes a measurement electrode pair consisting of a counter electrode 3502 and a working electrode 3504. The electrodes may be formed upon any suitable substrate in a multilayer test strip configuration as is known in the art and described hereinabove. The multilayer configuration of the test strip provides for the formation of a capillary fill space 3506, also as known in the art. Within the capillary fill space 3506, and downstream (relative to the direction of sample flow) from the measurement electrodes 3502 and 3504 are formed a dose sufficiency working electrode 3508 and a dose sufficiency counter electrode 3510, together forming a parallel dose sufficiency electrode pair.

When the test strip 3500 is inserted into the test meter, the test meter will continuously check for a conduction path between the dose sufficiency electrodes 3508 and 3510 in order to determine when the sample has migrated to this region of the capillary fill space. Once the sample has reached this level, the test meter may be programmed to conclude that the measurement electrodes are covered with sample and the sample measurement sequence may be begun. It will be appreciated that, as with the test strip 3300 (and unlike as required with prior art designs), no voltage or current need be applied to either of the measurement electrodes 3502 and 3504 during the dose sufficiency test using the test strip design of FIG. 35. Thus the stoichiometry of the measurement zone is not perturbed during the dose sufficiency test cycle prior to making a measurement of the analyte of interest residing in the measurement zone. This represents a significant improvement over the dose sufficiency test methodologies of the prior art.

A further improved operation is realized with the parallel dose sufficiency electrodes of the test strip 3500 when the dose sufficiency electrodes are energized with a relatively high frequency AC excitation signal. When a relatively high frequency AC signal is used as the dose sufficiency excitation signal, the dose sufficiency electrodes 3508, 3510 display significant edge effects, wherein the excitation signal traverses the gap between the electrodes only when the electrode edges along the gap are covered with the sample fluid. The test strip 3500 is illustrated in enlarged size in FIG. 36 (with only the electrode portions lying within the capillary fill space 3506 and the strip-to-meter electrode contact pads visible). When one of the pair of dose sufficiency electrodes 3508, 3510 is excited with an AC signal, the majority of the signal travels from one electrode edge to the edge of the other electrode (when the edges are covered with sample), rather than from the upper flat surface of one electrode to the upper flat surface of the other electrode. These paths of edge-to-edge electrical communication are illustrated schematically as the electric field lines 3602 in FIG. 36.

Higher AC frequencies produce the best edge-only sensitivity from the dose sufficiency electrodes. In the preferred embodiment, a 9 mV$_{rms}$ (+/−12.7 mV peak-to-peak) excitation signal of 10 kHz is used to excite one of the dose sufficiency electrodes. The gap width GW between the edges of the dose sufficiency electrodes 3508, 3510 is preferably 100-300 μm, more preferably 150-260 μm, and most preferably 255 μm. A smaller gap width GW increases the amount of signal transmitted between dose sufficiency electrodes whose edges are at least partially covered by sample; however, the capacitance of the signal transmission path increases with decreasing gap width GW.

Figure 36:
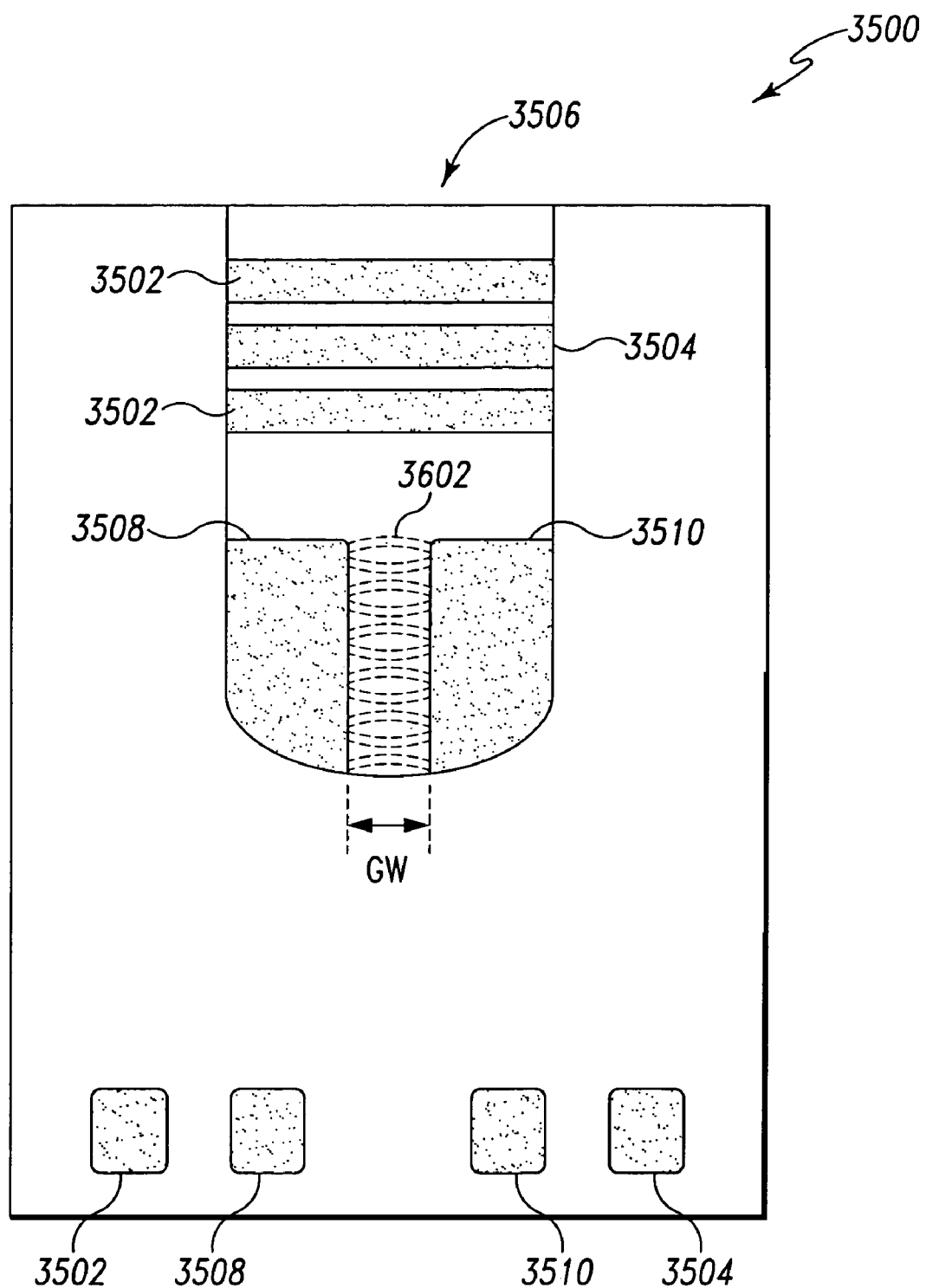
FIG. 36 is a schematic plan view of the test strip of FIG. 35, schematically illustrating the electric field lines that communicate between the electrode gap when the electrodes are covered with sample.

An advantage of the parallel dose sufficiency electrode design of FIGS. 35 and 36, when used with AC excitation, is that there is substantially no electrical communication between the electrodes until the sample covers at least a portion of the edges along the electrode gap. Therefore, a sample exhibiting the concave flow front of FIG. 35A, where the illustrated sample is touching both of the dose sufficiency electrodes 3508, 3510 but is not touching the electrode edges along the gap, will not produce any significant electrical communication between the dose sufficiency electrodes. The test meter will therefore not form a conclusion of dose sufficiency until the sample has actually bridged the dose sufficiency electrodes between the electrode edges along the gap. This will happen only after the rear-most portion of the concave flow front has reached the dose sufficiency electrodes 3508, 3510, at which point the sample has completely covered the measurement zone over the measurement electrodes. As can be seen in FIG. 35B, convex sample flow fronts will activate the dose sufficiency electrodes 3508, 3510 as soon as the flow front reaches the dose sufficiency electrodes (at which point the sample has completely covered the measurement zone over the measurement electrodes).

Another advantage to the parallel dose sufficiency electrodes illustrated in FIGS. 35 and 36 is that the amount of signal transmitted between the electrodes is proportional to the amount of the gap edges that is covered by the sample. By employing an appropriate threshold value in the test meter, a conclusion of dose sufficiency can therefore be withheld until the sample has covered a predetermined portion of the dose sufficiency electrode gap edge. Furthermore, an analysis of the dose sufficiency signal will allow the test meter to record the percentage of fill of the capillary fill space for each measurement made by the test meter, if desired.

While the electrode geometry itself demonstrates an advantage over previous embodiments in terms of detecting an adequate sample, particularly in the case of a convex flow front, it was found that further improvement is achieved in the use of AC responses over DC responses for sample detection. DC responses have the problems of being sensitive to variations in, for example, temperature, hematocrit and the analyte (glucose for example). AC responses at sufficiently high frequency can be made robust to the variation in the analyte concentration. Further, the AC response generated at sufficiently high frequencies in such capillary fill devices is primarily limited by the amount of the parallel gap between the electrode edges which is filled by the sample. Thus, for a convex flow front, little or no AC response (in this case admittance) is perceived until the trough of the flow front actually intrudes within the parallel gap of the sample sufficiency electrodes. Further, by means of threshold calibration, the sensor can be made more or less sensitive as is deemed advantageous, with a higher threshold for admittance requiring more of the parallel gap to be filled before test initiation.

A further limitation of existing devices is the inability of the electrode geometry to discern the amount of time needed to fill the capillary space of the sensor. This limitation is caused by having interdependence of the dose sufficiency electrode and the measurement electrodes. This is a further advantage of independent dose sufficiency electrodes. In the preferred embodiment a signal is first applied across the measurement electrodes prior to dosing. When a response is observed, the potential is immediately switched off and a second signal is applied across the dose sufficiency electrodes during which time the system both looks for a response to the signal (indicating electrode coverage) and marks the duration between the first event (when a response is observed at the measurement electrodes) and the second event (when a response is observed at the dose sufficiency electrodes). In cases where very long intervals may lead to erroneous results, it is possible to establish a threshold within which acceptable results may be obtained and outside of which a failsafe is triggered, preventing a response or at a minimum warning the user of potential inaccuracy. The amount of time lag between dosing and detection of a sufficient sample that is considered allowable is dependent upon the particular sensor design and chemistry. Alternatively, an independent pair of dose detection electrodes (not shown) may be added upstream from the measurement electrodes in order to detect when the sample is first applied to the sensor.

While a DC signal could be used for detection in either or both of the above events, the preferred embodiment uses an AC signal at sufficiently high frequency to avoid unnecessarily perturbing the electrochemical response at the measurement electrodes and to provide robust detection with respect to flow front irregularities.

All publications, prior applications, and other documents cited herein are hereby incorporated by reference in their entirety as if each had been individually incorporated by reference and fully set forth.

While the invention has been illustrated and described in detail in the drawings and foregoing description, the description is to be considered as illustrative and not restrictive in character. Only the preferred embodiment, and certain other embodiments deemed helpful in further explaining how to make or use the preferred embodiment, have been shown. All changes and modifications that come within the spirit of the invention are desired to be protected.

What is claimed is:

1. A method for measuring a temperature during a test for determining a concentration of medically significant component of a biological fluid, comprising the steps of:
   a) providing a sensor having at least one measurement electrode adapted to measure the biological fluid;
   b) applying a first signal to the measurement electrode;
   c) measuring a first response to the first signal;
   d) using the first response to produce an indication of a temperature of the biological fluid;
   e) applying a second signal to the measurement electrode;
   f) measuring a second response to the second signal to produce an indication of the concentration of the medically significant component; and
   g) determining a temperature-corrected concentration of the medically significant component based upon the first responses.

2. The method of claim 1 wherein the sensor comprises a disposable test strip.

3. The method of claim 1, wherein
   the first signal comprises a signal having an AC component and the first response comprises and AC response to the first signal.

4. The method of claim 3, wherein the first AC response comprises an admittance.

5. The method of claim 3, further comprising the steps of:
   (c) applying a second signal having an AC component to the biological fluid, wherein said first and second signals may be applied sequentially or simultaneously;
   (d) measuring a second AC response to the second signal; and
   (e) further using the second AC response to produce the indication of a temperature of the biological fluid.

6. A method for measuring a temperature during a test for determining a concentration of a medically significant component of a biological fluid, comprising the steps of:
   a) providing a sensor having at least one measurement electrode adapted to measure the biological fluid;
   b) applying a first temperature measurement signal having an AC component to the measurement electrode;
   c) measuring a first AC temperature measurement response to the first temperature measurement signal;
   d) using the first AC temperature measurement response to produce an indication of a temperature of the biological fluid;
   e) applying a first concentration measurement signal to the measurement electrode;
   f) measuring a first concentration measurement response to the first concentration measurement signal to produce an indication of the concentration of the medically significant component; and
   g) determining a temperature-corrected concentration of the medically significant component based upon the first AC temperature measurement response and the first concentration measurement response.

7. The method of claim 6, wherein the first AC response comprises an admittance.

8. The method of claim 6, further comprising the steps of:
   (c) applying a second temperature measurement signal having an AC component to the biological fluid, wherein said first and second temperature measurement signals may be applied sequentially or simultaneously;
   (d) measuring a second AC temperature measurement response to the second temperature measurement signal; and
   (e) further determining the temperature-corrected concentration of the medically significant component based upon the first AC temperature measurement response, the second AC temperature measurement response and the first concentration measurement response.

9. The method of claim 8, wherein the second temperature measurement signal is an AC signal.

10. The method of claim 8, wherein the second AC temperature measurement response comprises an admittance measurement.

11. The method of claim 8, wherein the second AC temperature measurement response comprises magnitude information.

12. The method of claim 6, wherein the first temperature measurement signal is an AC signal.

13. The method of claim 6, wherein the first AC temperature measurement response comprises magnitude information.

14. The method of claim 6, wherein the first temperature measurement signal comprises a number of frequencies applied sequentially or simultaneously, wherein the number is greater than one.

15. The method of claim 14, wherein the number is not less than two and not grater than four.

16. The method of claim 14, wherein the number is greater than four.

17. The method of claim 6, wherein the AC component of the first temperature measurement signal has a frequency not less than 1 Hz and not greater than 20 kHz.

18. The method of claim 6, wherein the biological fluid is blood.

19. The method of claim 6, wherein said first temperature measurement signal comprises four first temperature measurement signals applied sequentially or simultaneously, and wherein step (d) comprises producing an indication of the temperature using $$T_{est} = b_0 + b_1(Y_1 - Y_2) + b_2(Y_3 - Y_4) + b_3 H_{est}$$

Where: $T_{est}$ is the temperature, $b_0, b_1, b_2$ and $b_3$ are constants $Y_1, Y_2, Y_3$ and $Y_4$ are respective AC responses of the four first temperature measurement signals (expressed as admittance), and $H_{est}$ is an estimated hematocrit value.

20. A method of accounting for the effect of a temperature variation on a test for a glucose concentration of a biological fluid comprising:
   a) providing a sensor having at least one measurement electrode adapted to measure the biological fluid;
   b) applying a first temperature measurement test signal having an AC component to the measurement electrode, the first temperature measurement test signal having a first frequency;
   c) measuring at least a first AC temperature measurement response to the first temperature measurement test signal;
   d) determining a temperature value of the biological fluid using the first AC temperature measurement response;
   e) applying a first concentration measurement signal to the measurement electrode;
   f) measuring at least a first concentration measurement response to the first concentration measurement signal to produce an indication of the glucose concentration of the biological fluid; and
   g) determining a temperature-corrected glucose concentration of the biological fluid base at least in part upon the temperature value and the first concentration measurement response.

21. The method of claim 20, wherein the determining a temperature value comprises determining a hematocrit value of the biological fluid and using the hematocrit value in combination with the first AC temperature measurement response to determine the temperature value.

22. The method of claim 20, wherein the first AC temperature measurement response includes an admittance.

23. The method of claim 20, further comprising the steps of:
   e) applying a second temperature measurement test signal having an AC component to the biological fluid, the second temperature measurement test signal having a second frequency, wherein said first and second temperature measurement test signals may be applied sequentially or simultaneously; and
   f) measuring at least a second AC temperature measurement response to the second temperature measurement test signal; and
   g) using the second AC temperature measurement response in the determining a temperature value of the biological fluid.

24. The method of claim 23, further comprising the steps of:
   h) applying a third temperature measurement test signal having an AC component to the biological fluid, the third temperature measurement test signal having a third frequency, wherein said first, second and third temperature measurement test signals may be applied sequentially or simultaneously;
   i) measuring at least a third AC temperature measurement response to the third temperature measurement test signal;
   j) applying a fourth temperature measurement test signal having an AC component to the biological fluid, the fourth temperature measurement test signal having a fourth frequency;
   k) measuring at least a fourth AC temperature measurement response to the fourth test signal; and
   l) using the third AC temperature measurement response and the fourth AC temperature measurement response in the determining a temperature value of the biological fluid.

* * * * *

UNITED STATES PATENT AND TRADEMARK OFFICE
CERTIFICATE OF CORRECTION

PATENT NO. : 7,494,816 B2
APPLICATION NO. : 10/687668
DATED : February 24, 2009
INVENTOR(S) : David W. Burke It is certified that error appears in the above-identified patent and that said Letters Patent is hereby corrected as shown below:

In Claim 1, column 31, item (g) please add --and second-- between the words "based upon the first" and "responses" so that (g) reads: "g) determining a temperature-corrected concentration of the medically significant component based upon the first and second responses.".

In claim 19, column 32, line 67, please change "$T_{est}=b_0+b_1(Y_1-Y_2)+b_2(Y_3-Y_4)+b_3H_{est}$" to --$T_{est} = b_0 + b_1(Y_1 - Y_2) + b_2(Y_3 - Y_4) + b_3H_{est}$--.

In claim 19, column 33, line 1, please change "$T_{est}$" to --$T_{est}$--.

In claim 19, column 33, line 6, please change "$H_{est}$" to --$H_{est}$--.

Signed and Sealed this

Fourteenth Day of July, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,494,816 B2  Page 1 of 1
APPLICATION NO. : 10/687668
DATED : February 24, 2009
INVENTOR(S) : David W. Burke It is certified that error appears in the above-identified patent and that said Letters Patent is hereby corrected as shown below:

In Claim 1, column 31, lines 42-43, please add --and second-- between the words "based upon the first" and "responses" so that (g) reads: "g) determining a temperature-corrected concentration of the medically significant component based upon the first and second responses.".

In claim 19, column 32, line 67, please change "$T_{est}=b_0+b_1(Y_1-Y_2)+b_2(Y_3-Y_4)+b_3H_{est}$" to --$T_{est} = b_0 + b_1(Y_1 - Y_2) + b_2(Y_3 - Y_4) + b_3H_{est}$--.

In claim 19, column 33, line 1, please change "$T_{est}$" to --$T_{est}$--.

In claim 19, column 33, line 6, please change "$H_{est}$" to --$H_{est}$--.

This certificate supersedes the Certificate of Correction issued July 14, 2009.

Signed and Sealed this

Eighteenth Day of August, 2009

David J. Kappos
*Director of the United States Patent and Trademark Office*